United States Patent
Song et al.

(10) Patent No.: US 6,545,054 B1
(45) Date of Patent: *Apr. 8, 2003

(54) ALKENYL AND ALKYNYL COMPOUNDS AS INHIBITORS OF FACTOR XA

(75) Inventors: Yonghong Song, Foster City, CA (US); Robert M. Scarborough, Half Moon Bay, CA (US); Bing-Yan Zhu, Belmont, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/501,370

(22) Filed: Feb. 11, 2000

Related U.S. Application Data

(60) Provisional application No. 60/119,640, filed on Feb. 11, 1999.

(51) Int. Cl.$^7$ .......................... A61K 31/18; C07C 311/37
(52) U.S. Cl. .......................... 514/603; 564/84; 564/86; 564/164; 564/168; 562/430; 548/336.5
(58) Field of Search .............................. 564/84, 90, 86; 514/603

(56) References Cited

U.S. PATENT DOCUMENTS 4,588,587 A 5/1986 Gasic .......................... 424/95

FOREIGN PATENT DOCUMENTS

| WO | WO 94/13693 | | 6/1994 |
| WO | WO 95/06044 | * | 3/1995 |
| WO | 98/28269 | | 7/1998 |
| WO | 98-28282 | | 7/1998 |
| WO | 98/57934 | | 12/1998 |
| WO | WO 99/00356 | * | 1/1999 |
| WO | WO 2000/47554 | * | 8/2000 |

OTHER PUBLICATIONS

R. Kuhn, et al., "Addition von Maleinsäure–anhydrid an Polyene. (Über konjugierte Dopplebindungen, XIV.)" *Berichte Der Deutschen Chemischen Gesellschaft*, vol. 63, pp. 2662–2679, (1930).

P. H. G. op het Veld, et al., "Synthetic and Mechanistic aspects of the Photocyclization of 2–(beta–arylvinyl)biphenyls into 9–aryl–9, 10–dihydrophenanthrenes", *Journal of the Chemical Society, Perkin Transactions 2*, No. 9, pp. 915–922, (1978).

W. E. Bachmann, et al., "Reduction by Magnesium and Magnesium Halide. XII. The reaction between Epoxy Ketones and Grignard Reagents", *Journal of the American Chemical Society*, vol. 56, No. 7, pp. 1559–1560, (1934).

V. N. Listvyan, et al., "(p–Benzoylbenzylidene) Triphenylphosphorane and its Application for the Preparation of Unsaturated Benzophenone Derivatives by the Wittig Reaction", *Journal of General Chemistry USSR*, vol. 50, No. 7, part 1, Jul. 1980, pp. 1231–1235, XP002161033.

D. Hellwinkel, et al., "Einfache Synthesen von 1, 2–Diaryl– und Triarylethenen mit Trägergebundenen Fluoridbasen", *Synthesis*, No. 9, pp. 973–978, (1994).

S. A. Vartanyan, et al., "Synthesis of 1, 1–diaryl–2–haloethanes and Some of Their Reactions", pp. 396, Chemical Abstracts, vol. 78, No. 13, Apr. 2, 1973, abstract No. 83924P, XP002161034.

Takayanagi et al., Chemical Abstracts, vol. 129:161414, 1998.*

CAS Printout for WO 99/00356, 1999.*

Blood et al., J. Org. Chem., 22, pp. 873–876, 1957.*

Claeson, G. "Synthetic Peptides and Peptidomimetics as Substrates and Inhibitors of Thrombin and Other Proteases in the Blood Coagulation System", *Blood Coag. Fibrinol.*, 5, pp. 411–436 (1994).

Davie, E.J. et al., "The Coagulation Cascade: Initiation, Maintenance and Regulation", *Biochemistry*, 30, pp. 10363–10370 (1991).

Etingin, O.R., et al., "Viral Activation of the Coagulation Cascade: Molecular Interactions at the Surface of Infected Endothelial Cells", *Cell*, 61, pp. 657–662 (1990).

Furie, B., et al., "The Molecular Basis of Blood Coagulation", *Cell*, 53, pp. 505–518 (1988).

Girard, T.J. et al., "Functional Significance of the Kunitztype Inhibitory Domains of Lipoprotein–associated Coagulation Inhibitor", *Nature*, 338, pp. 518–520 (1989).

Hoover, R.J., et al., "The Adhesive Interaction Between Polymorphonuclear Leukocytes and Endothelial Cells in Vitro", *Cell*, 14, pp. 423–428 (1978).

Tidwell, R.R. et al., "Strategies for Anticoagulation With Synthetic Protease Inhibitors. Xa Inhibitors Versus Thrombin Inhibitors", *Thromb. Res.*, 19, pp. 339–349 (1980).

\* cited by examiner

*Primary Examiner*—Richard L. Raymond
(74) *Attorney, Agent, or Firm*—Townsend and Townsend and Crew LLP

(57) ABSTRACT

Alkenyl and alkynyl compounds as potent and highly selective inhibitors of factor Xa isolated or assembled in the prothrombinase complex and compositions containing such alkenyl and alkynyl compounds are described. Such compounds show selectivity for factor Xa over other proteases of the coagulation (e.g., thrombin, fvIIa, fIXa) or the fibrinolytic cascades (e.g., plasminogen activators, plasmin). Methods for using such alkenyl and alkynyl compounds as diagnostic or therapeutic agents for prevention or treatment of a condition in a mammal characterized by undesired coagulation disorders, such as thrombosis, are also described.

13 Claims, No Drawings

ALKENYL AND ALKYNYL COMPOUNDS AS INHIBITORS OF FACTOR XA

CROSS REFERENCE TO RELATED APPLICATIONS

This application claims priority to U.S. Provisional Patent Application No. 60/119,640, filed on Feb. 11, 1999, which is herein incorporated in its entirety by reference.

FIELD OF THE INVENTION

The invention relates to novel alkenyl and alkynyl compounds, alone or as part of a composition, which are potent and highly selective inhibitors of factor Xa isolated or assembled in the prothrombinase complex. Such compounds show selectivity for factor Xa over other proteases of the coagulation (e.g., thrombin, fvhla, fixa) or the fibrinolytic cascades (e.g., plasminogen activators, plasmin). The invention further relates to methods for using such alkenyl and alkynyl compounds as agents for preventing or treating a condition in a mammal characterized by undesired coagulation disorders, such as thrombosis.

BACKGROUND OF THE INVENTION

Hemostasis, the control of bleeding, occurs by surgical means, or by the physiological properties of vasoconstriction and coagulation. Under normal hemostatic circumstances, the body maintains an acute balance of clot formation and clot removal (fibrinolysis). The blood coagulation cascade involves the conversion of a variety of inactive enzymes (zymogens) into active enzymes which ultimately convert the soluble plasma protein fibrinogen into an insoluble matrix of highly cross-linked fibrin. Davie, E.J. et al., "The Coagulation Cascade: Initiation, Maintenance and Regulation", Biochemistry, 30, 10363–10370 (1991). These plasma glycoprotein zymogens include Factor XII, Factor XI, Factor IX, Factor X, Factor VII, and prothrombin. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

Blood platelets which adhere to damaged blood vessels are activated and incorporated into the clot and thus play a major role in the initial formation and stabilization of hemostatic "plugs". In certain diseases of the cardiovascular system, deviations from normal hemostasis push the balance of clot formation and clot dissolution towards life-threatening thrombus formation when thrombi occlude blood flow in coronary vessels (myocardial infarctions) or limb and pulmonary veins (venous thrombosis). Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Under normal circumstances, thrombin can also play an anticoagulant role in hemostasis through its ability to convert protein C into activated protein C (aPC) in a thrombomodulin-dependent manner. However, in atherosclerotic arteries these thrombin activities can initiate the formation of a thrombus, which is a major factor in pathogenesis of vasoocclusive conditions such as myocardial infarction, unstable angina, nonhemorrhagic stroke and reocclusion of coronary arteries after angioplasty or thrombolytic therapy. Thrombin is also a potent inducer of smooth muscle cell proliferation and may therefore be involved in a variety of proliferative responses such as restenosis after angioplasty and graft induced atherosclerosis. In addition, thrombin is chemotactic for leukocytes and may therefore play a role in inflammation. (Hoover, R.J., et al. Cell, 4, 423 (1978); Etingin, O. R., et al., Cell, 6 657 (1990). These observations indicate that inhibition of thrombin formation or inhibition of thrombin itself may be effective in preventing or treating thrombosis, limiting restenosis and controlling inflammation.

Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

The formation of thrombin is the result of the proteolytic cleavage of its precursor prothrombin at the Arg-Thr linkage at positions 271–272 and the Arg-Ile linkage at positions 320–321. This activation is catalyzed by the prothrombinase complex, which is assembled on the membrane surfaces of platelets, monocytes, and endothelial cells. The complex consists of Factor Xa (a serine protease), Factor Va (a cofactor), calcium ions and the acidic phospholipid surface. Factor Xa is the activated form of its precursor, Factor X, which is secreted by the liver as a 58 kd precursor and is converted to the active form, Factor Xa, in both the extrinsic and intrinsic blood coagulation pathways. Factor X is a member of the calcium ion binding, gamma carboxyglutamyl (Gla)-containing, vitamin K dependent, blood coagulation glycoprotein family, which also includes Factors VII and IX, prothrombin, protein C and protein S (Furie, B., et al., Cell, 53, 505 (1988)). The activity of Factor Xa in effecting the conversion of prothrombin to thrombin is dependent on its inclusion in the prothrombinase complex.

The prothrombinase complex converts the zymogen prothrombin into the active procoagulant thrombin. It is therefore understood that Factor Xa catalyzes the next-to- last step in the blood coagulation cascade, namely the formation of the serine protease thrombin. In turn, thrombin then acts to cleave soluble fibrinogen in the plasma to form insoluble fibrin.

The location of the prothrombinase complex at the convergence of the intrinsic and extrinsic coagulation pathways, and the resulting significant amplification of thrombin generation (several hundred-thousand fold faster in effecting the conversion of prothrombin to thrombin than Factor Xa in soluble form) mediated by the complex at a limited number of targeted catalytic units present at vascular lesion sites, suggests that inhibition of thrombin generation is a desirable method to block uncontrolled procoagulant activity. It has been suggested that compounds which selectively inhibit factor Xa may be useful as in vitro diagnostic agents, or for therapeutic administration in certain thrombotic disorders, see e.g., WO 94/13693. Unlike thrombin, which acts on a variety of protein substrates as well as at a specific receptor, factor Xa appears to have a single physiologic substrate, namely prothrombin.

Plasma contains an endogenous inhibitor of both the factor VIIa-tissue factor (TF) complex and factor Xa called tissue factor pathway inhibitor (TFPI). TFPI is a Kunitz-type protease inhibitor with three tandem Kunitz domains. TFPI inhibits the TF/fVIIa complex in a two-step mechanism which includes the initial interaction of the second Kunitz domain of TFPI with the active site of factor Xa, thereby inhibiting the proteolytic activity of factor Xa. The second step involves the inhibition of the TF/fVIIa complex by formation of a quaternary complex TF/fVIIa/TFPI/fXa as described by Girard, T. J. et aL, "Functional Significance of the Kunitz-type Inhibitory Domains of Lipoprotein-associated Coagulation Inhibitor", Nature, 3, 518–520 (1989).

Polypeptides derived from hematophagous organisms have been reported which are highly potent and specific inhibitors of factor Xa, e.g., U.S. Pat. No. 4,588,587. Also, Factor Xa inhibitory compounds which are not large polypeptide-type inhibitors have also been reported, e.g., Tidwell, R. R. et al., "Strategies for Anticoagulation With Synthetic Protease Inhibitors. Xa Inhibitors Versus Thrombin Inhibitors", Thromb. Res., 19, 339–349 (1980)

Accordingly, there exists a need in the art for effective therapeutic agents for the regulation of hemostasis. There also exists a need in the art for effective therapeutic agents for the prevention and treatment of thrombus formation and other pathological processes in the vasculature induced by thrombin such as, for example, restenosis and inflammation. Particularly needed are small molecule antagonists or inhibitors of Factor X or of its activated form Factor Xa. The invention as described below answers this need.

SUMMARY OF THE INVENTION

The invention relates to alkenyl and alkynyl compounds capable of assisting in maintaining the integrity of mammalian circulation after injury, inflammation, disease, congenital defect, dysfunction or other disruption. In particular, the invention provides alkenyl and alkynyl compounds, including their pharmaceutically acceptable isomers, salts, hydrates, solvates and prodrug derivatives, having certain biological properties and useful as potent and specific inhibitors of blood coagulation. The alkenyl and alkynyl compounds of the invention are potent and highly selective inhibitors of isolated factor Xa when assembled in the prothrombinase complex. The compounds of the invention exhibit selectivity for factor Xa over other proteases of the coagulation cascade (e.g., thrombin) or the fibrinolytic cascade.

The invention also provides pharmaceutical compositions comprising an alkenyl or alkynyl compound of the invention and a pharmaceutically acceptable carrier.

The compounds of the invention are useful as diagnostic reagents as well as antithrombotic agents. Accordingly, the invention further provides a method of using the compounds of the invention in the diagnosis, treatment and/or prevention of a condition in a mammal characterized by undesired coagulation disorders (e.g., thrombotically mediated acute coronary or cerebrovascular syndrome, thrombotic syndrome occurring in the venous system, coagulopathy, and any thrombotic complications associated with extracorporeal circulation or instrumentation).

The invention still further relates to a method of using the compounds of the invention for the inhibition of coagulation in biological samples.

DEFINITIONS

In accordance with the invention and as used herein, the following terms are defined with the following meanings, unless explicitly stated otherwise.

The term "alkenyl" as used herein refers to a trivalent straight chain or branched chain unsaturated aliphatic radical radical that includes at least two carbons joined by a double bond. The term "alkinyl" (or "alkynyl") as used herein refers to a straight or branched chain aliphatic radical that includes at least two carbons joined by a triple bond. If no number of carbons is specified, "alkenyl" and "alkinyl" each refer to radicals having from 2–12 carbon atoms.

The term "alkyl" as used herein refers to saturated aliphatic groups including straight-chain (i.e. linear) and branched-chain groups having the number of carbon atoms specified, or if no number is specified, having up to 12 carbon atoms. The term "cycloalkyl" as used herein refers to a mono-, bi-, or tricyclic aliphatic ring system having 3 to 14 carbon atoms, preferably, 3 to 7 carbon atoms.

As used herein, the terms "carbocyclic ring structure" and "$C_{3-6}$ carbocyclic mono, bicyclic or tricyclic ring structure" or the like are each intended to mean stable ring structures having only carbon atoms as ring atoms wherein the ring structure is a substituted or unsubstituted member selected from the group consisting of a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adarnantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the groups indicated for that structure if such substitution(s) would result in a stable compound.

The term "arylalkyl" which is included with the term "carbocyclic aryl" as used herein refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1–4 heteroatoms in the ring selected from N, O and S; a stable bicyclic ring structure having a total of from 7 to 12 atoms in the two rings wherein at least one of the two rings has from 1–4 heteroatoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1–4 heteroatoms selected from N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated groups if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocyclic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocyclic ring structures.

As used herein the term "aromatic heterocyclic ring system" refers to a monocyclic and bicyclic heterocyclic ring system containing at least one aromatic ring. The terms "halo" or "halogen" as used herein refer to Cl, Br, F or I group. The term "haloalkyl" and the like, refer to a carbon radical having at least one hydrogen atom replaced by a Cl, Br, F or I atom. A mixture of different halo atoms may be used if more than one hydrogen atom is replaced. For example, a haloalkyl includes chloromethyl (—CH$_2$Cl). Trihaloalkyl includes, for example, trifluoromethyl (-CF$_3$) and the like as preferred radicals.

The term "methylene" refers to —CH$_2$—.

The term "pharmaceutically acceptable salts" as used herein includes salts of compounds of the invention derived from the combination of a compound of the invention and an organic or inorganic acid or base. Preferably, a pharmaceutically acceptable salt of a compound of the invention is a pharmaceutically acceptable acid addition salt or a pharmaceutically acceptable base addition salt, more preferably, a pharmaceutically acceptable base addition salt.

"Pharmaceutically acceptable acid addition salt" as used herein refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" as used herein refers to those salts derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

The term "biological property" as used herein means an in vivo effector or antigenic function or activity that is directly or indirectly performed by a compound of the invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

The term "isomer" as used herein refers to a compound having the same number and kind of atoms and hence the same molecular weight as another compound, but differing in respect to the arrangement or configuration of the atoms of the compound. The term "isomer" also includes diastereoisomers, enantiomers or mixtures thereof since in the compounds of the invention, carbon atoms bonded to four non-identical substituents are asymmetric. Accordingly, the syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of the invention, may be in one of two configurations (R or S) and both are within the scope of the invention.

DETAILED DESCRIPTION OF THE INVENTION

The invention provides compounds of formula I:

D-E-Q-Z-A-T-M-J (I)

E of formula I is a $C_{3-6}$ carbocyclic ring structure or a three to ten membered heterocyclic monocyclic or bicyclic ring structure system containing 1–4 heteroatoms selected from N, O and S. E may be further substituted with 0 to 4 R groups independently selected from the group consisting of:

(i) H, —SH, —OH, —Cl, —F, —Br, —I, —CN, —$NO_2$, —CHO, —COOH, —NR'R" and (ii) a substituent member selected from the group consisting of a linear or branched $C_{1-12}$alkyl group, a linear or branched $C_{2-12}$alkenyl group, a linear or branched $C_{2-12}$alkinyl group and a $C_{3-12}$cycloalkyl group which may have linear or branched chained portions, where for each substituent member:

(a) two hydrogens on the same carbon atom of the alkyl, alkenyl, alkinyl or cycloalkyl substituent member may be replaced with =O or =N(R'");

(b) one or more hydrogens, independently, on the alkyl, alkenyl, alkinyl or cycloalkyl substituent member or on the —NH— chain bridging groups may be replaced by $R^{iv}$; or (c) one or more hydrogens, independently, on carbon atom(s) of the alkyl, alkenyl, alkinyl or cycloalkyl substituent member, on the —NH— chain bridging group or of R', R", R'"or $R^{iv}$ may form an intracyclic bond to form a $C_{3-12}$ carbocyclic ring structure or a three to seven membered heterocyclic ring containing 1–4 heteroatoms selected, independently, from N, O and S. According to the invention, substituent member (ii) may further contain from 0 to 4 chain bridging groups independently selected from the group consisting of —NH—, —O—, —S—, —S(=O)—, and —S(=O)$_2$—.

R', R", R'" and $R^{iv}$ are each a member independently selected from the group consisting of H, —$(CH_2)_{0-12}$—SH, —$(CH_2)_{0-12}$—OH, —$(CH_2)_{0-12}$—$NH_2$, —$(CH_2)_{0-12}$—Cl, —$(CH_2)_{0-12}$—F, —$(CH_2)_{0-12}$—Br, —$(CH_2)_{0-12}$—I, —$(CF_2)_{1-5}$ —$(CF_3)$, —$(CH_2)_{0-12}$—$(CF_3)$, —$(CH_2)_{0-12}$—CN, —$(CH_2)_{0-12}$—$NO_2$, —$(CH_2)_{0-12}$—CHO, —$C_{1-12}$alkyl, —$_{0-12}$alkyl-N($R^a$)($R^b$)$_{0-1}$—$C_{0-12}$-alkyl, —$(CH_2)_{0-12}$—CH=(CH)$_{0-1}$—$(CH_2)_{0-12}$$(CH_3)_{0-1}$,—O—$C_{1-12}$alkyl—N($R^a$) ($R^b$)$_{0-1}$—$C_{0-12}$alkyl, —$C_{0-12}$alkyl—O—$C_{1-12}$alkyl, —$C_{0-12}$alkyl—O—$C_{2-12}$alkenyl, —$C_{2-12}$alkenyl—O—$C_{1-12}$alkyl, —$C_{2-12}$alkinyl, —$C_{0-12}$alkyl—O—$C_{1-6}$alkinyl, —$C(_{0-12}$alkinyl—O—$C_{0-12}$alkyl—, —$C_{6-10}$aryl, —$CO_{0-12}$alkyl—O—$C_{6-10}$aryl, —S(=O)$_{0-2}$—$C_{1-12}$alkyl—N($R^a$) ($R^b$)$_{0-1}$,—$C_{0-12}$alkyl, —$C_{0-12}$alkyl—S(=O)$_{0-2}$—$C_{1-12}$alkyl, —$CO_{0-12}$alkyl—S(=O)$_{0-2}$—$C_{2-12}$alkenyl, —$C_{2-12}$alkenyl—S(=O)$_{0-2}$—$C_{1-12}$alkyl, —$C_{0-12}$alkeyl—S(=O)$_{0-2}$—$_{16}$alkinyl, —$C_{1-6}$alkinyl, —$C_{0-12}$alkinyl—S(=O)$_{0-2}$—$C_{0-12}$alkyl—, —$C_{0-12}$alkyl—S(=O)$_{02}$—$C_{6-10}$aryl, —$CO_{0-12}$alkylC$_{6-10}$aryl, —$C_{2-12}$alkenylC$_{6-10}$aryl, —$C_{2-12}$alkinylC $_{6-10}$aryl, —COOH, —$CO_{0-12}$alkyl—COO—$C_{1-12}$alkyl, —$C_{0-12}$alkyl—COO—$C_{2-12}$alkenyl, —$C_{0-12}$alkyl—COO—$C_{2-12}$alkinyl, —$C_{2-12}$alkenyl—COO—$C_{1-12}$alkyl, —$C_{2-12}$alkinyl—COO—$C_{1-12}$alkyl, —$C_{2-12}$alkenyl—COO—$C_{1-12}$alkyl, —$C_{2-12}$alkinyl—COO—$C_{1-12}$alkyl, —$C_{6-10}$aryl monocyclic or bicyclic ring structure, and a three to ten membered heterocyclic monocyclic or bicyclic heterocyclic ring structure containing 1–4 heteroatoms selected from N, O and S.

$R^a$ and $R^b$ are each independently selected from the group consisting of H, —CN, —$C_{0-6}$alkyl—SH, —$C_{0-6}$alkyl—OH, —$C_{0-6}$alkyl—CHO, —$C_{0-6}$alkyl—COOH, —$C_{0-6}$alkyl—NR'R", —$C_{0-6}$alkenyl—SH, —$CO_{0-6}$alkenyl—OH, —$C_{0-6}$alkenyl—CHO, —$C_{0-6}$alkenyl—COOH, —$C_{0-6}$alkenyl—NR'R", —$C_{0-6}$alkinyl—SH, —$C_{0-6}$alkinyl—OH, —$CO_{0-6}$alkinyl—CHO, —$C_{0-6}$alkinyl—COOH, —$CO_{0-6}$alkinyl—NR'R", —$C_{1-6}$alkyl, —$(CH_2)_{1-6}$—Cl, —$(CH_2)_{1-6}$—F, —$(CH_2)_{1-6}$—Br, —$(CH_2)_{1-6}$—I, —$(CF_2)_{1-3}$—$(CF_3)$, —$(CH_2)_{1-6}$—$(CF_3)$, —$(CH_2)_{1-6}$—CN, —$(CH_2)_{0-6}$—$NO_2$, —$C_{1-6}$alkyl, —$(CH_2)_{0-4}$—CH=(CH)$_{0-1}$, —$(CH_2)_{0-4}$$(CH_3)_{0-1}$, —$C_{0-5}$alkyl—O—$C_{1-6}$alkyl, —$C_{0-5}$alkyl—O—$C_{2-6}$alkenyl, $C_{2-6}$alkenyl, —$C_{2-6}$alkenyl—O—$C_{1-6}$alkyl, —$C_{2-6}$alkinyl, —$C_{0-5}$alkyl—O—$C_{2-6}$alkinyl, —$C_{2-6}$alkinyl—O—$C_{1-6}$alkyl—, —$C_{6-10}$aryl, —$CO_{0-6}$alkyl—O—$C_{6-10}$,aryl, —$C_{0-6}$alkyl—S(=O)$_{0-2}$—$C_{1-6}$alkyl, —$CO_{0-6}$alkyl—S(=O)$_{-2}$—$C_2$.alkenyl, —$C_{2-6}$alkenyl—S(=O)$_{0-2}$—$C_{1-6}$alkyl, —$C_{0-6}$alkyl—S(=O)$_{0-2}$—$C_{1-6}$alkinyl, —$C_{2-6}$alkinyl—S(=O)$_{0-2}$—$C_{1-6}$alkyl—, $C_{0-6}$alkyl—S(=O)$_{0-2}$—$C_{6-10}$aryl, —$CO_{0-6}$alkyl—COO—$C_{2-6}$alkenyl, —$C_{0-6}$alkyl—COO—$C_{2-6}$-alkinyl, —$C_{2-6}$alkenyl —COO—$C_{1-6}$alkyl, —$C_{2-6}$alkyl—COO—$C_26$alkenyl, —CO6alkyl—COO—$C_26$alkinyl, —$C_26$alkenyl—COO—$C_{,6}$alkyl, —$C_{2-6}$alkinyl—COO—$C_{1-6}$alkyl, —$C_{2-6}$alkenyl—COO—$C_{1-6}$alkyl, —$C_{2-6}$alkinyl—COO—$C_{1-6}$alkyl, and a three to ten membered monocyclic or bicyclic heterocyclic ring structure containing 1–4 heteroatoms selected from N, O and S. The alkyl, alkenyl, and alkinyl portions of $R^a$ and $R^b$ may be linear or branched and may be substituted with from 0–6 members independently selected from the group consisting of —I, —F, —Br, —OH, —$NO_2$, —$CF_3$, —CHO, —$NH_2$ and —COOH. $R^a$ and $R^b$ may also be taken together or with a carbon atom having a free hydrogen to form an intracyclic bond resulting in a three to ten membered heterocyclic ring having from 1–4 heteroatoms selected from N, O and S. R'and R" are each as defined above.

Q of formula I is selected from the group consisting of:

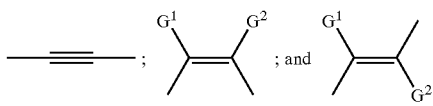

$G^1$ and $G^2$ are each independently a member selected from the group consisting of H, —(CH$_2$),—R$^1$—(J$^1$)$_{0-1}$, —CH=CH—R$^1$—(J$^1$)$_{0-1}$, —C≡C—R$^1$—(J$^1$)$_{0-1}$, (CH$_2$)$_r$—X—(CH$_2$)$_t$—R$^1$—(J$^1$)$_{0-1}$, and —X—(CH$_2$)$_t$—R$^1$—(J$^1$)$_{0-1}$;

J$^1$ may be a hydrogen atom or a substituent that replaces a hydrogen atom on the R$^1$ group as set forth below and the J$^1$ group is absent when a replaceable hydrogen atom is absent from the R$^1$ substituent;

X is selected from the group consisting of —N(R$^2$)—, —P(=O)(—OR$^3$)(—O—), —O—, —C(=O)—, —S—, —SO—, and —SO$_2$—;

r and t are each independently an integer from 0–12, preferably from 0–6;

R$^1$ is a member independently selected from the group consisting of:

(i) a C$_{3-16}$ carbocyclic ring structure which may be substituted by up to 4 R groups where R is defined as above, and a three to ten membered heterocyclic monocyclic or bicyclic heterocyclic ring structure containing 1–4 heteroatoms selected from N, O, and S which may be substituted by up to 4 R groups where R is defined as above;

(ii) H, —SH, —OH, —Cl, —F, —Br, —A, —CN, —NO$_2$, —CHO, —COOH, —NR$^{1'}$R$^{1''}$; and (iii) a substituent member selected from the group consisting of a linear or branched C$_{11-12}$alkyl group, a linear or branched C$_{2-12}$alkenyl group, a linear or branched C$_{2-12}$alkinyl group, and a C$_{3-12}$cycloalkyl group which may have straight or branched chained portions, where for each substituent member:

(a) two hydrogens on the same carbon atom of the alkyl, alkenyl, alkinyl or cycloalkyl substituent member may be replaced with a member selected from the group consisting of =O and =N(R$^{1'''}$);

(b) one or more hydrogens on the alkyl, alkenyl, alkinyl and cycloalkyl substituents members or on the —NH— chain bridging groups may be independently replaced by an R"iv substituent; and (c) one or more hydrogens independently on carbon atom(s) of the alkyl, alkenyl, alkinyl and cycloalkyl substituent members, on the —NH—chain bridging group or on the R$^{1'}$, R$^{1''}$, R$^{1'''}$ or R$^{1iv}$ substituents may form an intracyclic bond to result in a C$_{3-12}$carbocyclic ring structure or result in a three to seven membered heterocyclic ring containing from 1–4 heteroatoms selected from N, O and S; and where each substituent member (iii) may contain from 0 to 4 chain bridging groups independently selected from the group consisting of —NH—, —O—, —S—, —S(=O)—and —S(=O)$_2$—;

R$^{1'}$, R$^{1''}$, R$^{1'''}$ and R$^{1iv}$ are each a member independently selected from the group consisting of H, —(CH$_2$)$_{0-12}$—SH, —(CH$_2$)$_{0-12}$—OH, —(CH$_2$)$_{0-12}$—NH$_2$, —(CH$_2$)$_{0-12}$—Cl, —(CH$_2$)$_{0-12}$—F, —(CH$_2$)$_{0-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{0-12}$—CHO, —C$_{1-12}$alkyl, —C$_{0-12}$alkyl—N(R$^{1b}$)$_{0-1}$—C$_{0-12}$—C$_{0-12}$alkyl, —CH$_{20-12}$—CH=(CH)$_{0-1}$—(CH$_2$)$_{0-12}$(CH$_3$)$_{0-1}$, —O—C$_{1-12}$alkyl—N(R$^{1a}$)(R$^{1b}$)$_{0-1}$—C$_{0-12}$alkyl, —C$_{0-12}$alkyl—)—C$_{1-12}$alkyl, —C$_{0-12}$alkyl—O—C$_{2-12}$alkenyl, —C$_{2-12}$alkenyl—O—C$_{1-12}$-alkyl, —C$_{2-12}$alkinyl, —C$_{0-12}$alkyl—O—C$_{1-6}$-alkinyl, —C$_{0-12}$alkinyl—O—C$_{0-12}$alkyl,—, —C$_{61}$-aryl, —C$_{0-12}$alkyl—O—C$_{60-10}$aryl, —S(=O)$_{0-12}$—$_{1-12}$alkyl—N(R$^{1a}$)(R$^{1b}$)$_{0-1}$—C$_{0-12}$alkyl, —C$_{0-12}$alkyl—S(=O)$_{0-2}$=C$_{1-12}$alkyl, —CO$_{0-12}$alkyl—S(=O)$_{0-2}$—C$_{212}$alkenyl, —C$_{212}$alkenyl—S(=O)$_{0-12}$—C$_{1-12}$alkyl, —C$_{0-1-12}$alkyl—S(=O)$_{0-2}$—C$_{1-6}$alkinyl, —C$_{0-12}$alkinyl—S(=O)$_{0-2}$—C$_{0-12}$alkyl—, —C$_{0-12}$-alkyl—S(=O)$_{0-2}$—C$_{60-10}$aryl, —C$_{0-12}$alkylC$_{60-10}$aryl, —C$_{2-12}$alkenylC$_{6-10}$aryl, —C$_{2-12}$alkinylC$_{60-10}$aryl, —COOH, —C$_{0-12}$alkyl—COOO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{212}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing at least 1–4 heteroatoms selected from N, O and S;

R$^{1a}$ and R$^{1b}$ are each independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —CO$_{0-6}$alkyl—NR$^{1'}$R$^{1''}$, —C$_{0-6}$alkenyl—SH, —CO$_{0-6}$alkenyl—OH, —C$_{0-6}$alkenyl—CHO, —CO$_{0-6}$alkenyl—COOH, —CO$_{0-6}$alkenyl—NR$^{1'}$R$^{1''}$, —C$_{0-6}$alkinyl—SH, —C$_{0-6}$alkinyl—OH, —C$_{0-6}$alkinyl—CHO, —C$_{0-6}$alkinyl—COOH, —CO$_{0-6}$alkinyl—NR$^{1'}$R$^{1''}$, —C$_{1-6}$alkyl, —(CH$_2$)$_{1-6}$—Cl, —(CH$_2$)$_{1-6}$—F, —(CH$_2$)$_{1-6}$—Br, —(CH$_2$)$_{1-6}$—I, —(CF$_2$)$_{1-3}$—(CF$_3$), —(CH$_2$)$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$(CH$_2$)$_{0-4}$(CH$_3$)$_{0-1}$, —C$_{0-5}$alkyl—O—C$_{1-6}$alkyl, —C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{6-10}$aryl —C$_{0-6}$alkyl S(=O)$_{0-2}$—C$_{1-6}$alkyl, —CO$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$—C$_{16}$alkinyl, —C$_{2-6}$alkinyl—S(=O)$_{0-2}$—C$_{1-6}$alkyl—, —C$_{0-6}$alkyl—S(=O)$_{0-2}$—C$_{6-10}$aryl, —C$_{0-6}$alkylC$_{0-10}$aryl, —C$_{2-6}$alkenylC$_{6-10}$aryl —C$_{2-6}$alkinylC$_{0-10}$aryl, —C$_{0-6}$alkyl—COO—C$_{1-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{1-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of R$^{1a}$and R$^{1b}$ may be linear or branched and may be substituted with from 0–6 members independently selected from the group consisting of—I, —F, —Br, —OH, —NO$_2$, —CF$_3$, —CHO, —NH$_2$ and —COOH, where R$^{1'}$ and R$^{1''}$ are each as described above. R$^{1a}$ and R$^{1b}$ may be taken together or with a carbon atom having a free hydrogen to form an intracyclic bond resulting in a three to ten membered heterocyclic ring having from 1–4 heteroatoms selected from N, O and S;

R$^2$ is selected from the group consisting of H, —CN, —C$_{0-6}$alkyl—SH, —C$_{0-1}$alkyl—OH, —C$_{0-6}$alkyl—CHO, —C$_{0-6}$alkyl—COOH, —C$_{0-6}$alkyl—NR$^{2'}$R$^{2''}$, —C$_{0-6}$alkenyl—SH, —C$_{0-6}$alkenyl—OH, —C$_{0-6}$alkenyl—CHO, —C$_{0-6}$alkenyl—COOH, —C$_{0-6}$alkenyl—NR$^{2'}$R$^{2''}$, —C$_{0-6}$alkinyl—SH, —C$_{0-6}$alkinyl—OH, —C$_{0-6}$alkinyl—CHO, —C$_{0-6}$alkinyl—COOH, —C$_{0-6}$alkinyl—NR$^{2'}$R$^{2''}$, —C$_{1-6}$alkyl, —(CH$_2$)$_{1-6}$—Cl, —(CH$_2$)$_{1-6}$—F, —(CH$_2$)$_{1-6}$—

11

Br, —(CH$_2$)$_{1-6}$—I, —(CF$_2$)$_{1-3}$—(CF$_3$), —(CH$_2$)$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$—(CH$_2$)$_{0-4}$(CH$_3$)$_{0-1}$, —CO$_{0-5}$alkyl—O—C$_{1-6}$alkyl, —C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{6-10}$aryl, —C$_{0-4}$alkyl—O—C$_{60-10}$aryl, —C$_{0-6}$alkyl—S(=O)$_{0-2}$—C$_{1-6}$alkyl, —C$_{0-6}$alkyl—S(=O)$_{0-2}$C$_{2-6}$alkenyl, —C$_{2-6}$alkenyl—S(=O)$_{0-2}$—C$_{1-6}$alkyl, —C$_{0-6}$alkyl—S(=O)$_{0-2}$—C$_{1-6}$alkinyl, —C$_{2-6}$alkinyl—S(=O)$_{0-2}$—C$_{1-6}$alkyl—, —C$_{0-6}$alkyl—S(=O)$_{6-10}$aryl, —C$_{0-6}$alkyl, —C$_{6-10}$aryl, —C$_{2-6}$alkenylC$_{6-10}$aryl, —C$_{2-6}$alkinylC$_{6-10}$aryl, —C$_{0-6}$alkyl—COO—C$_{1-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{2-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of R$^2$ may be linear or branched and may be substituted with from 0–6 members independently selected from the group consisting of—I, —F, —Br, —OH, —NO$_2$, —CF$_3$, —CHO, —NH2 and —COOH. R$^2$ may be taken together with a carbon atom having a free hydrogen may form an intracyclic bond resulting in a three to ten membered heterocyclic ring having from 1–4 heteroatoms selected from N, O and S;

R$^{2'}$ and R$^{2''}$ are each a member independently selected from the group consisting of H, —(CH$_2$)$_{1-12}$—SH, —(CH$_2$)$_{1-12}$—OH, —(CH$_2$)$_{0-12}$—NH$_2$, —(CH$_2$)$_{0-12}$—Cl, —(CH$_2$)$_{0-12}$—F, —(CH$_2$)$_{0-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{0-12}$—CHO, —C$_{1-12}$alkyl, —C$_{0-12}$alkyl—N(R$^{2a}$)(R$^{2b}$)$_{0-1}$—C$_{0-12}$alkyl, —(CH$_2$)$_{0-12}$—CH=(CH)$_{0-1}$—,(CH$_2$)$_{1-12}$(CH$_3$)$_{0-1}$, —O—C$_{1-12}$alkyl—N(R$^{2a}$)(R$^{2b}$)$_{0-2}$C$_{0-12}$alkyl —C$_{0-12}$alkyl—O—C$_{1-12}$alkyl, —C$_{0-12}$alkyl—O—C$_{2-12}$alkenyl, —C$_{2-12}$alkenyl—O—C$_{1-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{61-}$aryl, S(=O)$_{0-2}$—C$_{1-12}$alkyl—N(R$^{2a}$)(R$^{2b}$)$_{0-1}$—C$_{0-12}$alkyl, —C$_{0-12}$alkyl—S(=O)$_{0-2}$—C$_{1-12}$alkyl, —C$_{0-12}$alkyl—S(=O)$_{0-2}$—C$_{2-12}$alkenyl, —C$_{212}$—S(=O)$_{0-2}$—C$_{1-12}$alkyl, —C$_{0-12}$alkyl—S(=O)$_{0-2}$—C$_{1-6}$-alkinyl, —CO$_{0-12}$alkinyl—S(=O)$_{0-2}$—C$_{0-12}$alkyl—, —CO$_{0-12}$alkyl—S(=O)$_{0-2}$—C$_{6-10}$aryl, —C$_{0-12}$alkylC$_{0-12}$aryl, —C$_{2-12}$alkenylC$_{6-10}$aryl, —C$_{2-12}$alkinylC$_{6-10}$aryl, —COOH, —CO$_{0-12}$alkyl—COO—C$_{1-12}$alkyl, —CO$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{61-}$aryl monocyclic or bicyclic ring structure, and a three to ten membered heterocyclic monocyclic or bicyclic heterocyclic ring structure containing 1–4 heteroatoms selected from N, O and S;

R$^{2a}$ and R$^{2b}$ are each independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkyl—NR$^{2'}$R$^{2''}$, —C$_{0-6}$alkenyl—SH, —C$_{0-6}$alkenyl—OH, —C$_{0-6}$alkenyl—CHO, —C$_{0-6}$alkenyl—COOH, —C$_{0-6}$alkenyl—NR$^{2'}$R$^{2''}$, —C$_{0-6}$alkinyl—SH, —C$_{0-6}$alkinyl—OH, —C$_{0-6}$alkinyl—CHO, —C$_{0-6}$alkinyl—COOH, —C$_{0-6}$alkinyl—NR$^{2'}$R$^{2''}$, —C$_{1-6}$alkyl, —(CH$_2$)$_{1-6}$—Cl, —(CH$_2$)$_{1-6}$—F, —(CH$_2$)$_{1-6}$—Br, —(CH$_2$)$_{1-6}$—I, —(CF$_2$)$_{1-3}$—(CF$_3$), —(CH$_2$)$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$—(CH$_2$)$_{0-4}$(CH$_3$)$_{0-1}$, —, —C$_{0-5}$alkyl—O—C$_{1-6}$alkyl,

12

—C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{6-10}$,C$_{0-4}$-aryl, —C$_{0-4}$alkyl—O—C$_{6-10}$aryl, —C$_{0-6}$alkyl—S(=O)$_{0-2}$—C$_{1-6}$alkyl, —C$_{0-6}$alkyl—S(=)$_{0-2}$—C$_{2-6}$alkenyl, —C$_{2-6}$alkenyl—S(=O)$_{0-2}$, —C$_{0-6}$alkyl, —S(=O)$_{0-2}$C$_{1-6}$alkinyl, —C$_{2-6}$alkinyl—S(=O)$_{0-2}$—C$_{1-6}$alkyl—, —C$_{0-6}$alkyl —S(=O)$_{0-2}$—C$_{6-10}$aryl, —C$_{0-6}$alkyl$_{60-10}$aryl, —C$_{2-6}$alkenylC$_{6-10}$aryl, —C$_{2-6}$alkinylC$_{6-10}$aryl, —C$_{0-6}$alkyl—COO—C$_{1-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{2-6}$alkyl, —C$_{2-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of R$^{2a}$ and R$^{2b}$ may be linear or branched and may be substituted with from 0–6 members independently selected from the group consisting of—I, —F, —Br, —OH, —NO$_2$, —CF$_3$, —CHO, —NH$_2$ and —COOH, where R$^{2'}$ and R$^{2''}$ are each as described above. R$^{2a}$ and R$^{2b}$ may be taken together or with a carbon atom having a free hydrogen to form an intracyclic bond resulting in a three to ten membered heterocyclic ring having from 1–4 heteroatoms selected from N, O and S;

R$^3$ is selected from the group consisting of:

(i) H, —CHO, —COOH; and (ii) a substituent member selected from the group consisting of a linear or branched C$_{1-12}$alkyl group, a linear or branched C$_{2-12}$alkenyl group, a linear or branched C$_{2-12}$alkinyl group, and a C$_{3-12}$cycloalkyl group which may have straight or branched chained portions, where for each substituent member:

(a) two hydrogens on the same carbon atom of the alkyl, alkenyl, alkinyl or cycloalkyl substituent member may be replaced with a member selected from the group consisting of =O and =N(R$^{3b}$);

(b) one or more hydrogens on the alkyl, alkenyl, allcinyl and cycloalkyl substituents members or on the —NH— chain bridging groups may be independently replaced by an R$^{3''}$ substituent; and (c) one or more hydrogens independently on carbon atom(s) of the alkyl, alkenyl, alkinyl and cycloalkyl substituent members, on the —NH— chain bridging group or on the R$^{3'}$ or R$^{3''}$ substituents may form an intracyclic bond to result in a C$_{3-12}$carbocyclic ring structure or result in a three to seven membered heterocyclic ring containing from 1–4 heteroatoms selected from N, O and S; and where each substituent member (ii) may further contain O to 4 chain bridging groups independently selected from the group consisting of —NH—, —O—, —S—, —S(=O)—and —S(=O)$_2$—;

R$^{3'}$ and R$^{3''}$ are each a member independently selected from the group consisting of H, —(CH$_2$)$_{0-12}$—SH, —(CH$_2$)$_{0-12}$—OH, —(CH$_2$)$_{0-12}$—NH$_2$, —(CH$_2$)$_{0-12}$—Cl, —(CH$_2$)$_{0-12}$—F, —(CH$_2$)$_{0-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{0-12}$—CHO, —C$_{1-12}$alkyl, —C$_{0-12}$alkyl—N(R$^{3a}$)(R$^{3b}$)$_{0-1}$—C$_{0-12}$alkyl, —(CH$_2$)$_{0-12}$—CH=(CH)$_{0-1}$—(CH$_2$)$_{0-12}$(CH$_3$)$_{0-1}$—O—C$_{1-12}$alkyl—N(R$^{3a}$)(R$^{3b}$)$_{0-1}$—C$_{0-12}$alkyl, —CO$_{0-12}$alkyl—O—C$_{1-12}$alkyl, —C$_{0-12}$alkyl—O—C$_{2-12}$alkenyl, —C$_{2-12}$alkenyl—O—C$_{1-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—C—C$_{6-10}$-aryl, S(=O)$_{0-2}$—C$_{1-12}$alkyl,N(R$^{3a}$)(R$^{3b}$)$_{0-1}$—C$_{0-12}$alkyl, —C$_{0-12}$alkyl—S(=O)$_{0-2}$C$_{1-12}$alkyl, —CO$_{0-12}$alkyl—S(=O)$_{0-2}$—C$_{2-12}$alkenyl, —C$_{2-12}$alkenyl—S(=O)$_{0-12}$—C$_{1-12}$alkyl, —C$_{0-12}$alkyl—S(=o)$_{0-2}$—C$_{1-6}$alkinyl, —Cl$_{0-12}$alkinyl—S(=O)$_{0-2}$—Cl$_{1-12}$alkyl—, —C$_{0-12}$alkyl—S(=O)$_{0-2}$—C$_{1-6}$aryl, —C$_{0-12}$alkylC$_{6-10}$aryl, —C$_{2-12}$alkenylC$_{60-10}$aryl, —C$_{2-12}$alkinylC$_{6-10}$aryl, —COOH, —C$_{0-12}$alkyl—COO—C$_{1-2}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-2}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S;

$R^{3a}$ and $R^{3b}$ are each independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkyl—NR$^{3'''}$R$^{4iv}$, —C$_{0-6}$alkenyl—SH, —C$_{0-6}$alkenyl—OH, —C$_{0-6}$alkenyl—CHO, —C$_{0-6}$alkenyl—COOH, —C$_{0-6}$alkenyl—NR$^{3'''}$R$^{3iv}$, —C$_{0-6}$alkinyl—SH, —C$_{0-6}$alkinyl—OH, —C$_{0-6}$alkinyl—CHO, —C$_{0-6}$alkinyl—COOH, —C$_{0-6}$alkinyl—NR$^{3'''}$R$^{3iv}$, —C$_{0-6}$alkyl, —(CH$_2$)$_{1-6}$—Cl, —(CH$_2$)$_{1-6}$—F, —(CH$_2$)$_{1-6}$—Br, —(CH$_2$)$_{1-6}$—I, —(CF$_2$)$_{1-3}$—(CF$_3$), —(CH$_2$)$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$—(CH$_2$)$_{0-4}$(CH$_3$)$_{0-1}$, —C$_{0-5}$alkyl—O—C$_{1-6}$alkyl, —C$_{0-5}$alkyl—O—C$_{2-6}$alkenyl, —C$_{2-6}$alkenyl—O—C$_{,1-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{0-4}$aryl, —C$_{0-6}$alkyl—O—C$_{6-10}$aryl, —C$_{0-6}$alkyl—S(=O)$_{0-2}$—C$_{1-6}$alkyl, —C$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$—C$_{1-6}$alkinyl, —C$_{2-6}$alkinyl—S(=O)$_{0-2}$—C$_{1-6}$alkyl—, —C$_{0-6}$alkyl—S(=O)$_{0-2}$—C$_{0-6}$aryll —C$_{0-6}$alkylC$_{60-10}$aryl, —C$_{2-6}$alkenylC$_{6-10}$aryl, —C$_{2-6}$alkinylC$_{6-10}$aryl, —C$_{0-6}$alkyl—COO—C$_{1-6}$alkyl, —C$_0$alkyl—COO—C$_{2-6}$alkenyl, —C$_{0-6}$alkyl—COO—C$_{2-6}$allkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{2-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of $R^{3a}$ and $R^{3b}$ may be linear or branched and may be substituted with from 0–6 members independently selected from the group consisting of—I, —F, —Br, —OH, —NO$_2$, —CF$_3$, —CHO, —NH2 and —COOH. $R^{3a}$ and $R^{3b}$ may be taken together or with a carbon atom having a free hydrogen to form an intracyclic bond resulting in a three to ten membered heterocyclic ring having from 1–4 heteroatoms selected from N, O and S;

$R^{3'''}$ and $R^{3iv}$ are each a member independently selected from the group consisting of H, —(CH$_2$)$_{0-12}$—SH, —(CH$_2$)$_{0-12}$—OH, —(CH$_2$)$_{0-12}$—NH$_2$, —(CH$_2$)$_{0-12}$—Cl, —(CH$_2$)$_{0-12}$—F, —(CH$_2$)$_{0-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{1-12}$—CHO, —C$_{1-12}$alkyl, —C$_{0-12}$alkylN(R$^{3a}$)(R$^{3b}$)$_{0-1}$—C$_{0-12}$alkyl, —(CH$_2$)$_{0-12}$—CH=(CH)$_{0-1}$—(CH$_2$)$_{0-12}$(CH$_3$)$_{0-1}$, —O—C$_{1-12}$alkylN(R$^{3a}$)(R$^{3b}$)$_{0-1}$—C$_{0-12}$alkyl, —C$_{0-12}$alkyl—O—C$_{1-12}$alkyl, —CO$_{0-12}$alkyl—O—C$_{2-12}$alkenyl, —C$_{2-12}$alkenyl—O—C$_{1-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{6-10}$aryl, S(=O)$_{0-2}$—alkyl—N(R$^{3a}$)(R$^{3b}$)$_{0-1}$—C$_{0-12}$alkyl, —C$_{0-12}$alkyl—S(=O)$_{0-s}$—C$_{1-12}$alkyl, $_2$—C$_{1-12}$alkyl, —CO$_{0-12}$alkyl—S(=O)$_{0-2}$—C$_{2-12}$alkenyl, —C$_{2-12}$alkenyl—S(=O)$_{0-2}$—C$_{1-12}$alkyl, —C$_{0-12}$alkyl—S(=o)$_{0-2}$—C$_{1-6}$-alkinyl, —C$_{0-12}$alkinyl—S(=O)$_{0-12}$—C$_{0-12}$alkyl—, —C$_{0-12}$alkyl—S(=O)$_{0-2}$—C$_{6-10}$aryl, —C$_{0-12}$alkylC$_{6-10}$aryl, —C$_{2-12}$alkenylC$_{6-10}$aryl, —C$_{2-12}$alkinylC$_{6-10}$aryl, —COOH, —C$_{0-12}$alkyl—COO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S, where $R^{3a}$ and $R^{3b}$ are each as described above.

Alternatively, when at least one of $G^1$ and $G^2$ of Q of formula I is selected from the group consisting of —(CH$_2$)$_r$—R$^1$—(J$^1$)$_{0-1}$ and —CH=CH—R$^1$—(J$^1$)$_{0-1}$ then $G^1$ and $G^2$ may be taken together to form a non-aryl carbocyclic ring which may be substituted by $R^1$ or both $R^1$ and $J^1$, whereupon two or more $R^1$ and $J^1$ groups taken together with the atom to which they are each attached may form a further ring with the non-aryl carbocyclic structure including a spiro ring structure, where r, $R^1$, and $J^1$ are each as described above.

$G^1$ of Q of formula I may be taken together with E to form a monocyclic or bicyclic ring structure having from 3 to 10 atoms in the ring structure wherein such ring structures may be independently substituted by up to 4 $R^1$ substituents or collectively by up to 4 $R^1$ and $J^1$ substituents, each as described above. $G^2$ of Q of formula I may be taken together with either or both of Z and A, each as described below, to independently form a monocyclic or bicyclic ring structure having from 3 to 10 atoms in the ring structure wherein such ring structures may be independently substituted by up to 4 $R^1$ substituents or collectively by up to 4 $R^1$ and $J^1$ substituents, each as described above.

$J^1$, when present, is a member independently selected from the group consisting of: H, —CN, —NR$^9$R$^{10}$,

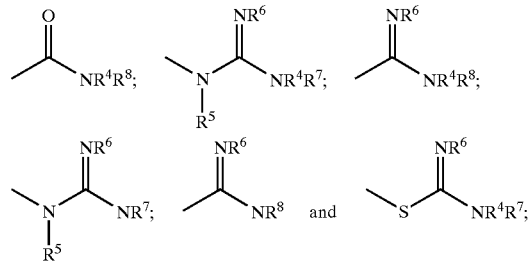

where $R^4$, $R^5$, $R^6$, $R^9$ and $R^{10}$ are independently selected from the group consisting of H, —(CH$_2$)$_{(0-12)}$—SH, —(CH$_2$)$_{0-12}$—OH, —(CH$_2$)$_{0-12}$—NH$_2$, —(CH$_2$)$_{0-12}$—Cl, —(CH$_2$)$_{0-12}$—F, —(CH$_2$)$_{0-12}$—Br, —(CH$_2$)$_{0-12}$—I, (CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$—(CH$_2$)$_{0-12}$—CHO, —C$_{1-12}$alkyl, C$_{0-12}$alkly—N(R$^{a'}$)(R$^{b'}$)$_{0-1}$—C$_{0-12}$alkyl, —(CH$_2$)$_{0-12}$—CH=(CH)$_{0-1}$—(CH$_2$)$_{0-12}$(CH$_3$)$_{0-1}$, —C$_{1-12}$alkylN(R$^{a'}$)(R$^{b'}$)$_{0-2}$—C$_{0-12}$alkyl, —C$_{0-12}$alkyl—O—C$_{1-12}$alklyl, —C$_{0-12}$alkyl—O—C$_{2-12}$alkenyl, —C$_{2-12}$alkenyl—O—C$_{1-12}$alklyl, —C$_{2-12}$alkinyl, —C$_{0-12}$alkyl—O—C$_{1-6}$alkinyl, —C$_{0-12}$alkinyl—O—C$_{0-12}$alkyl—, —C$_{60-10}$-aryl, —C$_{0-12}$alkyl, —O—C$_{60-10}$aryl, —S(=O)$_{0-2}$—C$_{1-12}$alkyl, —C$_{2-12}$alkenyl—S(=O)0—Cl$_{12}$a'kYl, —CO$_{12}$alkyl—S(=O)$_{0-12}$—C$_6$alkinyl, —C(I$_{12}$alkinyl—S(=O)0—C$_{0-12}$alkyl—, —COi$_2$alkyl—S(=O)$_{02}$—C$_{10}$arYl, —C$_{0-12}$alkylC6loaryll —C$_{2-12}$alkenYlC6$_{10}$arYl, —C$_{2-12}$alkinylC$_{,..}$aryl, —COOH, —C$_{0-12}$aalkyl—COO—C$_{1-12}$alkyl—C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenYl—COO—C$_{1-12}$alkly —C$_{2-12}$alkinyl—COO—C$_{1-12}$alklyl, —C$_{6-10}$loaryl monocyclic or bicyclic ring structure, and a three to ten membered heterocyclic monocyclic or bicyclic heterocyclic ring structure containing 1–4 heteroatoms selected from N, O and S;

$R^{a'}$ and $R^{b'}$ are each independently selected from the group consisting of H, —CN, —$C_{0-6}$alklyl—SH, —$C_{0-6}$alkyl—OH, —$C_{0-6}$alkyl—CHO, —$C_{0-6}$alkyl—COOH, —$C_{0-6}$alkyl—N $R^{c'}$ $R^{d'}$ $C_{0-6}$alkenyl—SH, —$C_{0-6}$—OH, —$C_{0-6}$alkenyl—CHO, —$C_{0-6}$—COOH, —$C_{0-6}$alkenyl—N $R^{c'}R^{d'}$ —$C_{0-6}$alkinyl—SH, —$C_{0-6}$alkinyl—OH, —$C_{0-6}$alkinyl—CHO, —$C_{0-6}$alkinyl—COOH, —$C_{0-6}$alkinyl—N $R^{c'}R^{d'}$, —$C_{1-6}$alkyl, —$(CH_2)_{1-6}$—Cl, —$(CH_2)_{1-6}$—F, —$(CH_2)_{1-6}$—Br, —$(CH_2)_{1-6}$—I, —$(CF_2)_{1-3}$—$(CF_3)$, —$(CH_2)_{1-6}$—$(CF_3)$, —$(CH_2)_{1-6}$CN, —$(CH_2)_{0-6}$—$NO_2$, —$C_{1-6}$alkyl, —$(CH_2)_{0-4}$—CH=$(CH)_{0-1}$—$(CH_2)_{0-4}(CH_3)_{0-1}$, —$C_{0-5}$alkyl—O—$C_{1-6}$alkyl, —$C_{0-5}$alkyl—O—$C_{2-6}$alkenyl, —$C_{2-6}$alkenyl—O—$C_{1-6}$alkyl, —$C_{2-6}$alkinyl, —$C_{0-5}$alkyl—O—$C_{2-6}$alkinyl, —$C_{2-6}$alkinyl—O—$C_{1-6}$alkyl—, —$C_{6-10}$aryl, —$C_{0-4}$alkyl—O—$C_{60-10}$aryl, —$C_{0-6}$alkyl—S$(=O)_{0-2}$—$C_{1-6}$alkyl, —$C_{0-6}$alkyl—S$(=O)_{0-2}$—$C_{2-6}$alkenyl, —$C_{2-6}$alkenyl—S$(=O)_{0-2}$—$C_{1-6}$alkyl, —$C_{0-6}$alkyl—S$(=O)_{0-2}$—$C_{1-6}$alkinyl, —$C_{2-6}$alkinyl—S$(=O)_{0-2}$—$C_{1-6}$alkyl—, —$C_{0-6}$alkyl—S$(=O)_{0-2}$—$C_{6-10}$aryl, —$C_{0-6}$alkyIC$_{6-10}$aryl, —$C_{2-6}$alkenylC$_{6-10}$aryl, —$C_{2-6}$alkinyIC$_{6-10}$aryl, —$C_{0-6}$alkyl—COO—$C_{1-6}$alkyl, —$C_{1-6}$alkyl—COO—$C_{2-6}$alkenyl, —$C_{0-6}$alkyl—COO—$C_{2-6}$alkinyl, —$C_{2-6}$alkenyl—COO—$C_{1-6}$alkyl, —$C_{2-6}$alkinyl—COO—$C_{1-6}$alkyl, —$C_{2-6}$alkenyl—COO—$C_{1-6}$alkyl, —$C_{2-6}$alkinyl—COO—$C_{1-6}$alkyl, and a three to ten membered monocyclic or bicyclic heterocyclic ring structure containing 1–4 heteroatoms selected from N, O and S, where the alkyl, alkenyl, and alkinyl portions of $R^{a'}$ and $R^{b'}$ may be linear or branched and may be substituted with from 0–6 members independently selected from the group consisting of —I, —F, —Br, —OH, —$NO_2$, —$CF_3$, —CHO, —NH2 and —COOH. $R^{a'}$ and $R^{b'}$ may be taken together or with a carbon atom having a free hydrogen to form an intracyclic bond resulting in a three to ten membered heterocyclic ring having from 1–4 heteroatoms selected from N, O and S;

$R^{c'}$ and $R^{d'}$ are independently selected from the group consisting of H, $C_{1-6}$alkyl—CHO, $C_{0-6}$alkyl—COOH, $C_{0-6}$alkyl—COCl, $C_{0-6}$alkyl—COI, $C_{0-6}$alkyl—COF, $C_{0-6}$alkyl—COBr, $C_{0-6}$alkyl—COO—$C_{1-6}$alkyl, $C_{1-6}$alkyl—COO—$C_{2-6}$alkenyl, $C_{1-6}$alkyl—COO—$C_{2-6}$alkinyl, $C_{0-6}$alkyl—COO—$C_{0-6}$alkyl—$CF_3$, $C_{1-6}$alkyl—COO—$C_{6-10}$aryl —COOH, $C_{0-6}$alkyl—CN, $C_{1-6}$alkyl—$NO_2$, $C_{1-6}$alkyl—Cl, $C_{1-6}$alkyl—Br, $C_{1-6}$,alkyl—I, $C_{1-6}$alkyl—F, $C_{0-6}$alkyl—$CF_3$, $C_{1-6}$alkyl—$CF_2$—$CF_3$, $C_{1-6}$alkyl—SH, $C_{1-6}$alkyl, $C_{1-6}$alkenyl, $C_{1-6}$alkynyl, $C_{1-6}$alkyloxy, $C_{1-6}$alkenyloxy, $C_{1-6}$alkylthio, $C_{1-6}$alkenylthio, $C_{3-8}$cycloalkyl, $C_{1-6}$aryl, $C_{1-6}$alkylC$_{6-10}$aryl, a three to ten membered heterocyclic monocyclic or bicyclic ring system containing 1–4 heteroatoms selected from N, O and S; and $C_{1-4}$alkylheterocyclic monocyclic or bicyclic ring system having in the ring system 3 to 10 atoms with 1–4 of such atoms being selected from N, O and S;

alternatively, $R^9$ and $R^{10}$ taken together can form a five to ten membered heterocyclic monocyclic or bicyclic ring system containing 1–4 heteroatoms selected from N, O and S;

$R^7$ and $R^8$ are each independently selected from the group consisting of H, —$(CH_2)_{0-12}$—SH, —$(CH_2)_{0-12}$—OH, —$(CH_2)_{0-12}$—$NH_2$, —$(CH_2)_{0-12}$—Cl —$(CH_2)_{0-12}$—F, —$(CH_2)_{0-12}$—Br, —$(CH_2)_{0-12}$—I, —$(CF_2)_{1-5}$—$(CF_3)$, —$(CH_2)_{0-12}$—$(CF_3)$, —$(CH_2)_{0-12}$—CN, —$(CH_2)_{0-12}$$NO_2$—$(CH_2)_{0-12}$—CHO, —$C_{1-12}$alkyl, —$C_{0-12}$alkyl—N$(R^{a'})(R^{b'})_{0-1}$——$C_{0-12}$alkyl, —$(CH_2)_{1-12}$—CH=(CH) $_{0-1}$—$(CH_2)_{0-12}(CH_3)_{0-1}$, —$C_{1-12}$alkyl—N$(R^{a'})(R^{b'})_{0-1}C_{0-12}$alkyl, —$C_{0-12}$alkyl—O—$C_{1-12}$alkyl, —$C_{0-12}$alkyl—O—$C_{2-12}$alkenyl, —$C_{2-12}$alkenyl—O—$C_{1-12}$alkyl, —$C_{2-12}$alkinyl, —$C_{0-12}$alkyl—O—$C_{1-6}$alkinyl, —$C_{0-12}$alkinyl—O—$C_{0-12}$alkyl—, —$C_{60-10}$aryl, —$CO_{0-12}$alkyl—O—$C_{6-10}$aryl, —S$(=O)_{0-2}C_{1-12}$alkyl—N$(R^{a'})(R^{b'})_{0-1}$—$C_{0-12}$alkyl, —$C_{0-12}$alkyl, —$C_{0-12}$alkyl—S$(=O)_{0-2}$—$C_{1-12}$alkyl, —$C_{0-12}$alkyl—S$(=O)_{0-2}$—$C_{2-12}$alkenyl, —$C_{2-12}$alkenyl—S$(=O)_{0-2}$—$C_{1-12}$alkyl, —$C_{0-12}$alkyl—S$(=O)_{0-2}$—$C_{1-6}$-alkinyl, —$C_{0-12}$alkinyl—S$(=O)_{0-2}$—$C_{0-12}$alkyl—, —$C_{0-12}$alkyl—S$(=O)_{0-2}$—$C_{6-10}$aryl, —$C_{0-12}$alkylC$_{6-10}$aryl, —$C_{2-12}$alkenylC$_{6-10}$aryl, —$C_{2-12}$alkinylC$_{6-10}$aryl, —COOH, —$C_{0-12}$alkyl—COO—$C_{1-12}$alkyl, —$C_{0-12}$alkyl—COO—$C_{2-12}$alkenyl, —$C_{1-12}$alkyl—COO—$C_{2-12}$alkinyl, —$C_{2-12}$alkenyl—COO—$C_{1-12}$alkyl, —$C_{2-12}$alkinyl—COO—$C_{1-12}$alkyl, —$C_{2-12}$alkenyl—COO—$C_{1-12}$alkyl, —$C_{2-12}$alkinyl—COO—$C_{1-22}$alkyl, —$C_{6-10}$aryl monocyclic or bicyclic ring structure, and a three to ten membered heterocyclic monocyclic or bicyclic heterocyclic ring structure containing 1–4 heteroatoms selected from the group N, O and S, where $R^{a'}$, $R^{b'}$, $R^{c'}$ and $R^{d'}$ are each as described above;

Alternatively, $R^7$ or $R^8$, independently taken with either $R^5$ and $R^6$, can each form a 3 to 10 membered heterocyclic monocyclic or bicyclic ring containing from 1–4 heteroatoms selected from N, O and S. Still further, $R^7$ or R8, independently taken with either $R^5$ and $R^6$, can each form a 3 to 10 membered heterocyclic monocyclic or bicyclic ring containing from 1–4 heteroatoms selected from N, O and S.

D is a member independently selected from the group consisting of H, —CN, —$R^{11}$, —N $R^2R^{13}$,

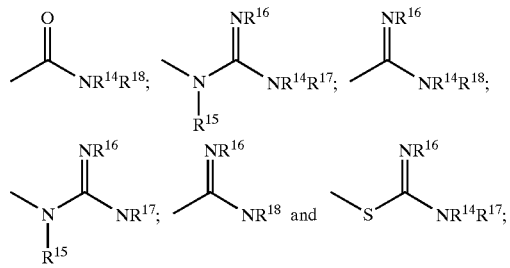

$R^{11}$ is a member independently selected from the group consisting of:

(i) a $C_{3-12}$ carbocyclic ring structure which may be substituted by up to 4 R groups where R is defined as above, and a three to ten membered heterocyclic monocyclic or bicyclic heterocyclic ring structure containing 1–4 heteroatoms which may be substituted by up to 4 R groups where R is defined as above;

(ii) H, —SH, —OH, —Cl, —F, —Br, —I, —CN, —$NO_2$, —CHO, —COOH, —NR$^{11'}$R$^{11'''}$ ; and (iii) a substituent member selected from the group consisting of a linear or branched $C_{1-12}$alkyl group, a linear or branched $C_{2-12}$alkenyl group, a linear or branched $C_{2-12}$alkinyl group, and a $C_{3-12}$cycloalkyl group which may have straight or branched chained portions, where for each substituent member the following types of hydrogen substitutions may be made:

(a) two hydrogens on the same carbon atom of the alkyl, alkenyl, alkinyl or cycloalkyl substituent member may be replaced with a member selected from the group consisting of =O and =N($R^{11'''}$);

(b) one or more hydrogens on the alkyl, alkenyl, alkinyl and cycloalkyl substituents members or on the —NH— chain bridging groups may be independently replaced by an $R^{11iv}$ substituent; and (c) one or more hydrogens independently on carbon atom(s) of the alkyl, alkenyl, alkinyl and cycloalkyl substituent members, on the —NH—chain bridging group or on the $R^{11'}$, $R^{11''}$, $R^{11'''}$ or $R^{11iv}$ substituents may form an intracyclic bond to result in a $C_{3-12}$carbocyclic ring structure or result in a three to seven membered heterocyclic ring containing from 1–4 heteroatoms selected from N, O and S; and where substituent member (iii) may contain from 0 to 4 chain bridging groups independently selected from the group consisting of —NH—, —O—, —S—, —S(=O)—and —S(=O)$_2$—;

$R^{11'}$, $R^{11''}$, $R^{11'''}$ and $R^{11iv}$ are each a member independently selected from the group consisting of H, —(CH$_2$)$_{0-12}$—SH, —(CH$_2$)$_{0-12}$—OH, —(CH$_2$)$_{0-12}$—NH$_2$, —(CH$_2$)$_{0-12}$—Cl, —(CH$_2$)$_{0-12}$—F, —(CH$_2$)$_{1-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{0-12}$—CHO; —C$_{1-12}$alkyl, —C$_{0-12}$alkyl—N(R$^{11a}$)(R$_{11b}$)$_{0-1}$C$_{0-12}$alkyl, —(CH$_2$)$_{0-12}$—CH=(CH)$_{0-1}$—(CH$_2$)$_{0-12}$(CH$_3$)$_{0-1}$, —O—C$_{1-12}$alkyl—N(R$^{11a}$)(R$^{11b}$)$_{0-1}$C$_{0-12}$alkyl, —C$_{0-12}$alkyl—O—C$_{1-12}$alkyl, —C$_{0-12}$alkyl—O—C$_{2-12}$alkenyl, —C$_{2-12}$alkenyl—O—C$_{1-12}$alkyl, —C$_{0-12}$alkinyl, —C$_{0-12}$alkyl—$_{0-6}$alkinyl, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{1-12}$alkyl—N(R$^{11a}$)(R$^{11b}$)$_{0-1}$—C$_{0-12}$alkyl, —C$_{0-12}$alkyl—S(=O)$_{0-2}$—C$_{1-12}$alkyl, —C$_{0-12}$alkyl—S(=O)$_{0-2}$—C$_{2-12}$alkenyl, —C$_{2-12}$alkenyl—S(=O)$_{0-2}$—C$_{1-12}$alkyl, —C$_{0-12}$alkyl—S(=O)$_{0-2}$—C$_{1-6}$alkinyl, —C$_{0-12}$alkinyl—S(=O)$_{0-2}$—C$_{1-1-12}$alkyl—, —C$_{0-12}$alkyl—S(=O)$_{0-2}$—C$_{6-10}$aryl, —C$_{0-12}$alkylC$_{6-10}$aryl, —C$_{2-12}$alkenylC$_{6-10}$aryl, —C$_{2-12}$alkinylC$_{6-10}$aryl, —COOH, —C$_{0-12}$alkyl—COO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1 to4 heteroatoms selected from N, O and S;

$R^{11a}$ and $R^{11b}$ are each independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkyl—NR$^{11'}$R$^{11''}$, —C$_{0-6}$alkenyl—SH, —C$_{0-6}$alkenyl—OH, —C$_{0-6}$alkenyl—CHO, —C$_{0-6}$alkenyl—COOH, —C$_{0-6}$alkenyl—NR$^{11'}$R$^{11''}$, —C$_{0-6}$alkinyl—SH, —C$_{0-6}$alkinyl—OH, —C$_{0-6}$alkinyl—CHO, —C$_{0-6}$alkinyl—COOH, —C$_{0-6}$alkinyl—NR$^{1140}$R$^{11''}$, —C$_{1-6}$alkyl, —(CH$_2$)$_{1-6}$—Cl, —(CH$_2$)$_{1-6}$—F, —(CH$_2$)$_{1-6}$—Br, —(CH$_2$)$_{1-6}$—I, —(CF$_2$)$_{1-3}$—(CF$_3$), —(CH$_2$)$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$—(CH$_2$)$_{0-4}$(CH$_3$)$_{0-1}$, —C$_{0-5}$alkyl—O—C$_{1-6}$alkyl, —C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{6-10}$aryl, —C$_{0-4}$alkyl—O—C$_{06-10}$aryl, —C$_{0-6}$alkyl—S(=O)$_{0-2}$—C$_{1-6}$alkyl, —C$_{0-6}$alkyl—S(=O)$_{0-2}$—C$_{2-6}$,alkenyl, —C$_{2-6}$alkenyl—S(=O)$_{0-2}$—C$_{1-6}$alkyl, —C$_{0-6}$alkyl—S(=O)$_{0-2}$—C$_{1-6}$alkinyl, —C$_{2-6}$alkinyl—S(=O)$_{0-2}$—C$_{1-6}$alkyl—, —C$_{0-6}$alkyl—S(=O)$_{0-2}$—C$_{6-10}$aryl, —C$_{0-6}$alkyl$_{60-10}$aryl, —C$_{2-6}$alkenylC$_{6-10}$aryl, —C$_{2-6}$alkinylC$_{6-10}$aryl, —C$_{0-6}$alkyl—COO—C$_{1-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{2-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of R$^{11a}$ and R$^{11b}$ may be straight or branched chained and may be substituted with from 0–6 members independently selected from the group consisting of —I, —F, —Br, —OH, —NO$_2$, —CF$_3$, —CHO, —NH2 and —COOH. R$^{11a}$ and R$^{11b}$ may be taken together or with a carbon atom having a free hydrogen to form an intracyclic bond resulting in a three to ten membered heterocyclic ring having from 1–4 heteroatoms selected from N, O and S;

$R^{12}$, $R^{13}$, $R^{14}$, $R^{15}$, and $R^{16}$ are independently selected from the group consisting of H, —(CH$_2$)$_{0-12}$—SH, —(CH$_2$)$_{0-12}$—OH, —(CH$_2$)$_{0-12}$NH$_2$, —(CH$_2$)$_{0-12}$—C, —(CH$_2$)$_{0-12}$F, —(CH$_2$)$_{0-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{0-12}$—, CHO, —C$_{1-12}$alkyl, —C$_{0-12}$alkyl—N(R$^{a'}$)(R$^{b'}$)$_{0-2}$—CO$_{0-12}$akyl —(CH$_2$)$_{0-12}$—CH=(CH)$_{0-1}$—(CH$_2$)$_{0-12}$(CH$_3$)$_{0-1}$, —O—C$_{1-12}$alkyl—N(R$^{a'}$)(R$^{b''}$)$_{0-1}$—C$_{0-12}$alkyl, —C$_{0-12}$alkyl—O—C$_{1-12}$alkyl, —C$_{0-12}$alkyl—O—C$_{2-12}$alkenyl, —C$_{2-12}$alkenyl—O—C$_{1-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{0-2}$alkyl—N(R$^{a'}$)(R$^{b'}$)$_{0-1}$I—C$_{0-12}$alkyl, —C$_{0-12}$alkyl—S(=O)$_{0-2}$—C$_{1-12}$alkyl, —C$_{0-12}$alkyl—S(=O)$_{0-2}$—C$_{2-12}$alkenyl, —C$_{2-12}$alkenyl—S(=O)$_{0-2}$—C$_{1-12}$alkyl, —C$_{0-12}$alkyl—S(=O)$_{0-2}$—C$_{1-6}$alkinyl, —C$_{0-12}$alkinyl—S(=O)$_{0-2}$—C$_{0-12}$alkyl—, —C$_{0-12}$alkyl—S(=O)$_{0-12}$—C$_{6-10}$aryl, —C$_{0-12}$alkylC$_{6-10}$aryl, —C$_{2-12}$alkenylC$_{6-10}$aryl, —C$_{2-12}$alkinylC$_{6-10}$aryl, —COOH, —C$_{0-12}$alkyl—COO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S, where Ra', Rb', Rd'and R$^{d'}$ are each as described above; $R^{12}$ and $R^{13}$ taken together can form a five to ten membered heterocyclic monocyclic or bicyclic ring system containing 1144 heteroatoms selected from N, O and S;

$R^{17}$ and $R^{18}$ are each independently selected from the group consisting of H, —(CH$_2$)$_{1-12}$—SH, —(CH$_2$)$_{1-12}$—OH, —(CH$_2$)$_{0-12}$—NH$_2$, —(CH$_2$)$_{0-12}$—Cl, —(CH$_2$)$_{0-12}$—F, —(CH$_2$)$_{0-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{0-12}$—CHO, —C$_{1-12}$alkyl, —C$_{0-12}$alkyl—N(R$^{a'}$)(R$^{b'}$)$_{0-1}$—C$_{0-12}$alkyl, —(CH$_2$)$_{0-12}$—CH=(CH)$_{0-1}$(CH$_2$)$_{0-12}$(CH$_3$)$_{0-1}$, —O—C$_{1-12}$alkyl—N(R$^{a'}$)(R$^{b'}$)$_{0-1}$—C$_{0-12}$alkyl, —C$_{0-12}$alkyl—O—C$_{1-12}$alkyl, —C$_{0-12}$alkyl—O—C$_{2-12}$alkenyl, —C$_{2-12}$alkenyl—O—C$_{1-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{1-12}$alkl—N(R$^{a'}$)(R$^{b'}$)$_{0-1}$—C$_{0-12}$alkyl, —C$_{0-12}$alkyl—S(=O)$_{0-2}$—C$_{1-12}$alkyl, —C$_{0-12}$alkyl—S(=O)$_{0-2}$—C$_{2-12}$alkenyl, —C$_{2-12}$alkenyl—S(=O)$_{0-2}$—C$_{1-12}$alkyl, —C$_{0-12}$alkyl—S(=O)$_{0-2}$—C$_{1-6}$alkinyl, —C$_{0-12\ 12}$alkinyI—S(=O)0.2—CO]$_2$alkyl—, —CO]$_2$alkyl—S(=O)$_{0-2}$—C$_{6-10}$aryl, —C$_{0-12}$alkylC$_{6-10}$aryl, —C$_{2-12}$alkenylC$_{6-10}$aryl, —C$_{2-12}$alkinylC$_{6-10}$aryl, —COOH, —C$_{0-12}$alkyl—COO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S, where R$^{a'}$, R$^{b'}$, R$^{c'}$ and R$^{d'}$ are each as described above;

J is a member independently selected from the group consisting of H, —CN, —R$^{23}$, NR$^{29}$R$^{30}$,

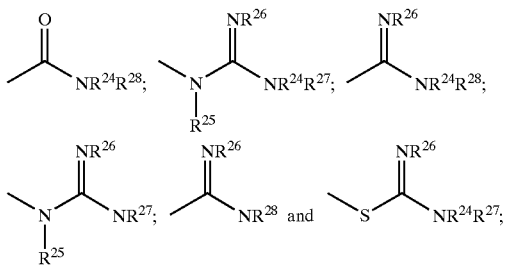

$R^{23}$ is a member independently selected from the group consisting of:

(i) a $C_{3-6}$ carbocyclic ring structure which may be substituted by up to 4 R groups where R is defined as above, and a three to ten membered heterocyclic monocyclic or bicyclic heterocyclic ring structure which may be substituted by up to 4 R groups where R is defined as above;

(ii) H, —SH, —OH, —Cl, —F, —Br, —I, —CN, —NO₂, —CHO, —COOH, —NR²³'R²³''; and (iii) a substituent member selected from the group consisting of a linear or branched $C_{1-12}$alkyl group, a linear or branched $C_{2-12}$alkenyl group, a linear or branched $C_{2-12}$alkinyl group, and a $C_{3-12}$cycloalkyl group which may have straight or branched chained portions, where for each substituent member the following types of hydrogen substitutions may be made:

(a) two hydrogens on the same carbon atom of the alkyl, alkenyl, alkinyl or cycloalkyl substituent member may be replaced with a member selected from the group consisting of =O and =N(R²³''');

(b) one or more hydrogens on the alkyl, alkenyl, alkinyl and cycloalkyl substituents members or on the —NH— chain bridging groups may be independently replaced by an R²³iv substituent; and (c) one or more hydrogens independently on carbon atom(s) of the alkyl, alkenyl, alkinyl and cycloalkyl substituent members, on the —NH— chain bridging group or on the $R^{23'}$, $R^{23''}$, $R^{23'''}$ or $R^{23iv}$ substituents may form an intracyclic bond to result in a $C_{3-12}$ carbocyclic ring structure or result in a three to seven membered heterocyclic ring containing from 1–4 heteroatoms selected from N, O and S; and where a substituent member (iii) may contain 0 to 4 chain bridging groups independently selected from the group consisting of —NH—, —O—, —S—, —S(=O)— and —S(=O)₂—;

$R^{23'}$, $R^{23''}$, $R^{23'''}$ and $R^{23iv}$ are each a member independently selected from the group consisting of H, —(CH₂)₀₋₁₂—SH, —(CH₂)₁₋₁₂—OH, —(CH₂)₁₋₁₂—NH₂, —(CH₂)₀₋₁₂—Cl, —(CH₂)₀₋₁₂—F, —(CH₂)₀₋₁₂—Br, —(CH₂)₀₋₁₂—I, —(CF₂)₁₋₅—(CF₃), —(CH₂)₀₋₁₂—(CF₃), —(CH₂)₀₋₁₂—CN, —(CH₂)₀₋₁₂—NO₂, —(CH₂)₀₋₁₂—CHO, —C₁₋₁₂alkyl, —C₀₋₁₂alkylN(R²³ᵃ)(R²³ᵇ)₀₋₁—C₀₋₁₂alk —(CH₂)₀₋₁₂—CH=(CH)₀₋₁—(CH₂)₀₋₁₂(CH₃)₀₋₁, —O—C₁₋₁₂akylN(R²³ᵃ)(R²³ᵇ)₀₋₁—C₀₋₁₂alkyl, —C₀₋₁₂alkyl—O—C₀₋₁₂alkyl, —C₀₋₁₂alkyl—O—C₂₋₁₂alkenyl, —C₂₋₁₂alkenyl—O—C₁₋₁₂alkyl, —C₂₋₁₂alkinyl, —C₀₋₁₂alkyl—O—C₁₋₆alkinyl, —C₀₋₁₂alkinyl—O—C₀₋₁₂alkyl—, —C₆₋₁₀arYl, —C₀₋₁₂alkyl—O—C₆₋₁₀aryl, —S(=O)₀₋₂—C₁₋₁₂alkyl—N(R²³ᵃ)(R²³ᵇ)₀₋₁—C₀₋₁₂alkyl, —C₀₋₁₂alkyl—C₀₋₁₂alkyl—S(=O)₀₋₂—C₁₋₁₂alkyl, —C₀₋₁₂alkyl—S(=O)₀₋₂—C₂₋₁₂alkenyl, —C₂₋₁₂alkenyl—S(=O)₀₋₂—C₁₋₁₂alkyl, —C₀₋₁₂alkyl—S(=O)₀₋₂—C₁₋₆alkinyl, —C₀₋₂alkinyl—S(=O)₀₋₂—C₀₋₁₂alkyl—, —C₁₋₁₂alkyl—S(=O)₀₋₂—C₆₋₁₀aryl, —C₀₋₁₂alkylC₆₋₁₀aryl, —C₂₋₁₂alkenylC₆₋₁₀aryl, —C₂₋₁₂alkinylC₆₋₁₀aryl, —COOH, —C₀₋₁₂alkyl—COO—C₁₋₁₂alkyl, —C₀₋₁₂alkyl—COO—C₂₋₁₂alkenyl, —C₀₋₁₂alkyl—COO—C₂₋₁₂alkinyl, —C₂₋₁₂alkenyl—COO—C₁₋₁₂alkyl, —C₂₋₁₂alkinyl—COO—C₁₋₁₂alkyl, —C₂₋₁₂alkenyl—COO—C₁₋₁₂alkyl, —C₂₋₁₂alkinyl—COO—C₁₋₁₂alkyl, —C₆₋₁₀aryl monocyclic or bicyclic ring structure, and a three to ten membered heterocyclic monocyclic or bicyclic heterocyclic ring structure containing 1–4 heteroatoms, selected from N, O and S;

$R^{23a}$ and $R^{23b}$ are independently selected from the group consisting of H, —CN, —C₀₋₆alkyl—SH, —C₀₋₆alkyl—OH, —C₀₋₆alkyl—CHO, —C₀₋₆alkyl—COOH, —C₀₋₆alkyl—NR²³'R²³''', —C₀₋₆alkenyl—SH, —C₀₋₆alkenyl—OH, —C₀₋₆alkenyl—CHO, —C₀₋₆alkenyl—COOH, —C₀₋₆alkenyl—NR²³'R²³''', —C₀₋₆alkinyl—SH, —C₀₋₆alkinyl—OH, —C₀₋₆alkinyl—CHO, —C₀₋₆alkinyl—COOH, —C₀₋₆alkinyl—NR²³'R²³''', —C₀₋₆alkyl, —(CH₂)₁₋₆—C₁₋₆—(CH₂)₁₋₆—F, —(CH₂)₁₋₆—Br, —(CH₂)₁₋₆—I, —(CF₂)₁₋₃(CF₃), —(CH₂)₁₋₆—(CF₃), —(CH₂)₁₋₆—CN, —(CH₂)₀₋₆—NO₂, —C₁₋₆alkyl, —(CH₂)₀₋₄—CH=(CH)₀₋₁—(CH₂)₀₋₄(CH₃)₀₋₁, —C₀₋₅alkyl—O—C₁₋₆alkyl, —C₀₋₅alkyl—C₂₋₆alkenyl, —C₂₋₆alkenyl—O—C₁₋₆alkyl, —C₂₋₆alkinyl, —C₀₋₅alkyl—O—C₂₋₆alkinyl, —C₂₋₆alkinyl—O—C₁₋₆alkyl—, —C₆₋₁₀aryl, —C₀₋₄alkyl—O—C₆₋₁₀aryl, —C₀₋₆alkyl—S(=O)₀₋₂—C₁₋₆alkyl, —C₀₋₆alkyl—S(=O)₀₋₂—C₂₋₆alkenyl, —C₂₋₆alkenyl—S(=O)₀₋₂—C₁₋₆alkyl, —C₀₋₆alkyl—S(=O)₀₋₂—C₁₋₆alkinyl, —C₂₋₆alkinyl—S(=O)₀₋₂—C₁₋₆alkyl—, —C₀₋₆alkyl—S(=O)₀₋₂—C₆₋₁₀aryl, —C₀₋₆alkylC₆₋₁₀aryl, —C₂₋₆alkenylC₆₋₁₀aryl, —C₂₋₆alkinylC₆₋₁₀aryl, —C₀₋₆alkyl—COO—C₁₋₆alkyl, —C₀₋₆alkyl—COO—C₂₋₆alkenyl, —C₀₋₆alkyl—COO—C₂₋₆alkinyl, —C₂₋₆alkenyl—COO—C₁₋₆alkyl, —C₂₋₆alkinyl—COO—C₁₋₆alkyl, —C₂₋₆alkenyl—COO—C₁₋₆alkyl, —C₂₋₆alkinyl—COO—C₁₋₆alkyl, and a three to ten membered monocyclic or bicyclic heterocyclic ring structure containing 1–4 heteroatoms selected from N, O and S, where the alkyl, alkenyl, and alkinyl portions of $R^{23a}$ and $R^{23b}$ may be linear or branched and may be substituted with from 0–6 members independently selected from the group consisting of—I, —F, —Br, —OH, —NO₂, —CF₃, —CHO, —NH2 and —COOH, where $R^{23'}$ and $R^{23''}$ are each as defined above. $R^{23a}$ and $R^{23b}$ may also be taken together or with a carbon atom having a free hydrogen to form an intracyclic bond resulting in a three to ten membered heterocyclic ring having from 1–4 heteroatoms selected from N, O and S;

$R^{24}$, $R^{25}$, $R^{26}$, $R^{29}$ and $R^{30}$ are independently selected from the group consisting of H, —(CH₂)₀₋₁₂—SH, —(CH₂)₀₋₁₂—OH, —(CH₂)₀₋₁₂—NH₂, —(CH₂)₀₋₁₂—Cl, —(CH₂)₀₋₁₂—F, —(CH₂)₁₋₁₂—Br, —(CH₂)₀₋₁₂—I, —(CF₂)₁₋₅—(CF₃), —(CH₂)₀₋₁₂—(CF₃), —(CH₂)₀₋₁₂—CN, —(CH₂)₀₋₁₂—NO₂, —(CH₂)₀₋₁₂—CHO, —C₁₋₁₂alkyl, —C₀₋₁₂alkyl—N(Rᵃ')(Rᵇ')₀₋₁—C₀₋₁₂alkyl, —(CH₂)₀₋₁₂—CH=(CH)₀₋₁—(CH₂)₀₋₁₂(CH₃)₀₋₁, —O—C₁₋₁₂alkyl—N(Rᵃ')(Rᵇ')₀₋₁—C₀₋₁₂alkyl —C₀₋₁₂alkyl—O—C₁₋₁₂alkyl, —C₀₋₁₂alkyl—O—C₂₋₁₂alkenyl, —C₂₋₁₂alkenyl—O—C₁₋₁₂alkyl, —C₂₋₁₂alkinyl, —C₀₋₁₂alkyl—O—C₁₋₆alkinyl, —C₁₋₁₂alkinyl—O—C₀₋₁₂alkyl—, —C₆₋₁₀aryl, —C₀₋₁₂alkyl—O—C₆₋₁₀aryl, —S(=O)₀₋₂—C₁₋₁₂alkyl—N(Rᵃ')(Rᵇ')₀₋₁—C₀₋₁₂alkyl, —C₀₋₁₂alkyl—S(=O)₀₋₂—C₁₋₁₂alkyl, —C₀₋₁₂alkyl—S(=O)₀₋₂—C₂₋₁₂alkenyl, —C₂₋₁₂alkenyl—S(=O)₀₋₁₂—C₁₋₁₂alkyl, —C₀₋₁₂alkyl—S(=O)₀₋₂—C₀₋₂alkinyl, —C₀₋₁₂alkinyl—S(=O)₀₋₂—C₀₋₁₂alkyl—, —C₀₋₁₂alkyl—S(=O)₀₋₂—C₆₋₁₀aryl, —C₀₋₁₂alkylC₆₋₁₀aryl, —C₂₋₁₂alkenylC₆₋₁₀aryl, —C₂₋₁₂alkinylC₆₋₁₀aryl, —COOH, —C₀₋₁₂alkyl—COO—C₁₋₁₂alkyl, —C₀₋₁₂alkyl—COO—C₂₋₁₂alkenyl, —C₁₋₁₂alkyl—COO—C₂₋₁₂alkinyl, —C₂₋

$_{12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S, where R$^{a'}$,R$^{b'}$, R$^{c'}$ and R$^{d'}$ are each as described above;

R$^{29}$ and R$^{30}$ taken together can form a five to ten membered heterocyclic monocyclic or bicyclic ring system containing 1–4 heteroatoms selected from N, O and S;

R$^{27}$ and R$^{28}$ are each independently selected from the group consisting of H, —(CH$_2$)$_{0-12}$—SH, —(CH$_2$)$_{0-12}$—OH —(CH$_2$)$_{0-12}$—NH$_2$, —(CH$_2$)$_{0-12}$—Cl —(CH$_2$)$_{0-12}$—F, —(CH$_2$)$_{0-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{0-12}$—CHO, —C$_{1-12}$alkyl, —C$_{0-12}$alkyl—N(R$^{a'}$)(R$^{b'}$)$_{0-1}$—C$_{0-12}$alkyl, —(CH$_2$)$_{0-12}$—CH=(CH)$_{0-1}$—(CH$_2$)$_{0-12}$(CH$_3$)$_{0-1}$, —C$_{1-12}$alyl—N(R$^{a'}$)(R$^{b'}$)$_{0-1}$—CO$_{0-12}$alkyl, —C$_{0-12}$alkyl—O—C$_{1-12}$alkyl, —C$_{0-12}$alkyl—O—C$_{2-12}$alkenyl, —C$_{2-12}$alkenyl—O—C$_{2-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{1-12}$alkyl—N(R$^{a'}$)(R$^{b'}$)$_{0-1}$—CO$_{0-12}$alkyl, —C$_{0-12}$alkyl—S(=O)$_{0-2}$—C$_{1-12}$alkyl, —C$_{0-12}$alkyl—S(=O)$_{0-2}$—C$_{2-12}$alkenyl, —C$_{2-12}$alkenyl—S(=O)$_{2-12}$—C$_{1-12}$alkyl, —C$_{0-12}$alkyl—S(=O)$_{0-2}$—C$_{1-6}$alkinyl, —C$_{0-12}$alkinyl—S(=O)$_{0-2}$—C$_{0-2}$alkyl—, —C$_{0-12}$alkyl—S(=O)$_{0-12}$—C$_{6-10}$aryl, —C$_{0-12}$alkylC$_{6-10}$aryl, —C$_{2-12}$alkenylC$_{6-10}$aryl, —C$_{2-12}$alkinylC$_{6-10}$aryl, —COOH, —C$_{0-12}$alkyl—COO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S, where R$^{a'}$, R$^{b'}$, R$^{c'}$ and R$^{d'}$ are each as described above;

A and T are each independently a ring structure which is selected from the group consisting of a C$_{3-16}$carbocyclic ring structure, a three to ten membered heterocyclic monocyclic or bicyclic ring structure system containing 1–4 heteroatoms selected from N, O and S, and a C$_{1-4}$alkylheterocyclic monocyclic or bicyclic ring system having in the ring system 3 to 10 atoms with 1–4 of such atoms being selected from N, O and S, wherein each of the above carbocyclic and heterocyclic ring structures may be substituted by 0 to 4 R groups which are defined as set forth above in the definition of E, provided that one of A and T can be absent and when both A and T are present they can be directly attached to one another by a direct bond or can be attached indirectly by a bridging group which is bonded to each of A and T. Such a bridging group is selected from the group consisting of —C$_{1-6}$alkylene—, —(CH$_2$)$_{0-6}$—O—(CH$_2$)$_{0-6}$—, N(R$^{34}$)—(CH$_2$)$_{0-6}$—(CH$_2$)$_{0-6}$—C(=N(R$^{34}$))—(CH$_2$)$_{0-6}$—, —(CH$_2$)$_{0-6}$—C(=O)—(CH$_2$)$_{0-6}$—, —(CH$_2$)$_{0-6}$—C(=O)—O—(CH$_2$)$_{0-6}$—(CH$_2$)$_{0-6}$—O—C(=O)—(CH$_2$)$_{0-6}$—, —(CH$_2$)$_{0-6}$—C(=O)—N(R$^{34}$)—(CH$_2$)$_{0-6}$—, —(CH$_2$)$_{0-6}$—N(R$^{34}$)—C(=O)—(CH$_2$)$_0$$_6$—, —(CH$_2$)$_{0-6}$—O—C(=O)—O—(CH$_2$)$_{0-6}$—(CH$_2$)$_{0-6}$—O—C(=O)—N(R$^{34}$)—(CH$_2$)$_{0-6}$—(CH$_2$)$_{0-6}$—N(R$^{34}$)—C(=O)—O—(CH$_2$)$_{0-6}$—, —(CH$_2$)$_{0-6}$—N(R$^{34}$)—C(=O)—N(R$^{35}$)—(CH$_2$)$_{0-6}$—(CH$_2$)$_{0-6}$—S—(CH$_2$)$_{0-6}$—, —(CH$_2$)$_{0-6}$—S(O)—(CH$_2$)$_{0-6}$—(CH$_2$)$_{0-6}$—S(O)$_2$—(CH$_2$)$_{0-6}$—(CH$_2$)$_{0-6}$—S(O)$_2$—N(R$^{34}$)—(CH$_2$)$_{0-6}$—, —(CH$_2$)$_{0-6}$—N(R$^{34}$)—SO$_2$—(CH$_2$)$_{0-6}$—, and —(CH$_2$)$_{0-6}$—N(R$^{34}$)—SO$_2$—N(R$^{35}$)—(CH$_2$)$_{0-6}$—.

R$^{34}$ and R$^{35}$ are each a member independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkyl—NR$^{2'}$R$^{2''}$, —C$_{0-6}$alkenyl—SH, —C$_{0-6}$alkenyl—OH, —C$_{0-6}$alkenyl—CHO, —C$_{0-6}$alkenyl—COOH, —C$_{0-6}$alkenyl—NR$^{34'}$R$^{34''}$, —C$_{0-6}$alkinyl—SH, —C$_{0-6}$alkinyl—OH, —C$_{0-6}$alkinyl—CHO, —C$_{0-6}$alkinyl—COOH, —C$_{0-6}$alkinyl—NR$^{34'}$R$^{34''}$—C$_{1-6}$alkyl, —(CH$_2$)$_{1-6}$—Cl, —(CH$_2$)$_{1-6}$—F, —(CH$_2$)$_{1-6}$—Br, —(CH$_2$)$_{1-6}$—I, —(CF$_2$)$_{1-3}$—(CF$_3$), —(CH$_2$)$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$—(CH$_2$)$_{0-4}$(CH$_3$)$_{0-1}$—C$_{0-5}$alkyl—O—C$_{1-6}$alkyl, —CO$_{0-5}$alkyl—O—C$_{2-6}$alkenyl, —C$_{2-6}$alkenyl—O—C$_{0-6}$alkyl, —C$_{2-6}$alkinyl, —CO$_{0-5}$alkyl—O—C$_{2-6}$alkinyl, —C$_{2-6}$alkinyl—O—C$_{1-6}$alkyl—, —C$_{6-10}$aryl, —C$_{0-4}$alkyl—O—C$_{0-6}$alkyl—O—S(=O)$_{0-2}$—C$_{1-6}$alkyl, —C$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$—C$_{1-6}$alkinyl, —C$_{2-6}$alkinyl—S(=O)$_{0-2}$—C$_{1-6}$alkyl—, —C$_{0-6}$alkyl—S(=O)$_{0-2}$—C$_{6-10}$aryl, —C$_{0-6}$alkylC$_{6-10}$aryl, —C$_{2-6}$alkenylC$_{6-10}$aryl, —C$_{2-6}$alkinylC$_{6-10}$aryl, —C$_{0-6}$alkyl—COO—C$_{1-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{2-6}$alkiyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of each of R$^{34}$ and R$^{35}$ may be linear or branched and may be substituted with from 0–6 members independently selected from the group consisting of —I, —F, —Br, —OH, —NO$_2$, —CF$_3$, —CHO, —NH2 and —COOH. R$^{34}$ and R$^{35}$ may be taken together or with a carbon atom having a free hydrogen to form an intracyclic bond resulting in a three to ten membered heterocyclic ring having from 1–4 heteroatoms selected from N, O and S;

R$^{34'}$ and R$^{34''}$ are each a member independently selected from the group consisting of H, —(CH$_2$)$_{0-12}$—SH, —(CH$_2$)$_{1-12}$—OH, —(CH$_2$)$_{1-12}$—NH$_2$, —(CH$_2$)$_{1-12}$—C$_{1-6}$—(CH$_2$)$_{0-12}$—F, —(CH$_2$)$_{0-12}$—Br, —(CH$_2$)$_{1-12}$—I, —(CF$_2$)$_{1-5}$—(CF$_3$), —(CH$_2$)$_{1-12}$—(CF$_3$), —(CH$_2$)$_{0-12}$—CN, —(CH$_2$)$_{0-12}$—NO$_2$, —(CH$_2$)$_{0-12}$—CHO, —C$_{1-12}$alkyl, —C$_{0-12}$alkylN(R$^{34a}$)(R$^{34b}$)$_{0-1}$—C$_{0-12}$alkyl, —(CH$_2$)$_{0-12}$—CH=(CH)$_{0-1}$—, —(CH$_2$)$_{0-12}$(CH$_3$)$_{0-1}$—O—C$_{0-6}$alkyl—N(R$^{34a}$)(R$^{34b}$)$_{0-1}$—C$_{0-12}$alkyl, —C$_{0-12}$alkyl—O—C$_{1-12}$alkyl, —C$_{0-12}$alkyl—O—C$_{2-12}$alkenyl, —C$_{2-12}$alkenyl—O—C$_{2-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{0-2}$alkyl—N(R$^{34a}$)(R$^{34b}$)$_{0-1}$—C$_{0-12}$alkyl, —C$_{0-12}$alkyl—S(=O)$_{0-2}$—C$_{1-12}$alkyl, —C$_{0-12}$alkyl—S(=O)$_{0-12}$—C$_{2-12}$alkenyl, —C$_{2-12}$alkenyl—S(—O)$_{0-2}$—C$_{1-12}$alkyl, —C$_{0-12}$alkyl—S(=O)$_{0-2}$—C$_{1-6}$alkinyl, —C$_{0-12}$alkinyl—S(=O)$_{0-2}$—C$_{0-12}$alkyl—, —C$_{0-12}$alkyl—S(=O)$_{0-2}$—C$_{6-10}$aryl, —C$_{0-12}$alkylC$_{6-10}$aryl, —C$_{2-12}$alkenylC$_{6-10}$aryl, —C$_{2-12}$alkinylC$_{6-10}$aryl, —COOH, —C$_{0-12}$alkyl—COO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S;

R$^{34a}$ and R$^{34b}$ are each independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkylNR$^{34'}$R$^{34''}$, —C$_{0-6}$alkenyl—SH, —C$_{0-6}$alkenyl—OH, —C$_{0-6}$alkenyl—CHO, —C$_{0-6}$alkenyl—

COOH, —C$_{0-6}$alkenyl—NR$^{34'}$R$^{34''}$, —C$_{0-6}$alkinyl—SH, —C$_{0-6}$alkinyl—OH, —C$_{0-6}$alkinyl—CHO, —C$_{0-6}$alkinyl—COOH, —C$_{0-6}$alkinyl—NR$^{34''}$R$^{34'''}$, —C$_{1-6}$alkyl, —(CH$_2$)$_{1-6}$—C$_{0-6}$—(CH$_2$)$_{1-6}$—F, —(CH$_2$)$_{1-6}$—Br, —(CH$_2$)$_{1-6}$—I —(CF$_2$),$_{-1-6}$—(CF$_3$), —(CH$_2$)$_{1-6}$—(CF$_3$), —(CH$_2$),$_{1-6}$—CN, —(CH$_2$)$_{0-6}$—NO$_2$, —C$_{1-6}$alkyl, —(CH$_2$)$_{0-4}$—CH=(CH)$_{0-1}$—(CH$_2$)$_{0-4}$(CH$_3$)$_{0-1}$—, C$_{0-5}$alkyl—O—C$_{1-6}$alkyl, —C$_{0-5}$alkyl—O—C$_{2-6}$alkenyl, —C$_{2-6}$alkenyl—O—C$_{2-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{6-10}$aryl, —C$_{6-10}$alkyl—O—C$_{6-10}$aryl, C$_{0-6}$alkyl—S(=O)C$_{0-2}$—C$_{1-6}$alkyl, —C$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$—C$_{1-6}$alkinyl, —C$_{2-6}$alkinyl—S(=O)$_{0-2}$—C$_{1-6}$alkyl—, —C$_{0-6}$alkyl—S(=O)$_{0-2}$—C$_{6-10}$aryl, —C$_{0-6}$alkylC$_{6-10}$aryl, —C$_{2-4}$alkenylC$_{6-10}$aryl, —C$_{2-6}$alkinylC$_{6-10}$aryl, —C$_{0-6}$alkyl—COO—C$_{1-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkyinyl—COO—C$_{1-6}$alkyl, —C$_{2-6}$alkenyl—COO—C$_{1-6}$alkyl, —C$_{2-4}$alkinyl—COO—C$_{1-6}$alkyl, and a three to ten membered monocyclic or bicyclic heterocyclic ring structure containing 1–4 heteroatoms selected from N, O and S, where R$^{34''}$ and R$^{34'''}$ are each as described above. The alkyl, alkenyl, and alkinyl portions of R$^{341}$ and R$^{34b}$ may be linear or branched and may be substituted with from 0–6 members independently selected from the group consisting of—I, —F, —Br, —OH, —NO$_2$, —CF$_3$, —CHO, —NH2 and —COOH. R$^{34a}$ and R$^{34b}$ may be taken together or with a carbon atom having a free hydrogen to form an intracyclic bond resulting in a three to ten membered heterocyclic ring having from 1–4 heteroatoms selected from N, O and S.

Z is selected from the group consisting of a bond, —C$_{1-6}$alkylene—, —(CH$_2$)$_{0-6}$—O—(CH$_2$)$_{0-6}$, —(CH$_2$)$_{0-6}$N(R$^{36}$)—(CH$_2$)$_{0-6}$—(CH$_2$)$_{0-6}$—C(=N(R$^{36}$))—(CH$_2$)$_{0-6}$—(CH$_2$)$_{0-6}$—C(=O)—(CH$_2$)$_{0-6}$—C(CH$_2$)$_{0-6}$—C(=O)—O—(CH$_2$)$_{0-6}$—(CH$_2$)$_{0-6-0}$—C(=O)—(CH$_2$)$_{0-6}$—, —(CH$_2$)$_{0-6}$—C(=O)—N(R$^{36}$)—(CH$_2$)$_{0-6}$—(CH$_2$)O—N(R$^{36}$)—C(=O)—(CH$_2$)$_{0-6}$—, —(CH$_2$)$_{0-6}$—C(=O)—O—(CH$_2$)$_{0-6}$—(CH$_2$)$_{0-6}$—C(=O)—N(l$^{36}$)—(CH$_2$)$_{0-6}$—, —(CH$_2$)$_{0-6}$—N(R$^{36}$)—C(=O)—O—(CH$_2$)$_{0-6}$—(CH$_2$)$_{0-6}$—N(R$^{36}$)—C(=O)—(CH$_2$)(R$^{37}$)—(CH$_2$)$_{0-6}$—S—(CH$_2$)$_{0-6}$—, —(CH$_2$)$_{0-6}$—S(O)—(CH$_2$)$_{0-6}$—, —(CH$_2$)$_{0-6}$—S(O)$_2$—(CH$_2$)$_{0-6}$—, —(CH$_2$)$_{0-6}$—S(O)$_2$—N$^{(36)}$—(CH$_2$)—$_{0-6}$—, —(CH$_2$)$_{0-6}$—N(R$^{36}$)—SO$_2$—(CH$_2$)$_{0-6}$—, and —(CH$_2$)$_{0-6}$—N(R$^{36}$)—SO$_2$—N$^{(37)}$—(CH$_2$)$_{0-6}$—; R$^{36}$ and R$^{37}$ are each a member independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkyl—NR$^{36'}$R$^{36''}$, —C$_{0-6}$alkenyl—SH, —C$_{0-6}$alkenyl—OH, —C$_{0-6}$alkenyl—CHO, —C$_{0-6}$alkenyl—COOH, —C$_{1-6}$alkenyl—NR$^{36'}$R$^{36''}$, —C$_{0-6}$alkinyl—SH, —C$_{1-6}$alkinyl—OH, —C$_{0-6}$alkinyl—CHO, —C$_{0-6}$alkinyl—COOH, —C$_{0-6}$alkinyl—NR$^{36'}$R$^{36''}$, —C$_{1-6}$alkyl, —(CH$_2$)$_{1-6}$—C$_{0-6}$Cl, —(CH$_2$)$_{1-6}$—F, —(CH$_2$)$_{1-6}$—Br, —(CH$_2$)$_{1-6}$—Il —(CF$_2$),—$_3$—(CF$_3$), —(CH$_2$)$_{1-6}$—(CF$_3$), —(CH$_2$)$_{1-6}$—CN, —(CH$_2$)$_{0-6}$—NO$_2$, —C$_{0-6}$alkyl, —(CH$_2$)$_{0-4}$—CH=(CH)$_{0-1}$—(CH$_2$)$_{0-4}$(CH$_3$)$_{0-1}$, —C$_{0-5}$alkyl—O—C$_{1-6}$alkyl, —C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{6-10}$aryl, —C$_{0-6}$alkyl—O—C$_{0-6}$aryl, —C$_{0-6}$alkyl—S(=O)$_{0-2}$—C$_{1-6}$alkyl, —C$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$C$_{1-6}$alkinyl, —C$_{2-6}$alkinyl—S(=O)$_{0-2}$—C$_{1-6}$alkyl—, —C$_{0-6}$alkyl—S(=O)l$_{0-2}$—C$_{6-10}$aryl, —C$_{0-6}$alkylC$_{6-10}$aryl, —C$_{2-6}$alkenylC$_{6-10}$aryl, —C$_{2-6}$alkinylC$_{6-10}$aryl, —C$_{0-6}$alkyl—COO—C$_{0-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkenyl—COO—C$_{1-6}$alkyl, —C$_{2-6}$alkenyl—COO—C$_{1-6}$alkyl, —C$_{2-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of each of R$^{36}$ and R$^{37}$ may be linear or branched and may be substituted with from 0–6 members independently selected from the group consisting of —I, —F, —Br, —OH, —NO$_2$, —CF$_3$, —CHO, —NH$_2$ and —COOH. R$^{36}$ and R$^{37}$ may be taken together or with a carbon atom having a free hydrogen to form an intracyclic bond resulting in a three to ten membered heterocyclic ring having from 1–4 heteroatoms selected from N, O and S;

R$^{36'}$ and R$^{36''}$ are each a member independently selected from the group consisting of H, —(CH$_2$)$_{1-12}$—SH, —(CH$_2$)$_{0-12}$—OH, —(CH$_2$)$_{1-12}$—NH$_2$, —(CH$_2$)$_{0-12}$—Cl, —(CH$_2$)$_{0-12}$—F, —(CH$_2$)$_{0-12}$—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{1-12}$—CHO, —C$_{1-12}$alkyl, —C$_{0-12}$alkyl—N(R$^{36a}$)(R$^{36b}$)$_{0-1}$C$_{0-12}$alkyl, —(CH$_2$)$_{0-12}$—CH=(CH)$_{0-1}$—(CH$_2$)$_{0-12}$(CH$_3$)$_{0-1}$, —O—C$_{1-12}$alkyl—N(R$^{36a}$)(R$^{33b}$)$_{0-1}$—C$_{0-12}$alkyl, —C$_{0-12}$alkyl—O—C$_{1-12}$alkyl, —C$_{0-12}$alkyl—O—C$_{2-12}$alkenyl, —C$_{2-12}$alkenyl—O—C$_{1-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{1-12}$alkyl—N(R$^{36a}$)(R$^{33b}$)$_{0-1}$—C$_{0-12}$alkyl, —C$_{0-12}$alkyl—S(=O)$_{0-2}$C$_{1-12}$alkyl, —C$_{0-12}$alkyl—S(=O)$_{0-2}$—C$_{2-12}$alkenyl, —C$_{2-12}$alkenyl—S(=O)$_{0-2}$—C$_{1-12}$alkyl, —C$_{0-12}$alkyl—S(=O)$_{0-2}$—C$_{1-6}$alkinyl, —C$_{0-62}$alkinyl—S(=O)$_{0-2}$—C$_{0-12}$alkyl—, —C$_{1-12}$alkyl—S(=O)$_{0-2}$—C$_{6-10a}$aryl, —C$_{0-12}$alkylC$_{6-10}$aryl, —C$_{2-12}$alkenylC$_{6-10}$aryl, —C$_{2-12}$alkinylC$_{6-10}$aryl, —COOH, —C$_{0-12}$alkyl—COO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S;

R$^{36a}$ and R$^{36b}$ are each independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkyl—NR$^{36'}$R$^{36''}$, —C$_{0-6}$alkenyl—SH, —C$_{0-6}$alkenyl—OH, —C$_{0-6}$alkenyl—CHO, —C$_{0-6}$alkenyl—COOH, —C$_{1-6}$alkenyl—NR$^{36'}$R$^{36''}$,—C$_{0-6}$alkinyl—SH, —C$_{0-6}$alkinyl—OH, —C$_{0-6,}$alkinyl—CHO, —C$_{0-6}$alkinyl—COOH, —C$_{0-6}$alkinyl—NR$^{36'}$R$^{36'''}$, —C$_{1-6}$alkyl, —(CH$_2$)$_{1-6}$—C$_{0-6}$—(CH$_2$)$_{1-6}$—F, —(CH$_2$)$_{1-6}$—Br, —(CH$_2$)$_{1-6}$—I, —(CF$_2$)$_{1-3}$—(CF$_3$), —(CH$_2$)$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$—,—(CH$_2$)$_{0-4}$(CH$_3$)$_{0-1}$—, —C$_{0-5}$alkyl—O—C$_{1-6}$alkyl, —C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{1-6}$allyl—, —C$_{6-10}$aryl, —C$_{0-6}$alkyl—O—C$_{0-6}$aryl, —C$_{0-6}$alkyl—S(=O)$_{0-2}$—C$_{1-6}$alkyl, —C$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$C$_{1-6}$alkinyl, —C$_{2-6}$alkinyl—S(=O)$_{0-2}$—C$_{1-6}$alkyl—, —C$_{0-6}$alkyl—S(=O)$_{0-2}$—C$_{6-10}$aryl, —C$_{0-6}$alkylC$_{6-10}$aryl, —C$_{2-6}$alkenylC$_{6-10}$aryl, —C$_{60-10}$alkinylC$_{6-10}$aryl, —C$_{0-6}$alkyl—COO—C$_{1-6}$alkyl, —C$_{0-6}$alkyl—COO—C$_{2-6}$alkenyl, —C$_{0-6}$alkyl—COO—C$_{2-6}$alkinyl, —C$_{2-4}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{2-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of $R^{36a}$ and $R^{36b}$ may be linear or branched and may be substituted with from 0–6 members independently selected from the group consisting of —I, —F, —Br, —OH, —NO$_2$, —CF$_3$, —CHO, —NH2 and —COOH. $R^{36a}$ and $R^{36b}$ may be taken together or with a carbon atom having a free hydrogen to form an intracyclic bond with a resulting three to ten membered heterocyclic ring having from 1–4 heteroatoms selected from N, O and S.

M is selected from the group consisting of a bond, —C$_{1-6}$alkylene—, —(CH$_2$)$_{0-6}$—(CH$_2$)$_{0-6}$—(CH$_2$)$_{0-6}$—N($^{38}$)—(CH$_2$)$_{0-6}$—, —(CH$_2$)$_{0-6}$—C(=N(R$^{38}$))—(CH$_2$)$_{0-6}$—, —(CH$_2$)$_{0-6}$—C(=O)—(CH$_2$)$_{0-6}$—, —(CH$_2$)$_{0-6}$—C(=O)—O—(CH$_2$)$_{0-6}$—(CH$_2$)$_{0-6}$—O—C(=O)—(CH$_2$)$_{0-6}$—, —(CH$_2$)$_{0-6}$—C(=O)—N($^{38}$)—(CH$_2$)$_{0-6}$—, —(CH$_2$)$_{0-6}$—N(R$^{38}$)—C(=O)—(CH$_2$)$_{0-6}$—(CH$_2$)$_{0-6}$—C(=O)—O—(CH$_2$)$_{0-6}$—(CH$_2$)$_{0-6}$—C(=O)—N(R$^{38}$)—(CH$_2$)$_{0-6}$—, —(CH$_2$)$_{0-6}$—N(R$^{38}$)—C(=O)—O—(CH$_2$)$_{0-6}$—, —(CH$_2$)$_{0-6}$—N(R$^{38}$)—C(=O)—N(R$^{39}$)—(CH$_2$)$_{0-6}$—, —(CH$_2$)$_{0-6}$—S—(CH$_2$)$_{0-1}$—, —(CH$_2$)$_{0-6}$—S(O)—(CH$_2$)$_{0-6}$—S(O)$_2$—(CH$_2$)$_{0-6}$—, —(CH$_2$)$_{0-6}$—S(O)$_2$—N($^{38}$)—(CH$_2$)$_{0-6}$—(CH$_2$)$_{0-6}$—N(R$^{38}$)SO$_2$—(CH$_2$)$_{0-6}$—, and —(CH$_2$)$_{0-6}$—N(R$^{38}$)—SO$_2$—N(R$^{39}$)—(CH$_2$)$_{0-6}$—;

$R^{38}$ and $R^{39}$ are independently a member selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkyl—NR$^{38'}$R$^{38''}$, —C$_{0-6}$alkenyl—SH, —C$_{0-6}$alkenyl—OH, —C$_{0-6}$alkenyl—CHO, —C$_{0-6}$alkenyl—COOH, —C$_{0-6}$alkenyl—NR$^{38'}$R$^{38''}$, —C$_{0-6}$alkinyl—SH, —C$_{0-6}$alkinyl—OH, —C$_{0-6}$alkinyl—CHO, —C$_{0-6}$alkinyl—COOH, —C$_{0-6}$alkinyl—NR$^{38'}$R$^{38''}$, —C$_{1-6}$alkyl, —(CH$_2$)$_{1-6}$—C$_{1-6}$Cl, —(CH$_2$)$_{1-6}$—F, —(CH$_2$)$_{1-6}$—Br, —(CH$_2$)$_{1-6}$I, —$_{1-6}$—(CF$_2$),—$_{1-3}$—(CF$_3$), —(CH$_2$),$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$—,—(CH$_2$)$_{0-4}$(CH$_3$)$_{0-1}$—$_{0-1}$C$_{0-5}$alkyl—O—C$_{1-6}$alkyl, —C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{6-10}$aryl, —C$_{0-4}$alkyl—O—C$_{6-10}$aryl, —C$_{0-6}$alkyl—S(=O)$_{0-2}$—C$_{1-6}$alkyl, —C$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$—C$_{1-6}$alkinyl, —C$_{2-6}$alkinyl—S(=O)$_{0-2}$—C$_{1-6}$alkyl—, —C$_{0-6}$alkyl—S(=O)$_{0-2}$—C$_{6-10}$aryl, —C$_{0-6}$alkylC$_{6-10}$aryl, —C$_{2-6}$alkenylC$_{6-10}$aryl, —C$_{2-6}$alkinylC$_{6-10}$aryl, —C$_{0-6}$alkyl—COO—C$_{0-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{2-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of each of $R^{38}$ and $R^{39}$ may be linear or branched and may be substituted with from 0–6 members independently selected from the group consisting of —I, —F, —Br, —OH, —NO$_2$, —CF$_3$, —CHO, —NH2 and —COOH. $R^{38}$ and $R^{39}$ may be taken together or with a carbon atom having a free hydrogen to form an intracyclic bond resulting in a three to ten membered heterocyclic ring having from 1–4 heteroatoms selected from N, O and S.

$R^{38'}$ and $R^{38''}$ are each a member independently selected from the group consisting of H, —(CH$_2$)$_{0-12}$—SH, —(CH$_2$)$_{1-12}$—OH, —(CH$_2$)$_{1-12}$—NH$_2$, —(CH$_2$)$_{1-12}$—C$_{0-12}$—(CH$_2$)$_{0-12}$—F, —(CH$_2$)$_{0-12}$—Br, —(CH$_2$)$_{0-12}$—I, —(CF$_2$)$_{1-5}$—(CF$_3$), —(CH$_2$)$_{1-12}$—(CF$_3$), —(CH$_2$)$_{0-12}$—CN, —(CH$_2$)$_{0-12}$—NO$_2$, —(CH$_2$)$_{0-12}$—CHO, —C$_{0-12}$alkyl, —C$_{0-12}$alkyl—N(R$^{38a}$)((R$^{38b}$)$_{0-1}$—C$_{0-12}$alkyl, —C$_{0-12}$alkyl—O—C$_{1-12}$alkyl, —C$_{0-12}$alkyl—O—C$_{2-12}$alkenyl, —C$_{2-12}$alkenyl—O—C$_{1-12}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{1-12}$alkyl—N(R$^{33a}$)(R$^{38b}$)$_{0-1}$—C$_{0-12}$alkyl, —C$_{0-12}$alkyl—S(=O)$_{0-2}$—C$_{1-12}$alkyl, —C$_{0-12}$alkyl—S(=O)$_{0-2}$—C$_{2-12}$alkenyl, —C$_{2-12}$alkenyl—S(=O)$_{0-2}$—C$_{1-12}$alkyl, —C$_{0-12}$alkyl—S(=O)$_{0-2}$—C$_{1-6}$alkinyl, —C$_{0-12}$alkinyl—S(=O)$_{0-2}$—C$_{0-12}$alkyl—, —C$_{0-12}$alkyl—S(=O)$_{0-2}$—C$_{6-10}$aryl, —C$_{0-12}$alkylC$_{6-10}$aryl, —C$_{2-12}$alkenylC$_{6-10}$aryl, —C$_{2-12}$alkinylC$_{60-10}$aryl, —COOH, —C$_{0-12}$alkyl—COO—C$_{1-12}$alkyl, —C$_{0-12}$alkyl—COO—C$_{2-12}$alkenyl, —C$_{0-12}$alkyl—COO—C$_{2-12}$alkinyl, —C$_{2-12}$alkenyl—COO—C$_{1-12}$alkyl, —C$_{2-12}$alkinyl—COO—C$_{1-12}$alkyl, —C$_{2-12}$alkenyl—COO—C$_{1-12}$alkyl, —C$_{2-12}$alkinyl—COO—C$_{1-12}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S;

$R^{38a}$ and $R^{38b}$ are each independently selected from the group consisting of H, —CN, —C$_{0-6}$alkyl—SH, —C$_{0-6}$alkyl—OH, —C$_{0-6}$alkyl—CHO, —C$_{0-6}$alkyl—COOH, —C$_{0-6}$alkyl—NR$^{38'}$R$^{38''}$, —C$_{0-6}$alkenyl—SH, —C$_{0-6}$alkenyl—OH, —C$_{0-6}$alkenyl—CHO, —C$_{0-6}$alkenyl—COOH, —C$_{0-6}$alkenyl—NR$^{38'}$R$^{38''}$, —C$_{0-6}$alkinyl—SH, —C$_{0-6}$alkinyl—OH, —C$_{0-6}$alkinyl—CHO, —C$_{1-6}$alkinyl—COOH, —C$_{0-6}$alkinyl—NR$^{38'}$R$^{38''}$, —C$_{1-6}$alkyl, —(CH$_2$)$_{1-6}$—Cl, —(CH$_2$)$_{1-6}$—F, —(CH$_2$)$_{1-6}$—Br, —(CH$_2$)$_{1-6}$—I, —(CF$_2$)$_{1-3}$—(CF$_3$), —(CH$_2$)$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$, —(CH$_2$)$_{0-5}$(CH$_3$)$_{0-1}$—C$_{0-5}$alkyl—O—C$_{1-6}$alkyl, —C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{1-6}$alkyl—, —C$_{6-10}$ aryl, —C$_{0-6}$alkyl—O—C$_{6-10}$aryl, —C$_{0-6}$alkyl—S(=O)$_{0-2}$—C$_{1-6}$alkyl, —C$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$—C$_{1-6}$alkinyl, —C$_{2-6}$alkinyl—S(=O)$_{0-2}$—C$_{1-6}$alkyl—, —C$_{0-6}$alkyl—S(=O)$_{0-2}$—C$_{6-10}$aryl, —C$_{0-6}$alkylC$_{6-10}$aryl, —C$_{2-6}$alkenylC$_{6-10}$aryl, —C$_{2-6}$alkinylC$_{6-10}$aryl, —C$_{0-6}$alkyl—COO—C$_{1-6}$alkyl, —C$_{0-6}$alkyl—COO—C$_{2-4}$alkenyl, —C$_{0-6}$alkyl—COO—C$_{2-6}$alkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{2-6}$alkinyl—COO—C$_{1-6}$alkyl, and a three to ten membered monocyclic or bicyclic heterocyclic ring structure containing 1–4 heteroatoms selected from N, O and S, where the alkyl, alkenyl, and alkinyl portions of $R^{38a}$ and $R^{38b}$ may be linear or branched and may be substituted with from 0–6 members independently selected from the group consisting of —I, —F, —Br, —OH, —NO$_2$, —CF$_3$, —CHO, —NH$_2$ and —COOH. $R^{38}a$ and $R^{38}b$ may be taken together or with a carbon atom having a free hydrogen to form an intracyclic bond resulting in a three to ten membered heterocyclic ring having from 1–4 heteroatoms selected from N, O and S.

According to the invention, a compound of formula I includes all pharmaceutically acceptable isomers, salts, hydrates, solvates and prodrug derivatives thereof.

Preferred compounds of the invention include those compounds of following formulae IIa, IIb, and IIc:

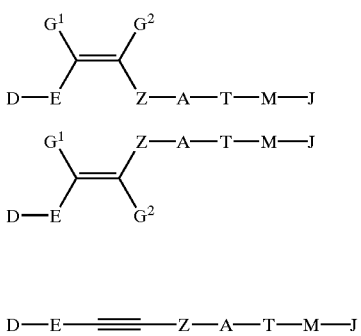

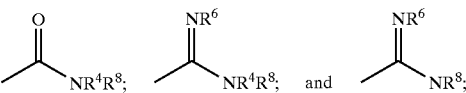

and all pharmaceutically acceptable isomers, salts, hydrates, solvates and prodrug derivatives thereof.

In formulae IIa, IIb, and IIc, D, E, $G^1$, $G^2$, Z, A, T, M, J and their respective substituents are each as described above for formula I. Preferably, for $G^1$ and $G^2$ of formulae IIa and IIb:

X is selected from the group consisting of —N—, —O—, —C(=O)—, —S—, —SO—, and —$SO_2$—;

r and t are each independently an integer from 0–6; and $R^1$ is a member independently selected from the group consisting of H, —OH, halogen, trihalomethyl, —CN, —$NO_2$, $C_{1-6}$alkyl, $C_{3-8}$cycloalkyl, —O—$C_{1-6}$alkyl, $C_{1-6}$alkenyl, —O—$C_{1-6}$alkenyl, $C_{1-6}$alkinyl, —O—$C_{1-6}$alkinyl, $C_{6-10}$aryl, —O—$C_{6-10}$aryl, $C_{1-6}$alkyl$C_{6-10}$aryl, —O—$C_{1-6}$alkyl$C_{6-10}$aryl, —COOH, —COO—$C_{1-6}$alkyl.

More preferably, for compounds of formulae IIa and IIb:

X is selected from the group consisting of —N—, —O—, —C(=O)—, —S—, —SO—, and —SO,—;

r and t are each independently an integer from 0–6;

$R^1$ is a member independently selected from the group consisting of H, —OH, halogen, trihalomethyl, —CN, —$NO_2$, $C_{1-6}$alkyl, $C_{3-8}$cycloalkyl, —O—$C_{1-6}$alkyl, $C_{1-6}$alkenyl, —O—$C_{1-6}$alkenyl, $C_{0-6}$alkinyl, —O—$C_{6-10}$alkinyl, $C_{6-10}$aryl, —O—$C_{1-6}$aryl, $C_{1-6}$alkyl$C_{6-10}$aryl, —O—$C_{1-6}$alkyl$C_{6-10}$aryl, —COOH, —COO—$C_{1-6}$alkyl; and R groups of E, A and T are independently selected from the group consisting of H, —OH, halogen, trihalomethyl, —CN, —$NO_2$, $C_{1-6}$alkyl, $C_{3-8}$cycloalkyl, —O—$C_{1-6}$alkyl, $C_{1-6}$alkenyl, —O—$C_{1-6}$alkenyl, $C_{1-6}$alkinyl, —O—$C_{1-6}$alkinyl, $C_{6-10}$aryl, —O—$C_{6-10}$aryl, $C_{1-6}$alkyl$C_{6-10}$aryl, —O—$C_{1-6}$alkyl$C_{6-10}$aryl, —COOH, —COO—$C_{1-6}$alkyl, wherein 0 to 4 R groups may be present in each of E, A and T, and wherein two R groups independently on either or all of E, A and T may combine to form a methylenedioxy or ethylene dioxy group. More preferably, for compounds of formulae Ia, IIb and IIc, E, A and T are independently selected from the group consisting of phenyl, naphthyl, biphenyl, 2-pyridyl, 3-pyridyl, 4-pyridyl, 1,2-pyrimidyl, 1,3-pyrimidyl, 1,4-pyrimidyl, morpholinyl, thiomorpholinyl, piperidinyl, thiophenyl, oxaxolyl, isoxazolyl, thiazolyl, isothiazolyl, imidazolyl and triazole, where E, A and T independently have 0 to 4 R groups independently selected from the group consisting of H, —OH, halogen, trihalomethyl, —CN, —$NO_2$, $C_{1-6}$alkyl, $C_{3-8}$cycloalkyl, —O—$C_{1-6}$alkyl, $C_{1-6}$alkenyl, —O—$C_{1-6}$alkenyl, $C_{1-6}$alkinyl, —O—$C_{1-6}$alkinyl, $C_{6-10}$aryl, —O—$C_{6-10}$aryl, $C_{1-6}$alkyl$C_{6-10}$aryl, —O—$C_{1-6}$alkyl$C_{6-10}$aryl, —COOH, —COO—$C_{1-6}$alkyl. According to the invention, two R groups taken together may form a methylenedioxy or ethylenedioxy group. Also according to the invention, two R groups may cyclize with a monocyclic heterocyclic group of E, A or T to form a bicyclic heterocyclic group.

Even more preferred are compounds according to each of formulae Ia and 'Ib, where $J^1$ is selected from the group consisting of H, —CN, —$NR^9R^{10}$, $R^4$, $R^6$, $R^9$ and $R^{10}$ are independently selected from the group consisting of H, —$(CH_2)_{0-6}$—SH, —$(CH_2)_{0-6}$—OH, —$(CH_2)_{0-6}$—$NH_2$, —$(CH_2)_{0-6}$—Cl, —$(CH_2)_{0-6}$—F, —$(CH_2)_{0-6}$—Br, —$(CH_2)_{0-6}$—I, —$(CF_2)_{1-5}$—$(CF_3)$, —$(CH_2)_{0-6}$—$(CF_3)$, —$(CH_2)_{0-6}$—CN, —$(CH_2)O$ —$NO_2$, —$(CH_2)_{0-6}$—CHO, —$C_{0-6}$alkyl, —$C_{0-6}$alkyl—$N(R^{a'})(R^{b'})_{0-1}$—$C_{0-6}$alkyl, —$(CH_2)_{0-1}$—CH=$(CH)_{0-1}$—$(CH_2)_{0-6}(CH_3)_{0-1}$, —O—$C_{1-6}$alkyl—$N(R^{a'})(R^{b'})_{0-1}$—$C_{0-6}$alkyl, —$C_{0-6}$alkyl—O—$C_{1-6}$alkyl, —$C_{0-12}$alkyl—O—$C_{2-12}$alkenyl, —$C_{2-12}$alkenyl—O—$C_{1-6}$alkyl, —$C_{2-12}$alkinyl, —$C_{0-12}$alkyl—O—$C_{1-6}$alkinyl, —$C_{0-12}$alkinyl—O—$C_{0-12}$alkyl—, —$C_{6-10}$aryl, —$C_{0-12}$alkyl—O—$C_{6-10}$aryl, —S(=O)$_{0-2}$—$C_{1-6}$alkyl —$N(R^{a'})(R^{b'})_{0-1}$—$C_{0-6}$alkyl, —$C_{0-6}$alkyl—S(=O)$_{0-2}$—$C_{1-6}$alkyl, —$C_{0-12}$alkyl—S(=O)$_{0-2}$—$C_{2-12}$alkenyl, —$C_{2-12}$alkenyl—S(=O)$_{0-2}$—$C_{1-6}$alkyl, —$C_{0-12}$alkyl—S(=)$_{0-2}$—$C_{1-6}$alkinyl, —$C_{0-12}$alkinyl—S(=O)$_{0-2}$—$C_{0-12}$alkyl—, —$C_{0-12}$alkyl—S(=O)$_{0-2}$—$C_{6-10}$aryl, —$C_{0-6}$alkyl$C_{6-10}$aryl, —$C_{2-12}$alkenyl$C_{6-10}$aryl, —$C_{2-12}$alkinyl$C_{6-10}$aryl, —COOH, —$C_{0-6}$alkyl—COO—$C_{1-6}$alkyl, —$C_{0-6}$alkyl—COO—$C_{2-12}$alkenyl, —$C_{0-6}$alkyl—COO—$C_{2-12}$alkinyl, —$C_{2-12}$alkenyl—COO—$C_{1-6}$alkyl, —$C_{2-12}$alkinyl—COO—$C_{1-6}$alkyl, —$C_{2-12}$alkenyl—COO—$C_{1-6}$alkyl, —$C_{2-12}$alkinyl—COO—$C_{0-6}$alkyl, —$C_{6-10}$aryl monocyclic or bicyclic ring structure selected from the group consisting of phenyl and naphthyl, and a three to ten membered heterocyclic monocyclic or bicyclic heterocyclic ring structure selected from the group consisting of benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H—indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3—thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl;

$R^{a'}$ and $R^{b'}$ are each independently selected from the group consisting of H, —CN, —$C_{0-6}$alkyl—SH, —$C_{0-}$ $_6$alkyl—OH, —C$_{0-6}$alkyl—CHO, —C$_{0-6}$alkyl—COOH, —C$_{0-6}$alkyl—N R$^{c'}$R$^{d'}$, —C$_{0-6}$—SH, —C$_{0-6}$alkenyl—OH, —C$_{0-6}$alkenyl—CHO, —C$_{0-6}$alkenyl—COOH, —C$_{0-6}$alkenyl—N R$^{c'}$R$^{d'}$, —C$_{0-6}$alkinyl—SH, —C$_{0-6}$alkinyl—OH, —C$_{0-6}$alkinyl—CHO, —C$_{0-6}$alkinyl—COOH, —C$_{0-6}$alkinyl—N R$^{c'}$R$^{d'}$, —C$_{1-6}$alkyl, —(CH$_2$)$_{1-6}$Cl, —(CH$_2$)$_{1-6}$—F, —(CH$_2$)$_{1-6}$—Br, —(CH$_2$)$_{1-6}$—I, —(CF$_2$)$_{1-3}$—(CF$_3$), —(CH$_2$),—$_{1-6}$—(CF$_3$), —(CH$_2$)$_{1-6}$—CN, —(CH$_2$)$_{0-6}$—NO$_2$, —C$_{1-6}$alkyl, —(CH$_2$)$_{0-4}$—CH=(CH)$_{0-1}$—(CH$_2$)$_{0-4}$(CH$_3$)$_{0-1}$,—C$_{0-5}$alkyl—O—C$_{1-6}$alkyl, —C$_{0-5}$alkyl—O—C$_{2-6}$alkenyl, —C$_{2-6}$alkenyl—O—C$_{1-6}$alkyl, —C$_{2-6}$alkinyl, —C$_{0-5}$alkyl—O—C$_{2-6}$alkinyl, —C$_{2-6}$alkinyl—O—C$_{0-6}$alkyl—, —C$_{6-10}$aryl, —C$_{0-4}$alkyl—O—C$_{6-10}$aryl, —C$_{0-6}$alkyl—S(=O)$_{0-2}$—C$_{1-6}$alkyl, —C$_{0-6}$alkyl—S(=O)$_{0-2}$—C$_{2-6}$alkenyl, —C$_{2-6}$alkenyl—S(=O)$_{0-2}$—C$_{1-6}$alkyl, —C$_{0-6}$alkyl—S(=O)$_{0-2}$—C$_{1-6}$alkinyl, —C$_{2-6}$alkinyl—S(=O)$_{0-2}$—C$_{1-6}$alkyl—, —C$_{0-6}$alkyl—S(=O)$_{0-2}$—C$_{6-10}$aryl, —C$_{0-6}$alkylC$_{6-10}$aryl, —C$_{2-6}$alkenylC$_{6-10}$aryl, —C$_{2-6}$alkinylC$_{6-10}$aryl, —C$_{0-6}$alkyl—COO—C$_{1-6}$alkyl, —C$_{0-6}$alkyl—COO—C$_{2-6}$alkenyl, —C$_{0-6}$alkyl—COO—C$_{2-6}$alkinyl, —C$_{2-6}$alkenyl—COO—C$_{1-6}$alkyl, —C$_{2-6}$alkinyl—COO—C$_{1-6}$alkyl, —C$_{2-6}$alkenyl—COO—C$_{1-6}$alkyl, —C$_{2-6}$alkinyl—COO—C$_{1-6}$alkyl, and a three to ten membered monocyclic or bicyclic heterocyclic ring structure selected from the group consisting of benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl, wherein the alkyl, alkenyl, and alkinyl portions of R$^{a'}$ and R$^{b'}$ may be linear or branched and may be substituted with from 0–6 members independently selected from the group consisting of —I, —F, —Br, —OH, —NO$_2$, —CF$_3$, —CHO, —NH2 and —COOH. R$^{a'}$ and R$^{b'}$ may be taken together or with a carbon atom having a free hydrogen to form an intracyclic bond resulting in a three to ten membered heterocyclic ring having from 1–4 heteroatoms selected from N, O and S;

R$^{c'}$ and R$^{d'}$: are independently selected from the group consisting of H, C$_{1-6}$alkyl—CHO, C$_{0-6}$alkyl—COOH,C$_{0-6}$alkyl—COCl, C$_{0-6}$alkyl—COI,C$_{0-6}$, C$_{0-6}$alkyl—COF, CO$_{0-6}$alkyl—COBr, C$_{0-6}$alkyl—COO—C$_{1-6}$alkyl, C$_{1-6}$alkyl—COO—C$_{2-6}$alkenyl, C$_{1-6}$alkyl—COO—C$_{2-6}$alkinyl, C$_{0-6}$alkyl—COO—C$_{0-6}$alkyl—CF$_3$C$_{1-6}$alkyl—COO—C$_{6-100}$aryl —COOH, C$_{0-6}$alkyl—CN, Clalkyl—NO$_2$, C$_{1-6}$alkyl—C$_{0-6}$C$_{1-6}$alkyl—Br, C$_{1-6}$alkyl—I, C$_{1-6}$alkyl—F, C$_{0-6}$alkyl—CF$_3$, C$_{1-6}$alkyl—CF$_2$—CF$_3$, C$_{1-6}$alkyl—SH, C$_{1-6}$alkyl, C$_{1-6}$alkenyl, C$_{1-6}$alkynyl, C$_{1-6}$alkyloxy, C$_{1-6}$alkenyloxy, C$_{1-6}$alkylthio, C$_{1-6}$alkenylthio, C$_{3-8}$cycloalkyl, C$_{6-10}$aryl, C$_{1-6}$alkylC$_{6-10}$aryl, a three to ten membered heterocyclic monocyclic or bicyclic ring system containing 1–4 heteroatoms selected from N, O and S; and C$_{1-4}$alkylheterocyclic monocyclic or bicyclic ring system having in the ring system 3 to 10 atoms with 1–4 of such atoms being selected from N, O and S;

alternatively, R$^9$ and R$^{10}$ taken together can form a five to ten membered heterocyclic monocyclic or bicyclic ring system containing 1–4 heteroatoms selected from N, O and S;

R$^7$ and R$^8$ are each independently selected from the group consisting of H, —(CH$_2$)$_{0-6}$—SH, —(CH$_2$)$_{0-6}$—OH, —(CH$_2$)$_{0-6}$—NH$_2$, —(CH$_2$)$_{0-6}$—C$_{0-6}$—(CH$_2$)$_{0-6}$—F, —(CH$_2$)$_{0-6}$—Br, —(CH$_2$)$_{0-6}$—I, —(CF$_2$)$_{1-5}$—(CF$_3$), —(CH$_2$)$_{0-6}$—(CF$_3$), —(CH$_2$)$_{0-6}$—CN, —(CH$_2$)$_{0-6}$—NO$_2$, —(CH$_2$)$_{0-6}$—CHO, —C$_{1-6}$alkyl, —C$_{0-6}$alkyl—N(R$^{a'}$)(R$^{b'}$),—C$_{0-6}$alkyl, —(CH$_2$)$_{(0-6}$—CH=(CH)$_{0-1}$—(CH$_2$)$_{0-6}$(CH$_3$)$_{0-1}$—, —O—C$_{1-6}$alkyl—N(R$^{a'}$)(R$^{b'}$)$_{0-1}$—C$_{0-6}$alkyl, —C$_{0-6}$alkyl—O—C$_{1-6}$alkyl, —C$_{0-12}$alkyl—O—C$_{0-12}$alkenyl, —C$_{2-12}$alkenyl—O—C$_{1-6}$alkyl, —C$_{2-12}$alkinyl, —C$_{0-12}$alkyl—O—C$_{1-6}$alkinyl, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{1-6}$alkyl—N(R$^{a'}$)(R$^{b'}$)$_{0-1}$—C$_{0-6}$alkyl, —C$_{0-6}$alkyl—S(=O)$_{0-2}$—C$_{1-6}$alkyl, —C$_{0-12}$alkyl—S(=O)$_{0-2}$—C$_{2-12}$alkenyl, —C$_{2-12}$alkenyl—S(=O)$_{0-2}$—C$_{1-6}$alkyl, —C$_{0-12}$alkyl—S(=O)$_{0-2}$—C$_{1-6}$alkinyl, —C$_{0-2}$alkinyl—S(=O)$_{0-2}$—C$_{0-12}$alkyl—, —C$_{0-12}$alkyl—S(=O)$_{0-2}$—C$_{6-10}$aryl, —C$_{0-6}$alkylC$_{0-6}$aryl, —C$_{2-12}$alkenylC$_{6-10}$aryl, —C$_{2-12}$alkinylC$_{6-10}$aryl, —COOH, —C$_{0-6}$alkyl—COO—C$_{0-6}$alkyl, —C$_{0-6}$alkyl—COO—C$_{2-12}$alkenyl, —C$_{0-6}$alkyl—COO—C$_{2-12}$alkinyl, —C$_{2-12}$alkenyl—COO—C$_{1-6}$alkyl, —C$_{2-12}$alkinyl—COO—C$_{1-6}$alkyl, —C$_{2-12}$alkenyl—COO—C$_{1-6}$alkyl, —C$_{2-12}$alkinyl—COO—C$_{1-6}$alkyl, —C$_{6-10}$aryl monocyclic or bicyclic ring structure, and a three to ten membered heterocyclic monocyclic or bicyclic heterocyclic ring structure containing 1–4 heteroatoms selected from N, O and S, where R$^{a'}$, R$^{b'}$, R$^{c'}$ and R$^{d'}$ are each as described above for this embodiment.

Alternatively, R$^7$ or R$^8$, independently, may be taken with either R$^5$ or R$^6$, to form a 3 to 10 membered heterocyclic monocyclic or bicyclic ring containing from 1–4 atoms selected from N, O and S. R$^7$ or R$^8$, independently taken with either Rs or R$^6$ may form a 3 to 10 membered heterocyclic monocyclic or bicyclic ring containing from 1–4 atoms selected from N, O and S.

In another preferred embodiment of the invention, ring structures E, A, and T of formulae IIa and IIb are independently a member selected from the group consisting of phenyl, naphthyl, 2-pyridyl, 3-pyridyl, 4-pyridyl, oxaxolyl, isoxazolyl, thiazolyl, isothiazolyl, imidazolyl and triazole, indolyl, and quinolinyl, which may be independently substituted with O to 4 R groups independently selected from the group consisting of H, —OH, halogen, trihalomethyl, —CN, —NO$_2$, C$_{1-6}$alkyl, C$_{3-8}$cycloalkyl, —O—C$_{1-6}$alkyl, C$_{1-6}$alkenyl, —O—C$_{1-6}$alkenyl, C$_{1-6}$alkinyl, —O—C$_{1-6}$alkinyl, C$_{6-10}$aryl, —O—C$_{6-10}$aryl, C$_{1-6}$alkylC$_{6-10}$aryl, —O—C$_{1-6}$alkylC$_{6-10}$aryl, —COOH and —COO—C$_{1-6}$alkyl. According to the invention, two R groups may combine to form a methylenedioxy or ethylenedioxy group.

In another preferred embodiment of the invention, ring structures E, A and T of formulae IIa and IIb are independently a member selected from the group consisting of phenyl, 2-pyridyl, 3-pyridyl, 4-pyridyl, oxaxolyl, isoxazolyl, thiazolyl, isothiazolyl and imidazolyl, which may be substituted with 0 to 4 R groups independently selected from the group consisting of H, —OH, halogen, trihalomethyl, —CN, —NO$_2$, C$_{1-6}$alkyl, C$_{3-8}$cycloalkyl, and —O—C$_{1-6}$alkyl.

In a more preferred embodiment of the invention, ring structures E, A and T of formulae IIa and IIb are independently a member selected from the group consisting of phenyl, 2-pyridyl, 3-pyridyl and 4-pyridyl, which may be substituted with 0 to 4 R groups which are independently a member selected from the group consisting of H, —OH, halogen, trihalomethyl, —CN, —NO$_2$, C$_{1-6}$alkyl and —O—C$_{1-6}$alkyl.

Preferably, ring structures E, A and T of formulae IIa and IIb are substituted with 0 to 2 R groups which are independently a member selected from the group consisting of H, —OH, —C$_{0-6}$—F, —Br, —I, —CF$_3$, —CCl$_3$, —CClF$_2$, —CN, —NO$_2$, —CH$_3$, —CH$_2$—CH$_3$, —CH$_2$—CH$_2$—CH$_3$, —CH—(CH$_3$)$_2$, —CH$_2$—CH$_2$—CH$_2$—CH$_3$, —O—CH$_3$, —O—CH$_2$—CH$_3$, and —O—CH$_2$—CH$_2$—CH$_3$. More preferably each R group is a member independently selected from the group consisting of H, —OH, —Cl, —F, —Br, —I, —CF$_3$, —CCl$_3$, —CClF$_2$, —CH$_3$, —CH$_2$—CH$_3$, —O—CH$_3$ and —O—CH$_2$—CH$_3$. Most preferably, each R group is a member independently selected from the group consisting of H, —OH, —F, —CF$_3$, and —CH$_3$.

In each of the preferred aspects of the formula IIa and IIb compounds, preferably, Z is selected from the group consisting of —(CH$_2$)$_{0-6}$—O—(CH$_2$)$_{0-6}$—, —(CH$_2$)$_{0-6}$—C(O)—(CH$_2$)$_{0-6}$—(CH$_2$)$_{0-6}$—C(=O)—O—(CH$_2$)$_{0-6}$—(CH$_2$)$_{0-6}$—O—C(=O)—(CH$_2$)$_{0-6}$—, —(CH$_2$)$_{0-6}$—C(=N(R$^{36}$))—(CH$_2$)$_{0-6}$—(CH$_2$)$_{0-6}$—C(=O)—N(R$^{36}$)—(CH$_2$)$_{0-6}$—(CH$_2$)$_{0-6}$—N(R$^{36}$)—C(=O)—(CH$_2$)$_{0-6}$—, —(CH$_2$)$_{0-6}$—S—(CH$_2$)$_{0-6}$—(CH$_2$)$_{0-6}$—S(O)$_2$—(CH$_2$)$_{0-6}$—, —(CH$_2$)$_{0-6}$—S(O)$_2$—N(R$^{36}$)—(CH$_2$)$_{0-6}$—, —(CH$_2$)$_{0-6}$—N(R$^{36}$)—SO$_2$—(CH$_2$)$_{0-6}$—, and —(CH$_2$)$_{0-6}$—N(R$^{36}$)—SO$_2$—N(R$^{37}$)—(CH$_2$)$_{0-6}$— where R$^{36}$ and R$^{37}$ are as described above for formula I. More preferably, Z is selected from the group consisting of —(CH$_2$)$_{0-6}$—C(=O)—N(R$^{36}$)—(CH$_2$)$_{0-6}$—(CH$_2$)$_{0-6}$—N(R$^{36}$)—C(=O)—(CH$_2$)$_{0-6}$—, —(CH$_2$)$_{0-6}$—S(O)$_2$—N(R$^{36}$)—(CH$_2$)$_{0-6}$— and —(CH$_2$)$_{0-6}$—N(R$^{36}$)—SO$_2$—(CH$_2$)$_{0-6}$—, where R$^{36}$ is as described above for formula I. Even more preferably, Z is selected from the group consisting of —(CH$_2$)$_{0-6}$—C(—O)—N(R$^{36}$)—(CH$_2$)$_{0-6}$—and —(CH$_2$)$_{0-6}$—N(R$^{36}$)—C(=O)—(CH$_2$)$_{0-6}$—, where R$^{36}$ is as described above for formula I. Most preferably, Z is selected from the group consisting of —C(=O)—N(R$^{36}$)— and —N(R$^{36}$)—C(=O)—, where R$^{36}$ is as described above for formula I.

Also, in each of the preferred aspects of the formula IIa and IIb compounds, preferably M is selected from the group consisting of —(CH$_2$)$_{0-6}$—O—(CH$_2$)$_{0-6}$—, —(CH$_2$)$_{0-6}$—C(=O)—(CH$_2$)$_{0-6}$—, —(CH$_2$)$_{0-6}$—C(=O)—O—(CH$_2$)$_{0-6}$—(CH$_2$)$_{0-6}$—O—C(=O)—(CH$_2$)$_{0-6}$—(CH$_2$)$_{0-6}$—S—(CH$_2$)$_{0-6}$—, —(CH$_2$)$_{0-6}$—S(O)—(CH$_2$)$_{0-6}$—(CH$_2$)$_{0-6}$—S(O)$_2$—(CH$_2$)$_{0-6}$—, —(CH$_2$)$_{0-6}$—N(R$^{38}$)—(CH$_2$)$_{0-6}$—(CH$_2$)$_{0-6}$—C(=N(R$^{38}$))—(CH$_2$)$_{0-6}$—(CH$_2$)$_{0-6}$—S(O)$_2$—N(R$^{38}$)—(CH$_2$)$_{0-6}$—, where R$^{38}$ is as described above for formula I. More preferably, M is selected from the group consisting of —(CH$_2$)$_{0-6}$—C(=O)—(CH$_2$)$_{0-6}$—, —(CH$_2$)$_{0-6}$—S(O)—(CH$_2$)$_{0-6}$—, —(CH$_2$)$_{0-6}$—S(O)$_2$—(CH$_2$)$_{0-6}$—, —(CH$_2$)$_{0-6}$—C(=N(R$^{38}$))—(CH$_2$)$_{0-6}$— and —(CH$_2$)$_{0-6}$—N(R$^{38}$)—(CH$_2$)$_{0-6}$ where R$^{38}$ is as described above for formula I. Even more preferably, M is selected from the group consisting of —(CH$_2$)$_{0-6}$—C(=O)—(CH$_2$)$_{0-6}$—, —(CH$_2$)$_{0-6}$—S(O)$_2$—(CH$_2$)$_{0-6}$—, and —(CH$_2$)$_{0-6}$—C(=N(R$^{38}$))—(CH$_2$)$_{0-6}$ where R$^{38}$ is as described above for formula I. Most preferably, M is selected from the group consisting of —C(=O)—, —S(O)$_2$—, and —C(=N(R$^{38}$))—, where R$^{38}$ is as described above for formula I.

Preferred compounds of the invention also include those compounds of following formulae III, IV, V, VI, VII and VIII:

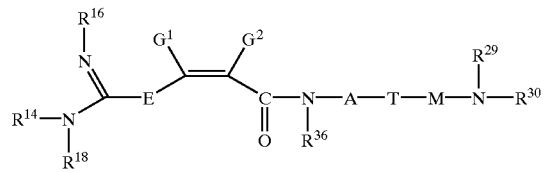

III

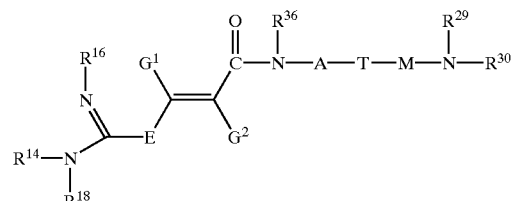

IV

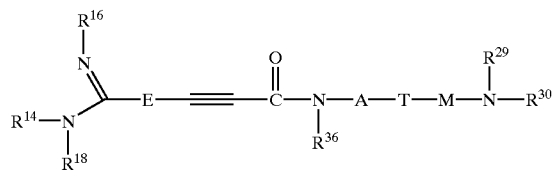

V

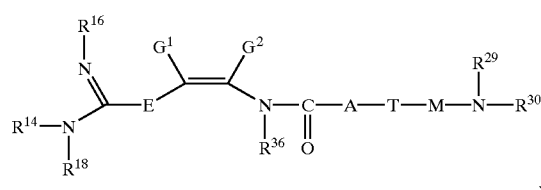

VI

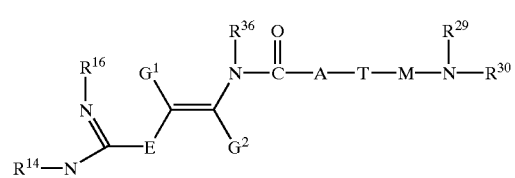

VII

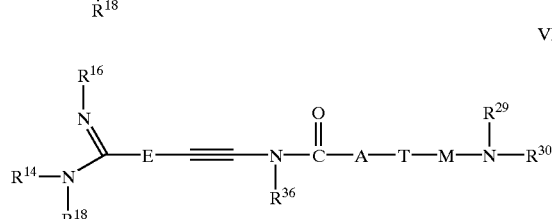

VIII

In formulae III, IV, V, VI, VII and VIII, E, A, T, M, G$^1$, G$^2$, R$^{14}$, R$^{16}$, R$^{18}$, R$^{29}$, R$^{30}$, and R$^{36}$ are each as described above for formula I.

Preferably, in formulae III, IV, V, VI, VII and VIII, M is selected from the group consisting of —(CH$_2$)$_{0-6}$—(CH$_2$)$_{0-6}$—, —(CH$_2$)$_{0-6}$—C(=O)—(CH$_2$)$_{0-6}$—, —(CH$_2$)$_{0-6}$—C(=O)—O—(CH$_2$)$_{0-6}$—, —(CH$_2$)$_{0-6}$—C(=O)—(CH$_2$)$_{0-6}$—, —(CH$_2$)$_{0-6}$—S—(CH$_2$)$_{0-6}$—(CH$_2$)$_{0-6}$—S(O)—(CH$_2$)$_{0-6}$—, —(CH$_2$)$_{0-6}$—S(O)$_2$—(CH$_2$)$_{0-6}$—(CH$_2$)$_{0-6}$—N(R$^{38'}$)—

$(CH_2)_{0-6}$—$(CH_2)_{0-6}$—$C(=N(R^{38}))$—$(CH_2)_{0-6}$ and —$(CH_2)_{0-6}$—$S(O)_2$—$N(^{38})$—$(CH_2)_{0-6}$, where $R^{11}$ is as described above for formula I. More preferably, M is selected from the group consisting of —$(CH_2)_{0-6}$—$C(=O)$—$(CH_2)_{0-6}$—, —$(CH_2)_{0-6}$—$S(O)$—$(CH_2)_{0-6}$—, —$(CH_2)_{0-6}$—$S(O)_2$—$(CH_2)_{0-6}$—, —$(CH_2)_{0-6}$—$C(=N(R^{38}))$—$(CH_2)_{0-6}$— and —$(CH_2)_{0-6}$—$N(R^{38})$—$(CH_2)_{0-6}$, where $R^{3"}$ is as described above for formula I. Even more preferably, M is selected from the group consisting of —$(CH_2)_{0-6}$—$C(=O)$—$(CH_2)_{0-6}$—, —$(CH_2)_{0-6}$—$S(O)_2$—$(CH_2)_{0-6}$—, and —$(CH2)_{0-6}$—$C(=N(R^{38}))$—$(CH_2)_{0-6}$— where $R^{38}$ is as described above for formula I. Most preferably, M is selected from the group consisting of—$C(=O)$—, —$S(O)_2$—, and —$C(=N(R^{38}))$—, where $R^{38}$ is as described above for formula I. Preferably, $R^{38}$ is hydrogen, lower alkyl, lower alkenyl, lower alkyl comprising at least one halogen atom in place of a hydrogen atom and lower alkenyl comprising at least one halogen atom in place of a hydrogen atom. Alternatively $R^{38}$ may be taken together with $R^{29}$ or $R^{30}$ of J to form an aromatic or non—aromatic 3 to 12 member heterocyclic ring structure containing 1–4 heteroatoms selected from N, O and S.

Further preferred are compounds of formulae III, IV, V, VI, VII and VIII, where the carbocyclic and heterocyclic substituents and the carbocyclic and heterocyclic E, A and T groups, if present, may be unsubstituted or substituted with a group independently selected from the group consisting of cyclopropyl, cyclobutyl, cyclopentyl, cyclohexyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, tetrahydronaphthyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH—carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

More preferably, the carbocyclic and heterocyclic substituents and the carbocyclic and heterocyclic E, A and T groups, if present, may be unsubstituted or substituted with a group independently selected from the group consisting of cyclopropyl, cyclobutyl, cyclopentyl, cyclohexyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, tetrahydronaphthyl, benzimidazolyl, benzofuranyl, benzothiofuranyl, benzothiophenyl, benzoxazolyl, benzthiazolyl, benzisoxazolyl, benzisothiazolyl, benzimidazalinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolyl, 3H-indolyl, isobenzofuranyl, isochromanyl, isoindazolyl, isoindolyl, isoquinolinyl, isothiazolyl, isoxazolyl, morpholinyl, oxadiazolyl, 1,2,3-oxadiazolyl, oxazolyl, pyrimidinyl, piperazinyl, piperidinyl, pyrazolyl, pyridyl, pyrimidinyl, pyrrolidinyl, pyrrolinyl, 2H-pyrrolyl, pyrrolyl, quinolinyl, 4H-quinolizinyl, tetrahydrofuranyl, thiazolyl, thienyl, thienothiazolyl, thienooxazolyl, 1,2,3-triazolyl, 1,2,4-triazolyl, 1,2,5-triazolyl, 1,3,4-triazolyl and xanthenyl.

Without limiting the scope of the invention, examples of the preferred embodiments for E, A, T, $G^1$ and $G^2$ are set forth in Table 1 below for each of the preferred compounds of formulae IIIa, IIIb, IIIc, IVa, IVb, IVc, Va, Vb, Vc, VIa, VIb, VIc, VIIa, VIIb, VIIc, VIIIa, VIIb and VIIIc as set forth below. In formulae IIIa, IIIb, IIIc, IVa, IVb, IVc, Va, Vb, Vc, VIa, VIb, VIc, VIIa, VIIb, VIIc, VIIIa, VIIIb and VIIIc, $R^{14}$, $R^{16}$, $R^{18}$, $R^{29}$, $R^{30}$, $R^{36}$ and $R^{38}$ each are as described above for formula I. Further preferred are those compounds where $R^{14}$, $R^{16}$, $R^{18}$, $R^{29}$, $R^{30}$, $R^{36}$ and $R^{38}$, if present, are independently selected from hydrogen, lower alkyl and lower alkenyl. To simplify matters, examples of preferred E, A, T, $G^1$ and $G^2$ groups for each of formulae IIa, IIIb, IIIc, IVa, WVb, IVc, Va, Vb, Vc, VIa, VIb, VIc, VIIa, VIb, VIIc, VIIIa, VIIIb and VIIIc have been summarized in single Table 1. Each set of E, A, T, $G^1$ and $G^2$ groups may be applied independently to each compound of formulae IIIa, IIIb, IIIc, IVa, IVb, IVc, Va, Vb, Vc, VIa, VIb, VIc, VIIa, VIIb, VIIc, VIIIa, VIIIb and VIIc. However, since $G^1$ and $G^2$ are absent in formulae Va, Vb, Vc and VIIIa, VIIIb and VIIIc, only E, A and T listed in Table 1 apply to these formulae.

IIIa
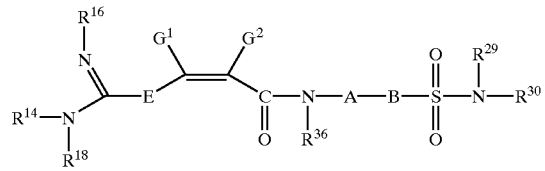

IIIb
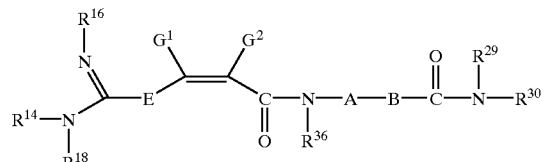

IIIc
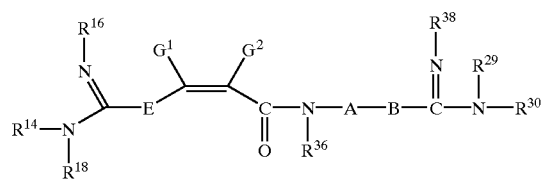

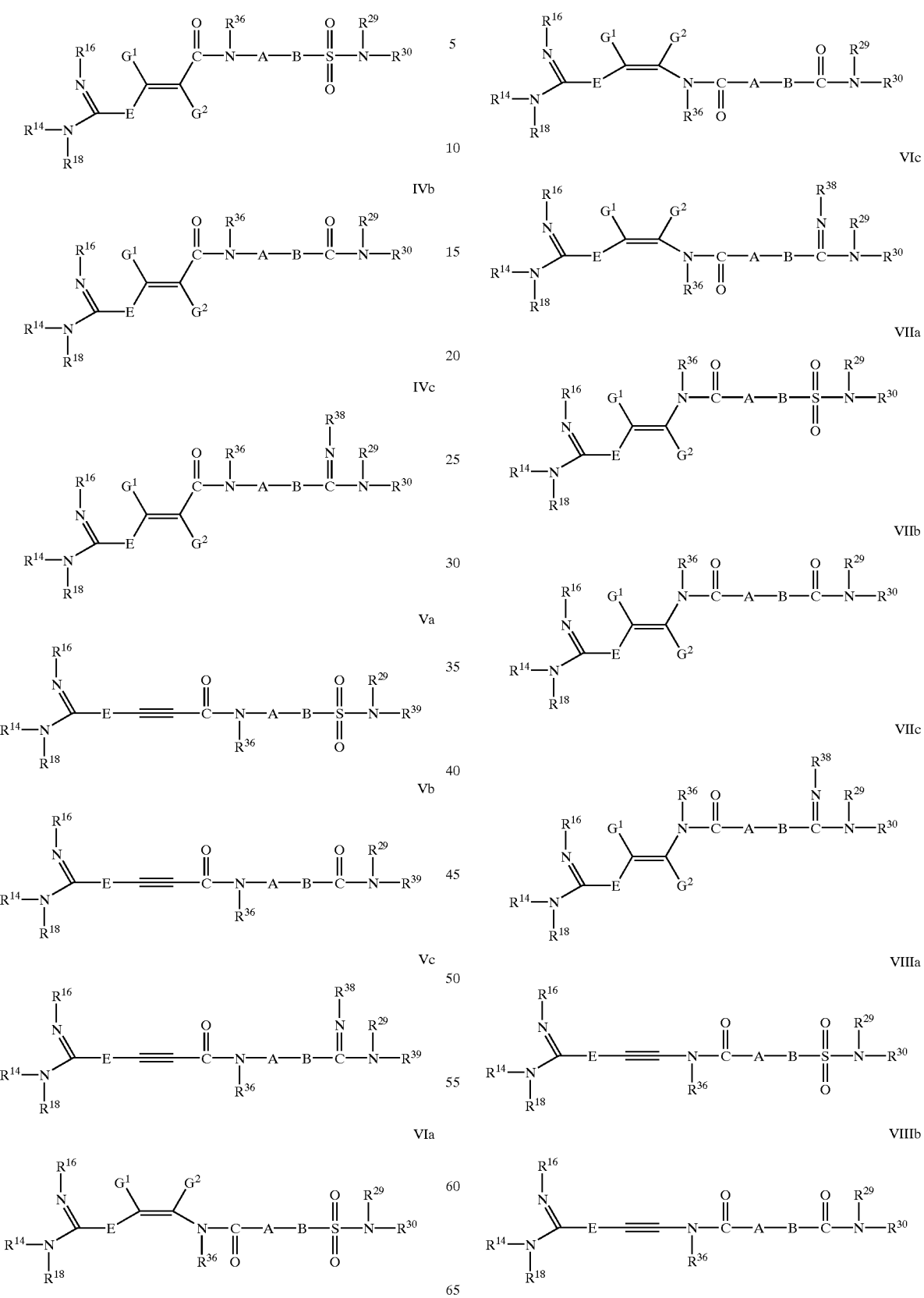

-continued
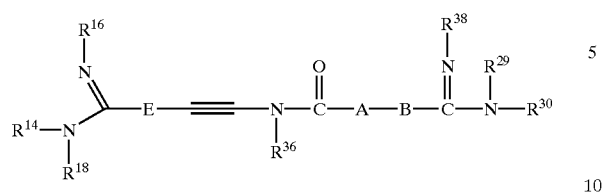
VIIIc
TABLE 1
| E | A | T | G$^1$ | G$^2$ |
|---|---|---|---|---|
| ⬡ | ⬡ | ⬡ | —H | —H |
| ⬡ | ⬡ | ⬡ | —CH$_3$ | —H |
| ⬡ | ⬡ | ⬡ | —H | —CH$_3$ |
| ⬡ | ⬡ | ⬡ | —CH$_3$ | —CH$_3$ |
| ⬡ | ⬡ | ⬡ | —CH$_2$—CH$_2$—CH$_2$— | |
| ⬡ | ⬡ | ⬡ | —CH$_2$=CH$_2$—CH$_2$— | |
| ⬡ | ⬡ | ⬡ | —CH$_2$—CH$_2$=CH$_2$— | |
| ⬡ | ⬡ | — | —H | —H |
| ⬡ | ⬡ | — | —CH$_3$ | —H |
| ⬡ | — | ⬡ | —H | —H |

TABLE 1-continued
| E | A | T | G¹ | G² |
|---|---|---|---|---|
| 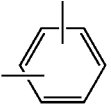 | — | 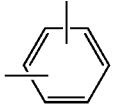 | —CH₃ | —H |
| 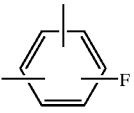 | 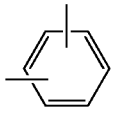 | 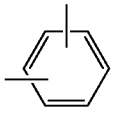 | —H | —H |
| 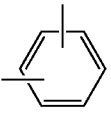 | 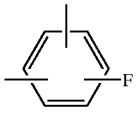 | 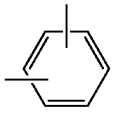 | —H | —H |
| 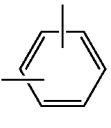 | 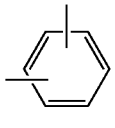 | 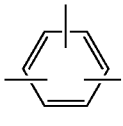 | —H | —H |
| 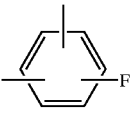 | 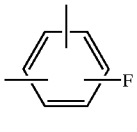 | 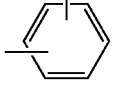 | —H | —H |
| 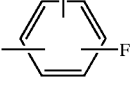 | 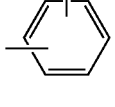 | 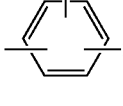 | —H | —H |
| 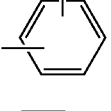 | 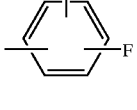 | 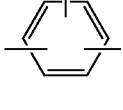 | —H | —H |
| 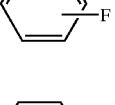 | 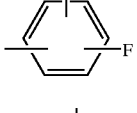 | 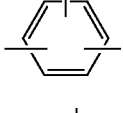 | —H | —H |
| 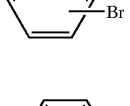 | 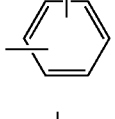 | 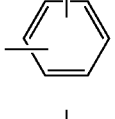 | —H | —H |
| 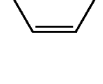 |  | 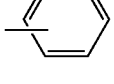 | —H | —H |
| 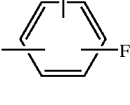 | 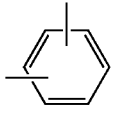 |  | —H | —H |
| 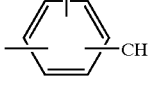 | 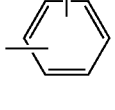 | 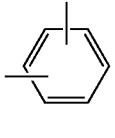 | —H | —H |

TABLE 1-continued

| E | A | T | G¹ | G² |
|---|---|---|---|---|
| phenyl | 4-methylphenyl | phenyl | —H | —H |
| phenyl | phenyl | 4-methylphenyl | —H | —H |
| 4-methylphenyl | 4-methylphenyl | phenyl | —H | —H |
| 4-methylphenyl | phenyl | 4-methylphenyl | —H | —H |
| phenyl | 4-methylphenyl | 4-methylphenyl | —H | —H |
| 4-methylphenyl | 4-ethylphenyl | 4-methylphenyl | —H | —H |
| 4-isopropylphenyl | phenyl | phenyl | —H | —H |
| 4-tert-butylphenyl | phenyl | phenyl | —H | —H |
| 4-isobutylphenyl | phenyl | phenyl | —H | —H |
| pyridyl | phenyl | phenyl | —H | —H |
| phenyl | pyridyl | phenyl | —H | —H |
| phenyl | phenyl | pyridyl | —H | —H |

TABLE 1-continued

| E | A | T | G¹ | G² |
|---|---|---|----|----|
| pyridine | pyridine | benzene | —H | —H |
| pyridine | benzene | pyridine | —H | —H |
| benzene | pyridine | pyridine | —H | —H |
| pyridine | pyridine | pyridine | —H | —H |
| pyrimidine | benzene | benzene | —H | —H |
| pyrazine | benzene | benzene | —H | —H |
| benzene | benzene | pyrazine | —H | —H |
| pyridine | benzene | benzene | —H | —H |
| benzene | N-methyl pyridine | benzene | —H | —H |
| benzene | benzene | thiophene | —H | —H |
| benzene | thiophene | benzene | —H | —H |
| benzene | benzene | pyrrole | —H | —H |

TABLE 1-continued

| E | A | T | G¹ | G² |
|---|---|---|----|----|
| phenyl | phenyl | naphthyl | —H | —H |
| phenyl | naphthyl | phenyl | —H | —H |
| naphthyl | phenyl | phenyl | —H | —H |
| phenyl | phenyl | oxazolyl | —H | —H |
| fluorophenyl | phenyl | thiazolyl | —H | —H |

More preferred are compounds of formulae IIIa, IIIb, IIIc, IVa, IVb, IVc, Va, Vb, Vc, VIa, VIb, VIc, VIIa, VIIb, VIIc, VIIIa, VIIIb and VIIIc where E, A and T have 0 to 3 substituents selected from the group consisting of hydrogen, —CN, —NO$_2$, —OH, —SH, —Cl, —Br, —I, —F, methyl, ethyl, propyl, isopropyl, butyl, isobutyl, t-butyl, pentyl, isopentyl, ethylenyl, propylenyl, methoxy, ethoxy, propoxy, isopropoxy, butoxy, isobutoxy, t-butoxy, trihalomethyl (in particular, trifluoromethyl), 1,1,1—trifluroethyl, tetrahaloethyl, pentahaloethyl, ethylenyl, propylenyl, —MeOH, —EtOH, —PrOH, —MeSH, —EtSH, —PrSH, formyl, acetyl, and the like.

Without limiting the scope of the invention, examples of the preferred embodiments for E, A, T, G¹ and G² are set forth in Table 2 below for each of the more preferred compounds of formulae IIId, IIIe, IIIf, IVd, IVe, IVf, Vd, Ve, Vf, VId, VIe, VIf, VIId, VIIe, VIIf, VIIId, VIIIe and VIIIf as set forth below. R$^{36}$ is independently selected from the group consisting of hydrogen, methyl, ethyl, propyl, isopropyl, butyl, isobutyl, t-butyl, pentyl, isopentyl, methoxy, ethoxy, propoxy, trihalomethyl, and pentahaloethyl. To simplify matters, examples of preferred E, A, T, G¹ and G² groups for each of formulae IIId, IIIe, IIIf, IVd, IVe, IVf, Vd, Ve, Vf, VId, VIe, VIf, VIId, VIIe, VIIf, VIIId, VIIIe and VIIIf have been summarized in single Table 2. Each set of E, A, T, G¹ and G² groups may be applied independently to each compound of formulae IIId, IIIe, IIIf, IVd, IVe, IVf, Vd, Ve, Vf, VId, VIe, VIf, VIId, VIIe, VIIf, VIIId, VIIIe and VIIf However, since G¹ and G² are absent in formulae Vd, Ve, Vf, VIIId, VIIIe and VIHIf, only E, A and T listed in Table 2 apply to these formulae.

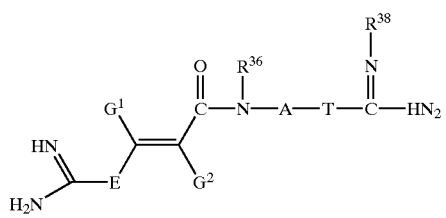
IVf
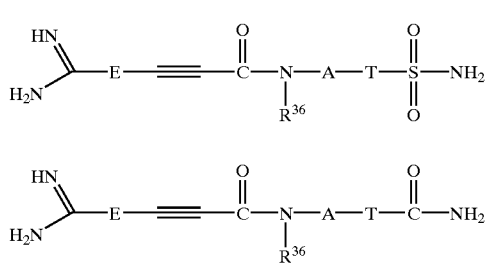
Vd
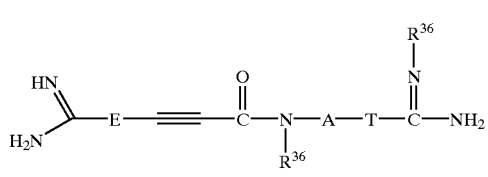
Ve
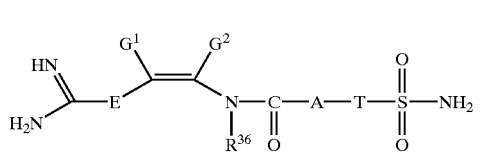
Vf
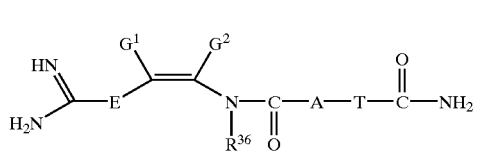
VId
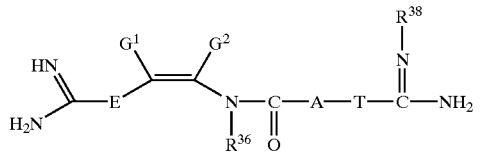
VIe
VIf
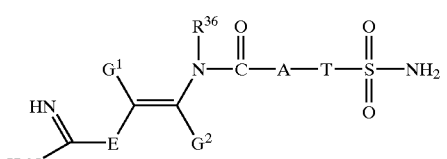
VIId
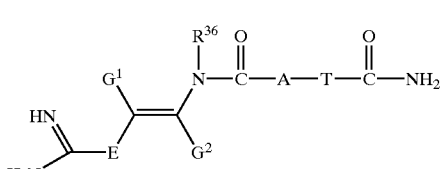
VIIe
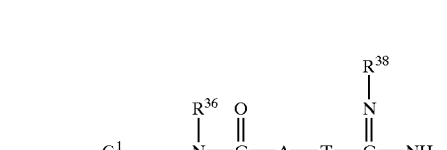
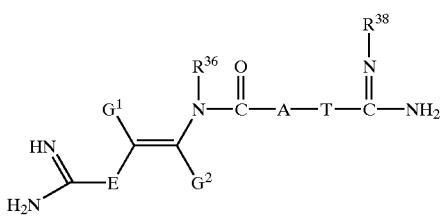
VIIf
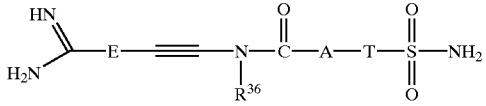
VIIId
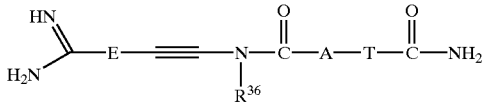
VIIIe
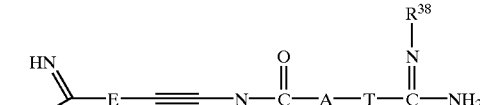
VIIIf
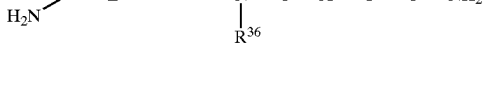
TABLE 2
| E | A | T | $G^1$ | $G^2$ |
|---|---|---|---|---|
| ⌬ | ⌬ | ⌬ | —H | —H |
| ⌬ | ⌬ | ⌬ | —CH$_3$ | —H |

TABLE 2-continued

| E | A | T | G¹ | G² |
|---|---|---|---|---|
| cyclohexenyl | cyclohexenyl | cyclohexenyl | —H | —CH$_3$ |
| cyclohexenyl | cyclohexenyl | cyclohexenyl | —CH$_3$ | —CH$_3$ |
| cyclohexenyl | cyclohexenyl | cyclohexenyl | —CH$_2$—CH$_2$—CH$_2$— | |
| cyclohexenyl | cyclohexenyl | cyclohexenyl | —CH$_2$=CH$_2$—CH$_2$— | |
| cyclohexenyl | cyclohexenyl | cyclohexenyl | —CH$_2$—CH$_2$=CH$_2$— | |
| cyclohexenyl | cyclohexenyl | — | —H | —H |
| cyclohexenyl | cyclohexenyl | — | —CH$_3$ | —H |
| cyclohexenyl | — | cyclohexenyl | —H | —H |
| cyclohexenyl | — | cyclohexenyl | —CH$_3$ | —H |
| F-cyclohexenyl | cyclohexenyl | cyclohexenyl | —H | —H |
| cyclohexenyl | F-cyclohexenyl | cyclohexenyl | —H | —H |
| cyclohexenyl | cyclohexenyl | F-cyclohexenyl | —H | —H |

TABLE 2-continued
| E | A | T | G¹ | G² |
|---|---|---|---|---|
| 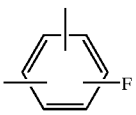 | 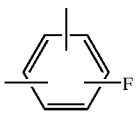 | 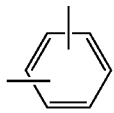 | —H | —H |
| 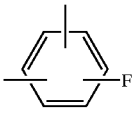 | 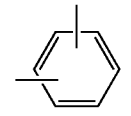 | 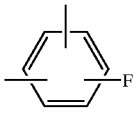 | —H | —H |
| 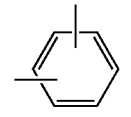 | 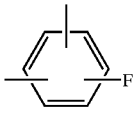 | 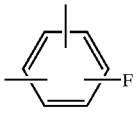 | —H | —H |
| 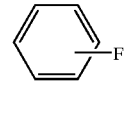 | 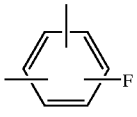 | 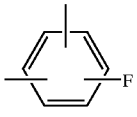 | —H | —H |
| 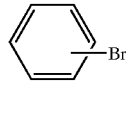 | 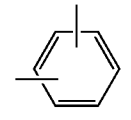 | 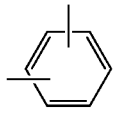 | —H | —H |
|  | 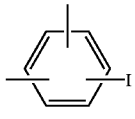 | 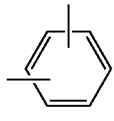 | —H | —H |
| 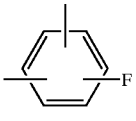 | 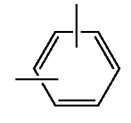 | 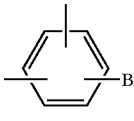 | —H | —H |
| 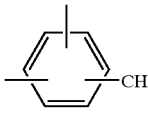 | 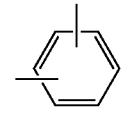 | 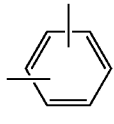 | —H | —H |
| 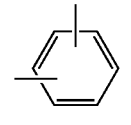 | 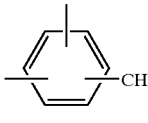 | 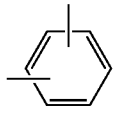 | —H | —H |
| 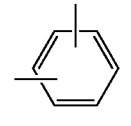 | 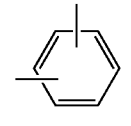 | 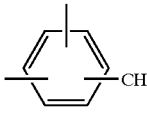 | —H | —H |
| 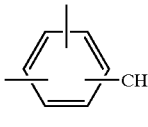 | 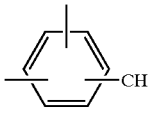 | 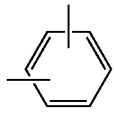 | —H | —H |
| 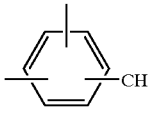 | 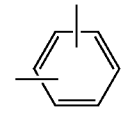 | 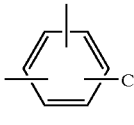 | —H | —H |

TABLE 2-continued
| E | A | T | G¹ | G² |
|---|---|---|---|---|
| 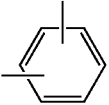 | 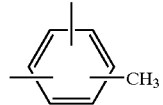 | 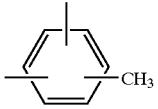 | —H | —H |
| 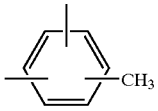 | 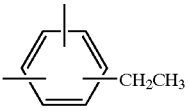 | 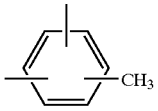 | —H | —H |
| 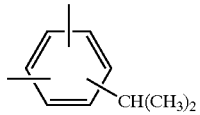 | 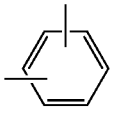 | 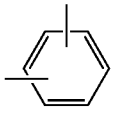 | —H | —H |
| 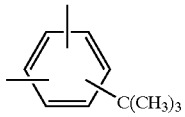 | 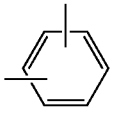 | 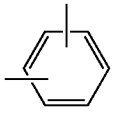 | —H | —H |
| 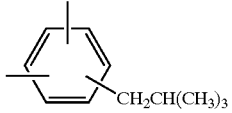 | 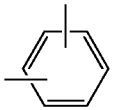 | 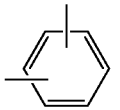 | —H | —H |
| 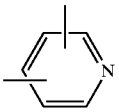 | 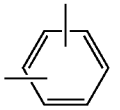 | 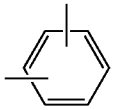 | —H | —H |
| 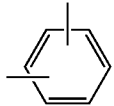 | 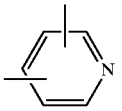 | 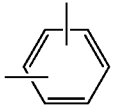 | —H | —H |
| 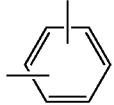 | 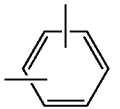 | 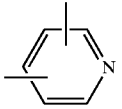 | —H | —H |
| 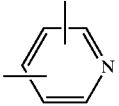 | 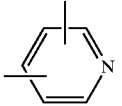 | 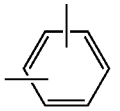 | —H | —H |
| 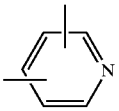 | 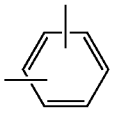 | 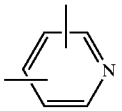 | —H | —H |
| 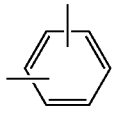 | 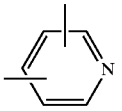 | 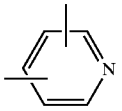 | —H | —H |
| 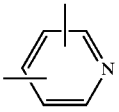 | 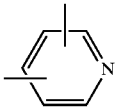 | 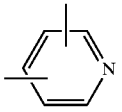 | —H | —H |

TABLE 2-continued

| E | A | T | G¹ | G² |
|---|---|---|----|----|
| pyrimidine | phenyl | phenyl | —H | —H |
| pyrazine | phenyl | phenyl | —H | —H |
| phenyl | phenyl | pyrazine | —H | —H |
| pyridine | phenyl | phenyl | —H | —H |
| phenyl | N-methyl pyridine | phenyl | —H | —H |
| phenyl | phenyl | thiophene | —H | —H |
| phenyl | thiophene | phenyl | —H | —H |
| phenyl | phenyl | pyrrole | —H | —H |
| phenyl | phenyl | naphthyl | —H | —H |
| phenyl | naphthyl | phenyl | —H | —H |
| naphthyl | phenyl | phenyl | —H | —H |
| phenyl | phenyl | oxazole | —H | —H |

TABLE 2-continued
| E | A | T | G¹ | G² |
|---|---|---|---|---|
| 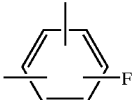 |  | 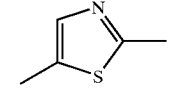 | —H | —H |
Also preferred are the compounds set forth below in the following Tables 3–6:
TABLE 3
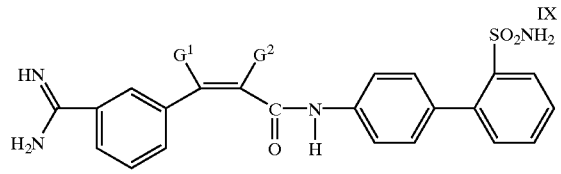
IX
| G¹ | G² |
|---|---|
| —CF₃ | —H |
| —iPr | —H |
| —H | 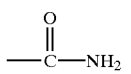 |
| —H | 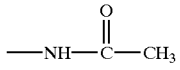 |
| —H | 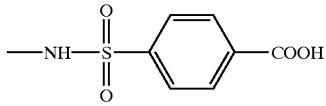 |
| —H |  |
| —H | —F |
| —H | —H |
| —CH₃ | —H |
| —H | —CH₃ |
| —CH₃ | —CH₃ |
|  | —CH₂—CH₂—CH₂— |
|  | —CH₂=CH₂—CH₂— |
|  | —CH₂—CH₂=CH₂— |
| —CF₃ |  |
| —H | 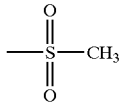 |
| 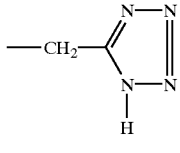 | —H |
TABLE 3-continued
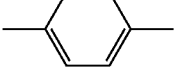
IX
| G¹ | G² |
|---|---|
| —H | 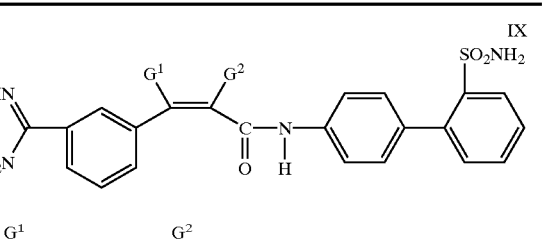 |
| 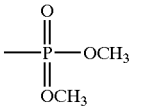 | —H |
| —H | —COOH |
| —H | 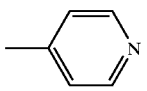 |
| —F | —H |
| —H |  |
| —H |  |
| —H | 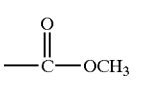 |
| —H | 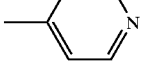 |
| —H | 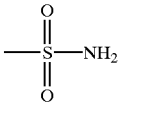 |
| —H | 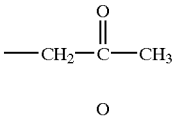 |

Table 4 compounds are set forth below.

TABLE 4

[Structure: 3-amidinophenyl-CH=CH-C(=O)-NH-A-T-M-J with X substituent]

| A | B—F—J |
|---|---|
| 1,4-phenylene | 2-(SO₂NH₂)-phenyl |
| 1,4-phenylene | 2-(SO₂CH₃)-phenyl |
| 1,4-phenylene | 2-(CF₃)-phenyl |
| 2-Cl-1,4-phenylene | 2-(SO₂NH₂)-phenyl |
| 2-F-1,4-phenylene | 2-(SO₂NHCH₃)-phenyl |
| 2-Br-1,4-phenylene | 2-(SO₂NH₂)-phenyl |
| pyridine-2,5-diyl | 2-(SO₂NH₂)-phenyl |
| pyrimidine-2,5-diyl | 2-(SO₂NH₂)-phenyl |
| 4-F-1,3-phenylene | 2-(SO₂NHC(—CH₃)₃)-phenyl |

TABLE 4-continued

[Structure: 3-amidinophenyl-CH=CH-C(=O)-NH-A-T-M-J with X substituent]

| A | B—F—J |
|---|---|
| 1,4-phenylene | N-imidazolyl |
| 1,4-phenylene | C(=O)-N-pyrrolidinyl |
| 2-F-1,4-phenylene | 2-(SO₂N(CH₃)₂)-phenyl |

Table 5 compounds are set forth below.

TABLE 5

[Structure: 3-amidinophenyl-CH=CH-Z-(4-phenyl)-2'-(SO₂NH₂)-biphenyl with X substituent]

Z

—NH—C(=O)—

—C(=O)—NH—

—CH₂—NH—

—CH₂—O—

—S(=O)₂—NH—

—CH₂—NH—C(=O)—

Table 6 compounds are set forth below.

TABLE 6

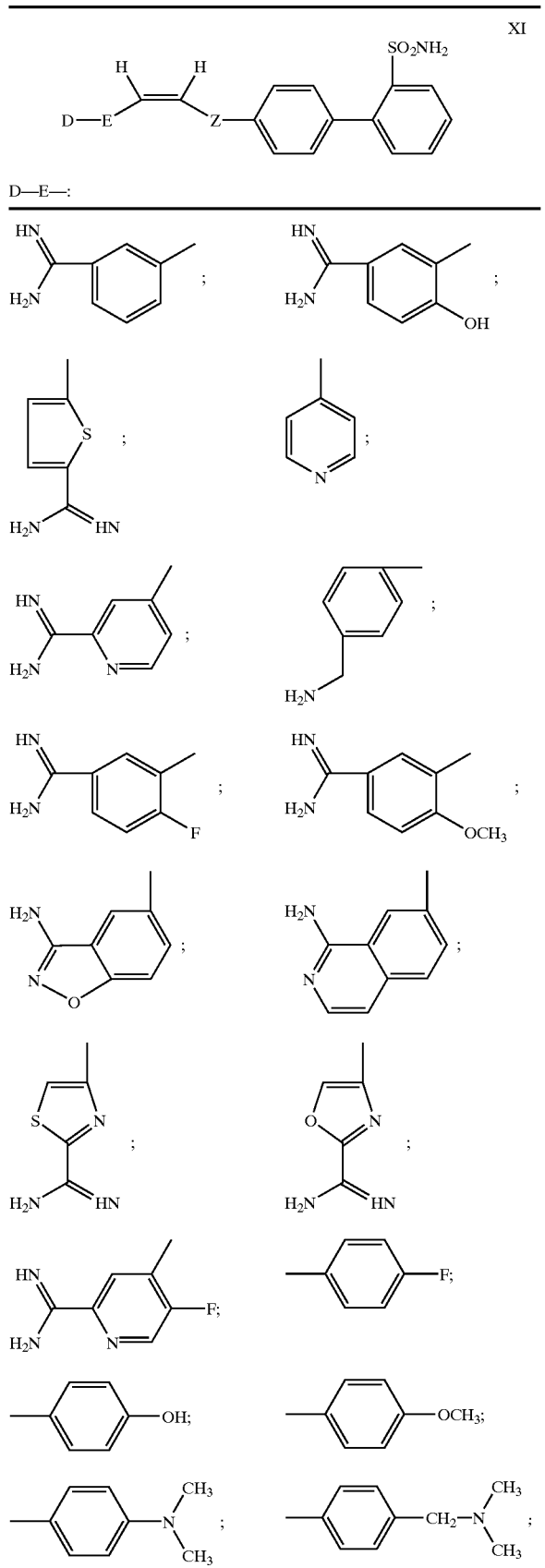

TABLE 6-continued

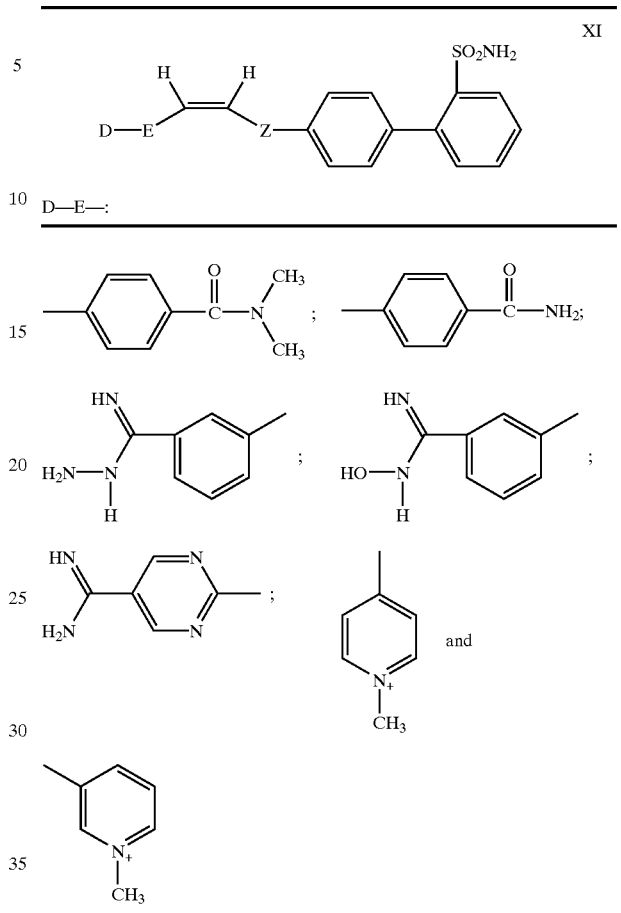

The invention also encompasses all pharmaceutically acceptable isomers, salts, hydrates, and solvates of each of the compounds described above. In addition, such compounds can exist in various isomeric and tautomeric forms, and all such forms are meant to be included in the invention, along with pharmaceutically acceptable salts, hydrates, and solvates of such isomers and tautomers.

The invention also encompasses prodrug derivatives of the compounds of the invention. The term "prodrug" as used herein refers to a pharmacologically inactive derivative or precursor of a compound of the invention which upon biotransformation, either spontaneous or enzymatic, within an organism releases the compound of the invention as a pharmaceutically active drug. Prodrug derivatives of compounds of the invention contain groups cleavable under metabolic conditions such as, for example, solvolysis under physiological conditions or enzymatic degradation. According to the invention, compounds of the invention resulting from the biotransformation of their prodrug derivatives are pharmaceutically active in vivo. Prodrug derivatives of compounds of the invention may be designated as single, double, triple, etc., corresponding to the number of biotransformation steps required to release the pharmaceutically active compound of the invention within the organism and/or indicating the number of functionalities present in the prodrug derivative. Prodrugs often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Acadernic Press, San Diego, CA, 1992).

The compounds of the invention may be prepared by any means known in the art including solid, liquid, or gas phase methods or a combination thereof. For example, a compound of the invention may be prepared using known olefination and acetylation methods. Preferably, a compound of the invention may be prepared from a carbonyl compound under modified Wittig reaction conditions or by reduction of an acetylene derivative precursor, each as would be recognized by one of skill in the art. A compound of the invention may also be prepared under nucleophilic displacement or elimination reaction conditions, each as would be recognized by one of skill in the art. For example, an alkenyl compound of the invention may be synthesized by means of a Wittig-type coupling reaction followed by a displacement reaction as illustrated in Scheme 1 below. As would be recognized by one of skill in the art, the reaction conditions for the coupling and displacement illustrated in Scheme 1 may be varied depending upon such factors as the reactants and the desired compound of the invention. In addition, various functional groups of the reactants may be blocked by protecting groups to prevent cross reaction during the coupling and displacement steps. Examples of suitable blocking groups include those known in the art and as described in standard organic textbooks.

Scheme 1

In Scheme 1, L is a leaving group and RX is a methylene activating group/leaving group. D, E, $G^1$, $G^2$, Z, A, T, M and J are each as described above. Preferably, in Scheme 1, R, is a Z methylene activating group.

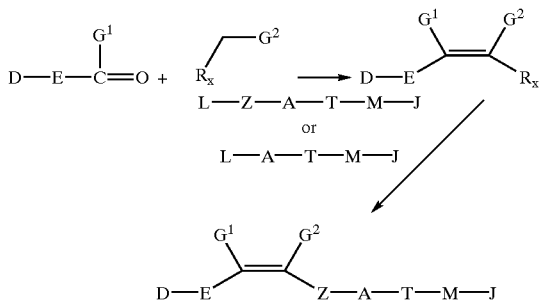

The compounds of the invention may be prepared using reactants or starting materials commercially available from chemical vendors such as Aldrich, Sigrna, Nova Biochemicals, Bachem Biosciences, and the like, or readily synthesized by known procedures.

The desired compound of the invention may be isolated and purified by conventional methods, typically by solvent extraction into a compatible solvent, followed by removal of the solvent. The products may be further purified by column chromatography or other appropriate methods. Racemic mixtures may be resolved utilizing methods standard in the art.

Furthermore, as described above, the compounds of the invention may be isolated as the free acid or base or converted to pharmaceutically acceptable salts of various inorganic and organic acids and bases. Non-toxic and physiologically compatible salts are particularly preferred although other less desirable salts may be useful precursors in the synthesis, isolation and purification of the final desired compound. A pharmaceutically acceptable salt of a compound of the invention may be prepared using any means known in the art. For example, a salt of a compound of the invention may be prepared by reacting the free acid or free base form of a compound of the invention with one or more molar equivalents of, respectively, an appropriate base or acid in an organic or aqueous solvent or solvent mixture, and then removing the solvent(s). The solvent(s) may be removed using procedures known in the art including, but not limited to, evaporation, distillation, and freeze drying. Alternatively, the free acid or base form of a compound of the invention may be passed over an ion exchange resin to form the desired salt or to convert one salt form to another.

Prodrug derivatives of compounds of the invention may also be prepared by any means known in the art. For example, an ester prodrug derivative of a compound of the invention may be prepared by reacting the corresponding acid compound of the invention with an alcohol while an amide prodrug derivative of a compound of the invention may by prepared by reaction of the corresponding acid compound of the invention with an amine. Likewise, basic groups found on a compound of the invention may be acylated to form an acylated prodrug derivative. Moreover, the prodrug derivatives of the invention may be combined with other features herein taught to enhance bioavailability.

Compositions and Methods of Treatment

The compounds of the invention, as described above, may be formulated into pharmaceutical compositions. Accordingly, the invention also provides a pharmaceutical composition comprising a pharmaceutically effective amount of a compound of the invention, as described above, and a pharmaceutically acceptable carrier.

Pharmaceutical compositions of the invention may be prepared for storage or administration by any means known in the art. For example, a pharmaceutical composition of the invention may be prepared by mixing a compound of the invention, preferably having a desired degree of purity, with a pharmaceutically or physiologically acceptable carriers or agent. Preferably, a pharmaceutical composition of the invention may be prepared by compounding about 0.5–500 mg, preferably, about 1–250 mg, more preferably, about 1–80 mg, of at least one compound of the invention with a physiologically acceptable carrier or agent, each as described herein. The amount of active ingredient in these compositions is such that a suitable dosage in the range indicated is obtained.

A pharmaceutically acceptable carrier or agent may be any such carrier or agent known in the art. See, for example, in Remington's Pharmaceutical Sciences, Mack Publishing Co., (A.R. Gennaro edit. 1985). A pharmaceutical composition of the invention may further include a binder (e.g., acacia, corn starch or gelatin), an excipient (e.g., microcrystalline cellulose), a disintegrating agent (e.g., corn starch or alginic acid), a lubricant (e.g., magnesium stearate), a sweetening agent (e.g., sucrose or lactose), a buffer (e.g., phosphate, citrate, acetate and other organic acid salts), an antioxidant (e.g., ascorbic acid), a low molecular weight (less than about ten residues) peptide (e.g. polyarginine), a protein (e.g., serum albumin, gelatin, or immunoglobulins), a hydrophilic polymer (e.g., polyvinylpyrrolidinone), an amino acid (e.g., glycine, glutamic acid, aspartic acid, or arginine), a monosaccharide, a disaccharide, and other carbohydrates (e.g. cellulose or its derivatives, glucose, mannose or dextrins), a chelating agent (e.g., EDTA), sugar alcohol (e.g., mannitol or sorbitol), a counterion (e.g., sodium) and/or nonionic surfactants such as TWEEN, Pluronics or polyethyleneglycol. Additional acceptable adjuvants include those well known in the pharmaceutical field, and as described, for example, in Remington's Pharmaceutical Sciences, Mack Publishing Co., (A.R. Gennaro edit. 1985).

A pharmaceutical composition of the invention, especially when administered in capsule form, may also contain a liquid carrier such as, for example, water, saline, or a fatty oil. Other materials of various types may be used as coatings or as modifiers of the physical form of the pharmaceutical composition. For example, dissolution or suspension of the active compound of the invention in a vehicle such as an oil or a synthetic fatty vehicle like ethyl oleate, or into a liposome may be desired.

According to the invention, such materials as well as compounds of the invention are nontoxic to the recipients at the dosages and concentrations employed, i.e. are pharmaceutically acceptable.

In general, a compound of the invention, alone or as part of a pharmaceutical composition as described herein, may be used as a diagnostic or therapeutic agent for the prevention and/or treatment of a condition in a mammal characterized by undesired coagulation disorders (e.g., thrombotic and prothrombotic states in which the coagulation cascade is activated), preferably, for the treatment or prophylaxis of those diseases which involve the production and/or action of factor Xa/prothrombinase complex. Preferably, a compound of the invention, alone or as part of a pharmaceutical composition, as described herein, may be used as a diagnostic or therapeutic agent in the prevention or treatment of a condition characterized by undesired thrombosis, such as (a) the treatment or prevention of any thrombotically mediated acute coronary syndrome including myocardial infarction, unstable angina, refractory angina, occlusive coronary thrombus occurring post—thrombolytic therapy or post—coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g., renal dialysis, cardiopulmonary bypass or other oxygenation procedure, plasmapheresis), (f) the treatment or prevention of thrombotic complications associated with instrumentation (e.g., cardiac or other intravascular catheterization, intra—aortic balloon pump, coronary stent or cardiac valve), and (g) those involved with the fitting of prosthetic devices.

Other conditions against which a compound of the invention, alone or as part of a pharmaceutical composition, are effective include, but are not limited to, reocclusion or restenosis of reperfused coronary arteries, thromboembolic complications of surgery and peripheral arterial occlusion.

Accordingly, the invention provides a method for preventing or treating a condition in a mammal characterized by undesired thrombosis comprising administering a therapeutically effective amount of at least one compound of the invention to a mammal, in particular, a human, each as described above.

Anticoagulant therapy is also useful to prevent coagulation of stored whole blood and to prevent coagulation in other biological samples for testing or storage. The compounds of the invention, alone or as part of a pharmaceutical composition, also find utility in inhibiting the coagulation of biological samples. Thus, the compounds of the invention, alone or as part of a pharmaceutical composition, may be added to or contacted with any medium containing or suspected to contain factor Xa and in which it is desired that blood coagulation be inhibited (e.g., when contacting the mammal's blood with material such as vascular grafts, stents, orthopedic prostheses, cardiac stents, valves and prostheses, extra corporeal circulation systems and the like). Thus, the invention also provides a method for inhibiting the coagulation of biological samples comprising the administration of at least one compound of the invention.

A compound of the invention, alone or as part of a pharmaceutical composition of the invention, is able to inhibit thrombus formation with acceptable effects on classical measures of coagulation parameters, platelets and platelet fuction, and acceptable levels of bleeding complications associated with its use. Conditions characterized by undesired thrombosis would include those involving the arterial and venous vasculature. With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

Compounds and pharmaceutical compositions of the invention are suitable for use alone or as part of a multi-component treatment regimen in combination with other therapeutic or diagnostic agents such as, for example, anticoagulant agents, thrombolytic agents, or other antithrombotic agents (e.g., platelet aggregation inhibitors, tissue plasminogen activators, urokinase, prourokinase, streptokinase, heparin, aspirin, and warfarin). Coadministered compounds and agents may act in a synergistic fashion to, for example, prevent reocclusion following a successful thrombolytic therapy and/or reduce the time to reperfiision. Coadministration may also allow for reduced doses of the thrombolytic agents to be used and therefore minimize potential hemorrhagic side-effects.

The compounds and pharmaceutical compositions of the invention may be utilized in vivo, ordinarily in mammals such as primates, such as humans, sheep, horses, cattle, pigs, dogs, cats, rats and mice, or in vitro. The biological properties, as described above, of the compounds of the invention can be readily characterized by methods that are well known in the art including, for example, in vitro protease activity assays and in vivo studies to evaluate antithrombotic efficacy, and effects on hemostasis and hematological parameters, such as are illustrated in the examples.

A compound or a pharmaceutical composition of the invention may be administered in solid or liquid form depending upon the desired application. For example, diagnostic applications will typically utilize compositions of the invention in the form of a solution or suspension. In the management of thrombotic disorders, a compound or pharmaceutical composition of the invention may be administered in solid form such as, for example, tablets, capsules, suppositories, in liquid form such as, for example, elixirs for oral administration, sterile solutions, sterile suspensions or injectable administration, and the like, or incorporated into shaped articles. A compound or a pharmaceutical composition of the invention may also be administered as sustained release and timed release formulations.

A compound of the invention, alone or as part of a pharmaceutical composition, may also be administered in the form of implanted pellets and small cylinders, aerosols, oral dosage formulations and topical formulations such as ointments, drops and dermal patches. A compound or a pharmaceutical composition of the invention are preferably incorporated into shaped articles such as implants which may employ inert materials such as biodegradable polymers or synthetic silicones, for example, Silastic, silicone rubber or other commercially available polymers.

A compound of the invention, alone or as part of a pharmaceutical composition, may be delivered as a liquid by means of a container having a sterile access port (e.g., an intravenous solution bag or vial having a stopper pierceable by hypodermic injection needle) or as part of a liposome delivery system (e.g. small unilamellar vesicles, large unilamellar vesicles and multilamellar vesicles). Liposomes can be formed from a variety of lipids, such as cholesterol, stearylamine or phosphatidylcholines.

A compound of the invention, alone or as part of a pharmaceutical composition, may also be delivered by coupling the compound to an antibody, an antibody fragment, a growth factor, a hormone, or other similar targeting/delivery vehicles. A compound of the invention, alone or as part of a pharmaceutical composition, may also be coupled with suitable polymers as targetable drug carriers. Such polymers include, but are not limited to, polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, compounds of the invention acting as factor Xa inhibitors alone or as part of a pharmaceutical composition may be coupled to a class of biodegradable polymers useful in achieving controlled release of a drug such as, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Subjects, preferably mammalian, in need of treatment may be administered a therapeutically effective amount, i.e., a dosage that will provide optimal efficacy, of a compound of the invention, alone or as part of pharmaceutical composition. As would be recognized by those of skill in the art, a "therapeutically effective amount" and mode of administration will vary from subject to subject and thus will be determined on a case by case basis. Factors to be considered include, but are not limited to, the subject (e.g. mammal) being treated, its sex, weight, diet, concurrent medication, overall clinical condition, the particular compounds employed, and the specific use for which these compounds are employed. Therapeutically effective amounts or dosages may be determined by either in vitro or in vivo methods.

Modes of administration include those known in the art such as, for example, by injection, intravenous (bolus and/or infusion), subcutaneous, intramuscular, colonic, rectal, nasal and intraperitoneal administration. Preferably, the mode of administration is by injection.

For injection by hypodermic needle, it may be assumed the dosage is delivered into the body's fluids. For other routes of administration, the absorption efficiency may be individually determined for each compound of the invention by methods well known in pharmacology. Accordingly, as would be understood by one of skill in the art, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, a compound of the invention is administered at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of the invention alone or as part of a pharmaceutical composition may be administered several times daily, and other dosage regimens may also be useful. Preferably, a compound of the invention is administered in an effective amount within the dosage range of about 0.1 to about 100 mg/kg, preferably about 0.5 to about 50 mg/kg and more preferably about 1 to about 20 mg/kg on a regimen in a single or 2 to 4 divided daily doses and/or continuous infusion.

A compound of the invention, alone or as part of a pharmaceutical composition, for administration may be sterilized prior to administration. Sterility may be readily accomplished by filtration through sterile membranes such as 0.2 micron membranes, or by other conventional methods. A compound of the invention, alone or as part of a pharmaceutical composition, typically may be stored in lyophilized form or as an aqueous solution. The pH typically will range between about 3–11, more preferably, between about 5–9, and most preferably, between about 7–8. It is understood that use of certain excipients, carriers, or stabilizers, as described herein, may result in the formation of cyclic polypeptide salts.

It should be understood that the foregoing discussion merely presents a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of formula IIa or IIb:

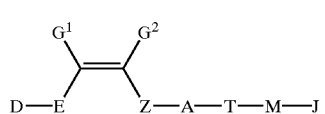

(IIa)

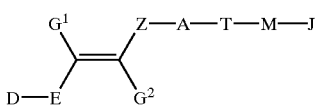

(IIb)

wherein:

D is

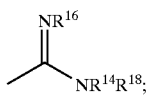

where $R^{14}$ and $R^{16}$ are independently selected from the group consisting of H, —$(CH_2)_{0-12}$—SH, —$(CH_2)_{1-12}$—OH, —$(CH_2)_{0-12}$—$NH_2$, —$(CH_2)_{0-12}$—$_{12}$—$C_{0-6}$—$(CH_2)_{0-12}$—F, —$(CH_2)_{0-12}$—Br, —$(CH_2)_{0-12}$—I, —$(CF_2)_{1-5}$—$(CF_3)$, —$(CH_2)_{0-12}$—$(CF_3)$, —$(CH_2)_{0-12}$—CN, —$(CH_2)_{0-12}$—$NO_2$, —$(CH_2)_{0-12}$—CHO, —$C_{1-12}$alkyl, —$C_{0-12}$alkyl—$N(R^{a'})(R^{3'})_{0-1}$—$C_{0-12}$alkyl, —$(CH_2)_{0-12}$—CH=$(CH)_{0-1}$—$(CH_2)_{1-12}(CH_3)_{0-1}$, —O—$C_{1-12}$alkyl—$N(R^{a'})(R^{b'})_{0-1}$—$C_{0-12}$alkYl, —$C_{1-12}$alkyl—O—$C_{1-12}$alkyl, —$C_{0-12}$alkyl—O—$C_{2-12}$alkenyl, —$C_{2-12}$alkenyl—O—$C_{1-12}$alkyl, —$C_{2-12}$alkinyl, —$C_{0-12}$alkyl—O—$C_{1-6}$alkinyl, —$C_{0-12}$alkinyl—O—$C_{0-12}$alkyl—, —$C_{6-10}$aryl, —$C_{0-12}$alkyl—O—$C_{6-10}$aryl, —$S(=O)_{10-12}$—$C_{1-12}$alkyl—$N(R^{a'})(R^{b'})_{0-1}$—$C_{1-12}$alkyl, —$C_{0-12}$alkyl—$S(=O)_{0-2}$—$C_{1-12}$alkyl, —$C_{0-12}$alkyl—$S(=O)_{0-2}$—$C_{2-12}$alkenyl, —$C_{2-12}$alkenyl—$S(=O)_{0-2}$—$C_{1-12}$alkyl, —$C_{0-12}$alkyl—$S(=O)_{0-2}$—$C_{1-6}$alkinyl, —$C_{0-12}$alkinyl—$S(=O)_{0-2}$—$C_{0-12}$alkyl—, —$C_{0-12}$alkyl—$S(=O)_{0-2}$—$C_{6-10}$aryl, —$C_{0-12}$alkyl$C_{6-10}$aryl, —$C_{2-12}$alkenyl$C_{6-10}$aryl, —$C_{2-12}$alkinyl$C_6$aryl, —COOH, —$C_{0-12}$alkyl—COO—$C_{1-12}$alkyl, —$C_{0-12}$alkyl—COO—$C_{2-12}$alkenyl, —$C_{1-12}$alkyl—COO—$C_{2-12}$alkinyl, —$C_{2-12}$alkenyl—COO—$C_{1-12}$alkyl, —$C_{2-12}$alkinyl—COO—$C_{1-12}$alkyl, —$C_{2-6\ 12}$alkenyl—COO—$C_{1-12}$alkyl, —$C_{2-12}$alkinyl—COO—$C_{1-12}$alkyl, —$C_{6-10}$aryl monocyclic or bicyclic ring structure, and a three to ten membered heterocyclic monocyclic or bicyclic heterocyclic ring structure containing 1–4 heteroatoms selected from N, O and S;

$R^{a'}$ and $R^{b'}$ are each independently selected from the group consisting of H, —CN, —$C_{0-6}$alkyl—SH, —$C_{0-6}$alkyl—OH, —$C_{0-6}$alkyl—CHO, —$C_{0-6}$alkyl—COOH, —$C_{0-6}$alkyl—N $R^{c'}R^{d'}$, —$C_{0-6}$alkenyl—SH, —$C_{0-6}$alkenyl—OH, —$C_{0-6}$alkenyl—CHO, —$C_{0-6}$alkenyl—COOH, —$C_{0-6}$alkenyl—N $R^{c'}R^{d'}$, —$C_{0-6}$alkinyl—SH, —$C_{0-6}$alkinyl—OH, —$C_{0-6}$alkinyl—CHO, —$C_{0-6}$alkinyl—COOH, —$C_{0-6}$alkinyl—N $R^{c'}R^{d'}$, —$C_{1-6}$alkyl, —$(CH_2)_{1-6}$—$C_{0-6}$—$(CH_2)_{1-6}$—F, —$(CH_2)_{1-6}$—Br, —$(CH_2)_{1-6}$—I, —$(CF_2)_{1-3}$—$(CF_3)$, —$(CH_2)_{1-6}$—$(CF_3)$, —$(CH_2)_{1-6}$—CN, —$(CH_2)_{0-6}$—$NO_2$, —$C_{1-6}$alkyl, —$(CH_2)_{0-4}$—CH=$(CH)_{0-1}$—$(CH_2)_{0-4}(CH_3)_{0-1}$, —$CO_{0-5}$alkyl—O—$C_{1-6}$alkyl, —$C_{0-5}$alkyl—O—$C_{2-6}$alkenyl, —$C_{2-6}$alkenyl—O—$C_{1-6}$alkyl, —$C_{2-6}$alkinyl, —$C_{0-5}$alkyl—O—$C_{2-6}$alkinyl, —$C_{2-6}$alkinyl—O—$C_{1-6}$alkyl—, —$C_{6-10}$aryl, —$C_{0-6}$alkyl—O—$C_{6-10}$aryl, —$C_{0-6}$alkyl—$S(=O)_{0-2}$—$C_{1-6}$alkyl, —$C_{0-6}$alkyl—$S(=O)_{0-2}$—$C_{2-6}$alkenyl, —$C_{2-6}$alkenyl—$S(=O)_{0-2}$—$C_{16}$alkyl, —$C_{0-6}$alkyl—$S(=O)_{0-2}$—$C_{1-6}$alkinyl, —$C_{2-6}$alkinyl—$S(=O)_{0-2}$—$C_{1-6}$alkyl—, —$C_{0-6}$alkyl—$S(=O)_{0-2}$—$C_{6-10}$aryl, —$C_{0-6}$alkyl$C_{6-10}$aryl, —$C_{2-6}$alkenyl$C_{6-10}$aryl, —$C_{2-6}$alkinyl$C_{6-10}$aryl, —$C_{0-6}$alkyl—COO—$C_{1-6}$alkyl, —$C_{0-6}$alkyl—COO—$C_{2-6}$alkenyl, —$C_{0-1}$alkyl—COO—$C_{2-6}$alkinyl, —$C_{2-6}$alkenyl—COO—$C_{1-6}$alkyl, —$C_{2-6}$alkinyl—COO—$C_{1-6}$alkyl, —$C_{2-6}$alkenyl—COO—$C_{1-6}$alkyl, —$C_{2-6}$alkinyl—COO—$C_{1-6}$alkyl, a three to ten membered monocyclic or bicyclic heterocyclic ring structure containing 14 heteroatoms selected from N, O and S, and Ra, and Rb, taken together or with a carbon atom having a free hydrogen to form an intracyclic bond resulting in a three to ten membered heterocyclic ring having from 1-4 heteroatoms selected from N, O and S, where the alkyl, alkenyl, and alkinyl portions of said $R^{a'}$ and $R^{b'}$, may be linear or branched and substituted with from 0–6 members independently selected from the group consisting of —I, —F, —Br, —OH, —$NO_2$, —$CF_3$, —CHO, —$NH_2$ and —COOH;

$R^{c'}$ and $R^{d'}$ are independently selected from the group consisting of H, $C_{1-6}$alkyl—CHO, $C_{0-6}$alkyl—COOH, $C_{0-6}$alkyl—COCl, $C_{0-6}$alkyl—COI, $C_{0-6}$alkyl—COF, $C_{0-6}$alkyl—COBr, $C_{0-6}$alkyl—COO—$C_{1-6}$alkyl, $C_{1-6}$alkyl—COO—$C_{2-6}$alkenyl, $C_{1-6}$alkyl—COO—$C_{2-6}$alkinyl, $C_{0-6}$alkyl—COO—$C_{0-6}$alkyl—$CF_3$, $C_{1-6}$alkyl—COO—$C_{6-10}$aryl —COOH, $C_{0-6}$alkyl—CN, $C_{2-6}$alkyl—$NO_2$, $C_{1-6}$alkyl—$C_{0-6}C_{1-6}$alkyl—Br, $C_{1-6}$alkyl—I, $C_{1-6}$alkyl—F, $C_{1-6}$alkyl—$CF_3$, $C_{1-6}$alkyl—$CF_2$—$CF_3$, $C_{1-6}$alkyl—SH, $C_{1-6}$alkyl, $C_{1-6}$alkenyl, $C_{1-6}$alkynyl, $C_{1-6}$alkyloxy, $C_{1-6}$alkenyloxy, $C_{1-6}$alkylthio, $C_{1-6}$alkenylthio, $C_{3-8}$cycloalkyl, $C_{6-10}$aryl, $C_{1-6}$alkyl$C_{6-10}$aryl, a three to ten membered heterocyclic monocyclic or bicyclic ring system containing 1-4 heteroatoms selected from N, O and S; and $C_{1-4}$alkylheterocyclic monocyclic or bicyclic ring system having in the ring system 3 to 10 atoms with 1-14 4 of such atoms being selected from N, O and S;

$R^{18}$ is a member selected from the group consisting H, —$(CH_2)_{0-12}$—SH, —$(CH_2)_{0-12}$—OH, —$(CH_2)_{0-12}$—$NH_2$, —$(CH_2)_{0-12}$—Cl, —$(CH_2)_{0-12}$—F, —$(CH_2)_{0-12}$—Br, —$(CH_2)_{0-12}$—I, —$(CF_2)_{1-5}$—$(CF_3)$, —$(CH_2)_{0-12}$—$(CF_3)$, —$(CH_2)_{1-12}$—CN, —$(CH_2)_{0-12}$—$NO_2$, —$(CH_2)_{0-12}$—CHO, —$C_{0-12}$alkyl, —$C_{0-12}$alkyl—N$(R^{3'})(R^{b'})_{0-1}$—$C_{0-12}$alkyl, —$(CH_2)_{0-12}$—CH=$(CH)_{0-1}$—$(CH_2)_{0-12}(CH_3)_{0-1}$, —O—$C_{1-12}$alkyl—N$(R^{3'})(R^{b'})_{0-1}$—$C_{0-12}$alkyl, —$C_{1-12}$alkyl—O—$C_{1-12}$alkyl, —$C_{0-12}$alkyl—O—$C_{2-12}$alkenyl, —$C_{2-12}$alkenyl—O—$C_{1-12}$alkyl, —$C_{2-12}$alkinyl, —$C_{0-12}$alkyl—O—$C_{1-6}$alkinyl, —$C_{0-12}$alkinyl—O—$C_{0-12}$alkyl—, —$C_{6-10}$aryl, —$C_{0-12}$alkyl—O—$C_{6-10}$aryl, —$S(=O)_{0-2}$—$C_{1-12}$alkyl—$N(R^{a'})(R^{b'})_{01}$—$C_{1-12}$alkyl, —$C_{0-12}$alkyl—$S(=O)_{0-2}$—$C_{1-12}$alkyl, —$C_{1-12}$alkyl—$S(=O)_{0-2}$—$C_{2-12}$alkenyl, —$C_{2-12}$alkenyl—$S(=O)_{0-2}$—$C_{1-12}$alkyl, —$CO_2$alkyl—$S(=O)_{0-2}$—$C_{1-6}$alkinyl, —$C_{0-12}$alkinyl—$S(=O)_{0-2}$—$C_{0-12}$alkyl—, —$C_{-12}$alkyl—$S(=O)_{0-2}$—$C_{6-10}$aryl, —$C_{0-12}$alkyl$C_{6-10}$aryl, —$C_{2-12}$alkenyl$C_{60-10}$aryl, —$C_{2-12}$alkinyl$C_{6-10}$aryl, —COOH, —$C_{0-12}$alkyl—COO—$C_{1-12}$alkyl, —$C_{0-12}$alkyl—COO—$C_{2-12}$alkenyl, —$C_{0-12}$alkyl—COO—$C_{2-12}$alkinyl, —$C_{2-12}$alkenyl—COO—$C_{1-12}$alkyl, —$C_{2-12}$alkinyl—COO—$C_{1-12}$alkyl, —$C_{2-12}$alkenyl—COO—$C_{1-12}$alkyl, —$C_{2-12}$alkinyl—COO—$C_{1-12}$alkyl, —$C_{6-10}$aryl monocyclic or bicyclic ring structure, and a three to ten membered heterocyclic monocyclic or bicyclic heterocyclic ring structure containing 1-4 heteroatoms selected from N, O and S, wherein Rat and Rb' are each as defined above;

E is a $C_{3-16}$ carbocyclic ring structure or a three to ten membered heterocyclic monocyclic or bicyclic ring structure system containing 14 heteroatoms selected from N, O and S, substituted with 0 to 4 R groups independently selected from the group consisting of H, —SH, —OH, —C$_{0-6}$—F, —Br, —I, —CN, —NO$_2$, —CHO, —COOH, —NR'R" and a substituent member, wherein said substituent member is selected from the group consisting of a linear or branched C$_{1-12}$alkyl group, a linear or branched C$_{2-12}$alkenyl group, a linear or branched C$_{2-12}$alkinyl group and a C$_{3-12}$cycloalkyl group containing linear or branched chained portions, and wherein said substituent member contains 0 to 4 chain bridging groups independently selected from the group consisting of —NH—, —O—, —S—, —S(=O)—, and —S(=O)$_2$—, and wherein for each of said substituent member:
(a) two hydrogens on the same carbon atom of said alkyl, alkenyl, alkinyl or cycloalkyl substituent member are replaced with =O or =N(R'");
(b) one or more hydrogens, independently, on said alkyl, alkenyl, alkinyl or cycloalkyl substituent member or on the —NH—chain bridging groups are replaced by R$^{iv}$; or
(c) one or more hydrogens, independently, on carbon atom(s) of said alkyl, alkenyl, alkinyl or cycloalkyl substituent member, on said —NH—chain bridging group or on R$^1$, R", R$^1$ "or Riv are replaced to form an intracyclic bond resulting in a C$_{3-12}$carbocyclic ring structure or a three to seven membered heterocyclic ring containing 1-4 heteroatoms selected from N, O and S;

R',R", R'" and R$^{iv}$ are independently selected from the group consisting of H, —(CH$_2$)$_{0-12}$—SH, —(CH$_2$)$_{0-12}$—OH, —(CH$_2$)$_{0-12}$—NH$_2$, —(CH$_2$)$_{0-12}$—Cl, (CH$_2$)$_{0-12}$—F, —(CH$_2$)0-12—Br, —(CH$_2$)$_{0-12}$—I, —(CF$_2$)$_{1-5}$—(CF$_3$), —(CH$_2$)$_{0-12}$—(CF$_3$), —(CH$_2$)$_{0-12}$—CN, —(CH$_2$)$_{0-12}$—NO$_2$, —(CH$_2$)$_{0-12}$—CHO, —C$_{1-12}$alkyl, —C$_{0-12}$alkyl—N(R$^a$)(R$^b$)$_{0-1}$C$_{0-12}$alkyl, —(CH$_2$)$_{0-12}$—CH=(CH)$_{0-1}$—(CH$_2$)$_{0-12}$(CH$_3$)$_{0-1}$, —O—C$_{1-12}$alkyl—N(R$^a$)(R$^b$)$_{0-1}$—C$_{0-12}$alkyl, —C$_{0-12}$alkyl—O—C$_{1-12}$alkyl, —C$_{0-12}$alkyl—O—C$_{2-12}$alkenyl, —C$_{2-12}$alkenyl—O—C$_{1-12}$alkyl, —C$_{2-12}$alkinyl, —C$_{0-12}$alkyl—O—C$_{1-6}$alkinyL, —C$_{0-12}$alkinyl—O—C$_{0-12}$alkyl—, —C$_{6-10}$aryl, —C$_{0-12}$alkyl—O—C$_{6-10}$aryl, —S(=O)$_{0-2}$—C$_{1-12}$alkyl—N(R$^a$)(R R$^{a'}$ and R$^{b'}$ are each independently selected from the group consisting of H, -CN, 2. A compound of claim 1, wherein
X is selected from the group consisting of —N—, —O—, —C(=O)—, —S—, —SO—, and —SO$_2$—;
r and t are each independently an integer from 0–6; and
R$^1$ is a member independently selected from the group consisting of H, —OH, halogen, trihalomethyl, —CN, —NO$_2$, C$_{1-6}$alkyl, C$_{3-8}$cycloalkyl, —O—C$_{1-6}$alkyl, C$_{1-6}$alkenyl, —O—C$_{1-6}$alkenyl, C$_{1-6}$alkinyl, —O—C$_{1-6}$alkinyl, C$_{6-10}$aryl, —O—C$_{6-10}$aryl, C$_{1-6}$alkylC$_{1-6}$aryl, —O—C$_{1-6}$alkylC$_{1-6}$aryl, —COOH, and —COO—C$_{1-6}$alkyl.

3. A compound of claim 1, wherein
E, A and T are independently selected from the group consisting of phenyl, naphthyl, biphenyl, 2-pyridyl, 3-pyridyl, 4-pyridyl, 1,2-pyrimidyl, 1,3-pyrimidyl, 1,4-pyrimidyl, morpholinyl, thiomorpholinyl, piperidinyl, thiophenyl, oxaxolyl, isoxazolyl, thiazolyl, isothiazolyl, imidazolyl and triazole, wherein are E, A, and T are each substituted with O to 4 R groups independently selected from the group consisting of H, —OH, halogen, trihalomethyl, —CN, —NO$_2$, C$_{1-6}$alkyl, C$_{3-8}$cycloalkyl, —O—C$_{1-6}$alkyl, C$_{1-6}$alkenyl, —O—C$_{1-6}$alkenyl, C$_{1-6}$alkinyl, —O—C$_{1-6}$alkinyl, C$_{6-10}$aryl, —O—C$_{6-10}$aryl, C$_{1-6}$alkylC$_{6-10}$aryl, —O—Cl$_6$alkylC$_{6-10}$aryl, —COOH, —COO—C$_{1-6}$alkyl, any two R groups taken together form a methylenedioxy or ethylenedioxy group, and any two R groups taken together cyclize with a monocyclic heterocyclic group of E, A or T to form a bicyclic heterocyclic group.

4. A compound of claim 1, wherein:
J1 is selected from the group consisting of H, —CN, —NR$^9$R$^{10}$,

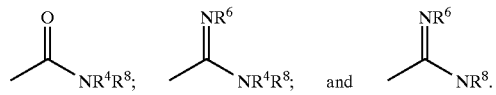

5. A compound of claim 1, wherein:
E, A, and T are independently selected from the group consisting of phenyl, naphthyl, 2-pyridyl, 3-pyridyl, 4-pyridyl, oxaxolyl, isoxazolyl, thiazolyl, isothiazolyl, imidazolyl and triazole, indolyl, and quinolinyl, which are independently substituted with O to 4 R groups independently selected from the group consisting of H, —OH, halogen, trihalomethyl, —CN, —NO$_2$, C$_{1-6}$alkyl, C$_{3-8}$cycloalkyl, —O—C$_{1-6}$alkyl, C$_{1-6}$alkenyl, —O—C$_{1-6}$alkenyl, C$_{1-6}$alkinyl, —O—C$_{1-6}$aklknyl, C$_{6-10}$aryl, —O—C$_{6-10}$aryl, C$_{1-6}$alkylC$_{6-10}$aryl, —O—C$_{6-10}$alkylC$_{6-10}$aryl, —COOH, —COO—C$_{1-6}$alkyl, and any two R groups taken together form a methylenedioxy or ethylenedioxy group;

Z is selected from the group consisting of —(CH$_2$)$_{0-6}$—O—(CH$_2$)$_{0-6}$—, —(CH$_2$)$_{0-6}$—C(=O)—(CH$_2$)$_{0-6}$—, —(CH$_2$)$_{0-6}$—C(=O)—O—(CH$_2$)$_{0-6}$—, —(CH$_2$)$_{0-6}$—C(=O)—(CH$_2$)$_{0-6}$—, —(CH$_2$)$_{0-6}$—C(=N(R$^{36}$))—(CH$_2$)$_{0-6}$—, —C(=O)—N(R$^{36}$)—(CH$_2$)$_{0-6}$—, —N(R$^{36}$)—C(=O)—(CH$_2$)$_{0-6}$—, —(CH$_2$)$_{0-6}$—S—(CH$_2$)$_{0-6}$—, —(CH$_2$)$_{0-6}$—S(O)$_2$—(CH$_2$)$_{0-6}$—, —(CH$_2$)$_{0-6}$—S(O)$_2$—N(R$^{36}$)—(CH$_2$)$_{0-6}$—, —(CH$_2$)$_{0-6}$—N(R$^{36}$)—SO$_2$—(CH$_2$)$_{0-6}$—, and —(CH$_2$)$_{0-6}$—N(R$^{36}$)—SO$_2$—N(R$^{37}$)—(CH$_2$)$_{0-6}$—; and M is selected from the group consisting of —(CH$_2$)$_{0-6}$—O—(CH$_2$)$_{0-6}$—, —(CH$_2$)$_{0-6}$—C(=O)—(CH$_2$)$_{0-6}$—, —(CH$_2$)$_{0-6}$—C(=O)—O—(CH$_2$)$_{0-6}$—, —(CH$_2$)$_{0-6}$—O—C(=O)—(CH$_2$)$_{0-6}$—, —(CH$_2$)$_{0-6}$—S—(CH$_2$)$_{0-6}$—, —(CH$_2$)$_{0-6}$—S(O)—(CH$_2$)$_{0-6}$—, —(CH$_2$)$_{0-6}$—S(O)$_2$—(CH$_2$)$_{0-6}$—, —(CH$_2$)$_{0-6}$—N(R$^{3"}$)—(CH$_2$)$_{0-6}$—, —(CH$_2$)$_{0-6}$—C(=N(R$^{3"}$))—(CH$_2$)$_{0-6}$—, and —(CH$_2$)$_{0-6}$—S(O)$_2$—N(R$^{3"}$)—(CH$_2$)$_{0-6}$—.

6. A compound of claim 1, wherein:
E, A, and T are independently selected from the group consisting of phenyl, 2-pyridyl, 3-pyridyl, 4-pyridyl, oxaxolyl, isoxazolyl, thiazolyl, isothiazolyl and imidazolyl, which are substituted with 0 to 4 R groups independently selected from the group consisting of H, —OH, halogen, trihalomethyl, —CN, —NO$_2$, C$_{1-6}$alkyl, C$_{3-8}$cycloalkyl, and —O—C$_{0-6}$alkyl;

Z is selected from the group consisting of —C(=O)—N(R$^{36}$)—(CH$_2$)$_{0-6}$—, —N(R$^{36}$)—C(=O)—(CH$_2$)$_{0-6}$—, —(CH$_2$)$_{0-6}$—S(O)$_2$—N(R$^{36}$)—(CH$_2$)$_{0-6}$— and —(CH$_2$)$_{0-6}$—N(R$^{36}$)—SO$_2$—(CH$_2$)$_{0-6}$—;

M is selected from the group consisting of —(CH$_2$)$_{0-6}$—C(=O)—(CH$_2$)$_{0-6}$—, —(CH$_2$)$_{0-6}$—S(O)—(CH$_2$)$_{0-6}$—, —(CH$_2$)$_{0-6}$—S(O)$_2$—(CH$_2$)$_{0-6}$—, —(CH$_2$)$_{0-6}$—C(=N(R$^{38}$))—(CH$_2$)$_{0-6}$— and —(CH$_2$)$_{0-6}$—N(R$^{38}$)—(CH$_2$)$_{0-6}$—.

7. A compound of claim 1, wherein:

E, A, and T are independently selected from the group consisting of phenyl, 2—pyridyl, 3-pyridyl and 4-pyridyl, which are substituted with 0 to 4 R groups which are independently a member selected from the group consisting of H,—OH, halogen, trihalomethyl, —CN, —$NO_2$, $C_{1-6}$alkyl and —O—$C_{1-6}$alkyl;

Z is selected from the group consisting of —C(=O)—N($R^{36}$)—$(CH_2)_{0-6}$— and —N($R^{36}$)—C(=O)—$(CH_2)_{0-6}$—; and M is selected from the group consisting of —$(CH_2)_{0-6}$—C(=O)—$(CH_2)_{0-6}$—, —$(CH_2)_{0-6}$—$S(O)_2$—$(CH_2)_{0-6}$—, and —$(CH_2)_{0-6}$—C(=N($R^{38}$))—$(CH_2)_{0-6}$—.

8. A compound of claim 7, wherein

Z is selected from the group consisting of —C(=O)—N($R^{36}$)— and —N($R^{36}$)—C(=O)—; and M is selected from the group consisting of —C(=O)—, —$S(O)_2$—, and —C(=N($R^{38}$))—.

9. A compound of claim 1 having the following structure:

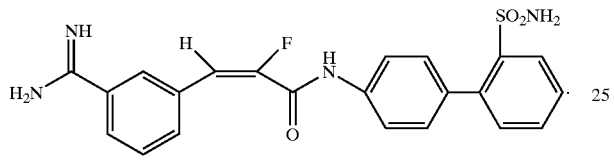

10. A pharmaceutical composition comprising a pharmaceutically acceptable carrier and a compound of one of claims 1–9.

11. A method for the treatment of a condition in a mammal characterized by undesired thrombosis comprising the step of administering a therapeutically effective amount of a compound of one of claims 1–9.

12. A method for the prevention or treatment of thrombosis of claim 11, wherein the condition is selected from the group consisting of unstable angina, refractory angina, myocardial infarction, occlusive coronary thrombus, transient ischemic attacks, thrombotic stroke, embolic stroke, disseminated intravascular coagulation, septic shock, deep venous thrombosis, pulmonary embolism, reocclusion or restenosis of reperfused coronary arteries, thromboembolic complications of surgery and peripheral arterial occlusion.

13. A method for inhibiting the coagulation of a biological sample comprising the step of administering a compound of one of claims 1–9 to the biological sample.

* * * * *